United States Patent
Chi et al.

(10) Patent No.: US 9,133,143 B2
(45) Date of Patent: Sep. 15, 2015

(54) (3-FLUORO-2-HYDROXY)PROPYL-FUNCTIONALIZED ARYL DERIVATIVES OR PHARMACEUTICALLY ACCEPTABLE SALTS THEREOF, METHOD FOR PREPARING SAME, AND PHARMACEUTICAL COMPOSITION CONTAINING SAME AS ACTIVE INGREDIENT FOR THE DIAGNOSIS OR TREATMENT OF NEURODEGENERATIVE BRAIN DISEASES

(75) Inventors: Dae-Yoon Chi, Seoul (KR); Byoung-Se Lee, Seoul (KR); Sirion Uthaiwan, Chainat (TH); So-Young Chu, Seoul (KR); Yu-Jin Bae, Incheon (KR); Chansoo Park, Seoul (KR); Dae-Hyuk Moon, Seoul (KR); Jin-Sook Ryu, Seoul (KR); Jae-Seung Kim, Seoul (KR); Seung-Jun Oh, Seoul (KR)

(73) Assignee: FUTURECHEM CO., LTD., Incheon (KR)

( * ) Notice: Subject to any disclaimer, the term of this patent is extended or adjusted under 35 U.S.C. 154(b) by 86 days.

(21) Appl. No.: 13/505,159

(22) PCT Filed: Sep. 14, 2010

(86) PCT No.: PCT/KR2010/006252
§ 371 (c)(1),
(2), (4) Date: Apr. 30, 2012

(87) PCT Pub. No.: WO2011/052888
PCT Pub. Date: May 5, 2011

(65) Prior Publication Data
US 2012/0214994 A1    Aug. 23, 2012

(30) Foreign Application Priority Data
Oct. 29, 2009    (KR) .......................... 10-2009-0103668

(51) Int. Cl.
C07D 417/04    (2006.01)
A61K 31/4436    (2006.01)
C07D 277/66    (2006.01)
C07D 409/04    (2006.01)
C07D 471/04    (2006.01)

(52) U.S. Cl.
CPC ............ *C07D 277/66* (2013.01); *C07D 409/04* (2013.01); *C07D 417/04* (2013.01); *C07D 471/04* (2013.01)

(58) Field of Classification Search
CPC . C07D 409/04; C07D 417/04; A61K 31/4436
USPC ..................... 546/281.1, 270.1; 514/337, 338
See application file for complete search history.

(56) References Cited

U.S. PATENT DOCUMENTS

| 2009/0016958 A1 | 1/2009 | Kolb |
| 2009/0264403 A1 | 10/2009 | Schwink |
| 2010/0298298 A1 | 11/2010 | Clauss |

FOREIGN PATENT DOCUMENTS

| EP | 1967517 A1 | 9/2008 |
| WO | 2007-093364 | 8/2007 |
| WO | 2008-109080 | 9/2008 |
| WO | 2009-077680 | 6/2009 |

OTHER PUBLICATIONS

International Search Report for corresponding patent application No. PCT/KR2010/006252 dated Jun. 16, 2011.

*Primary Examiner* — Patricia L Morris
(74) *Attorney, Agent, or Firm* — Renner, Otto, Boisselle & Sklar, LLP

(57) ABSTRACT

The present invention relates to (3-fluoro-2-hydroxy)propyl-functionalized aryl derivatives or to the pharmaceutically acceptable salt thereof, to a method for preparing same, and to a pharmaceutical composition containing same as active ingredients for the diagnosis or treatment of neurodegenerative brain diseases. The aryl derivatives of the present invention are (3-fluoro-2-hydroxy)propyl-functionalized to increase the polarity thereof, and therefore the drugs containing the aryl derivatives can easily permeate into the cerebrovascular membrane, thus increasing the effectiveness of the drugs. As the aryl derivatives of the present invention strongly bind to β-amyloid, the aryl derivatives, when labeled with radioisotope, can be used as a diagnostic agent for non-invasively diagnosing early Alzheimer's disease. Further, the aryl derivatives of the present invention bind to low molecular β-amyloid peptide conjugates to inhibit the generation of malignant high molecular β-amyloid plaque, and thus can be effectively used as a therapeutic agent for neurodegenerative brain diseases such as Alzheimer's disease.

3 Claims, 9 Drawing Sheets

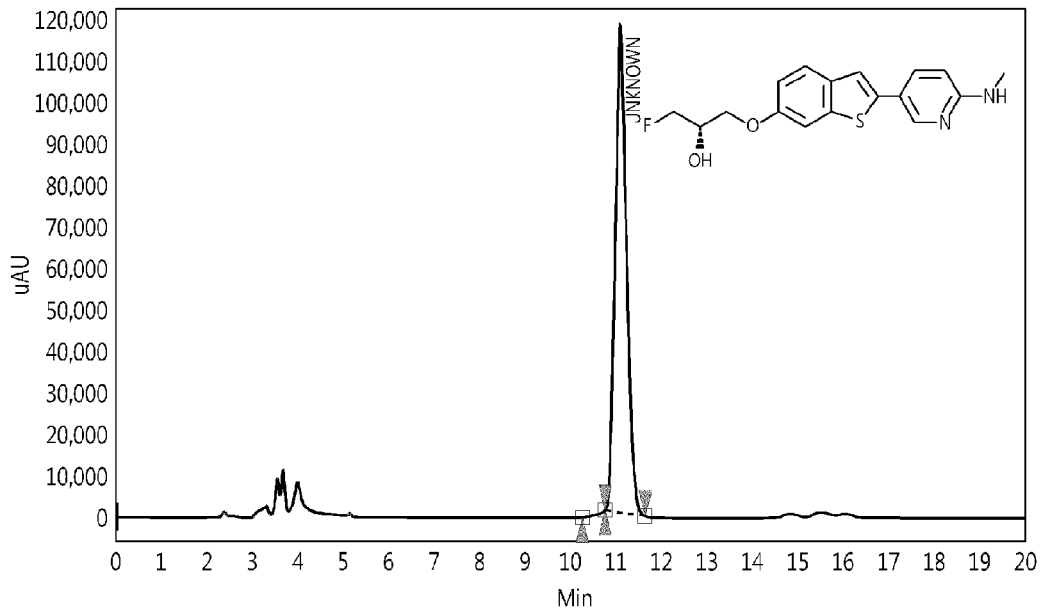
Fig. 3
Fig. 4
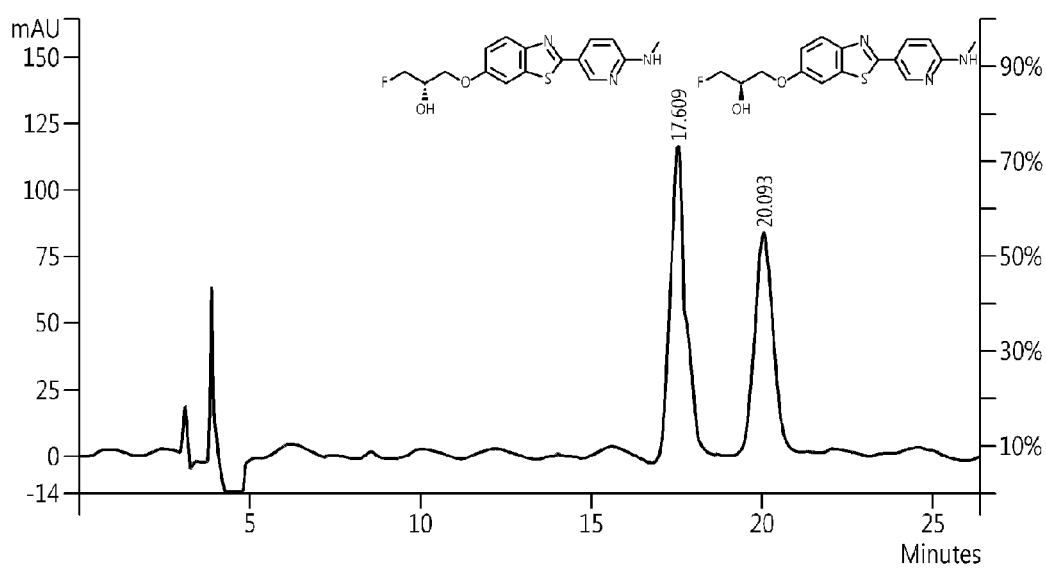

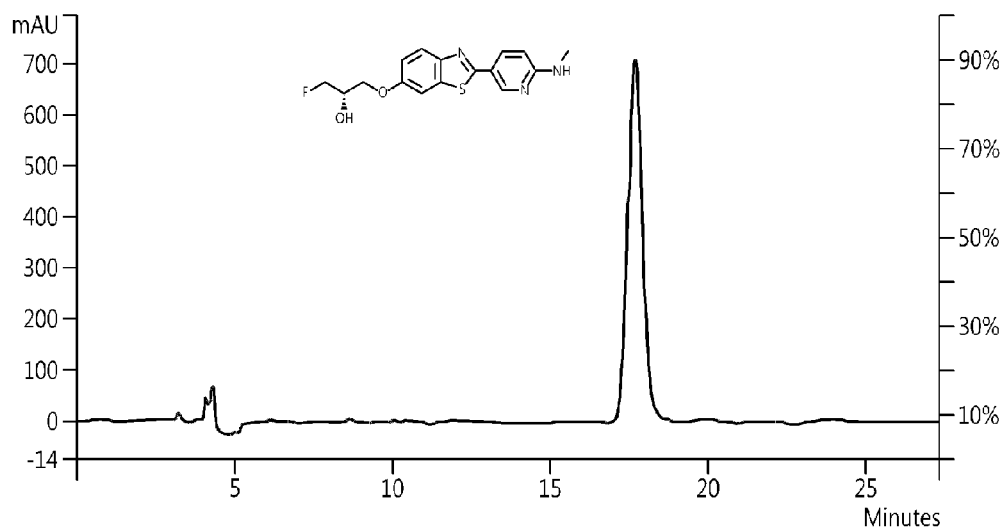
Fig. 6
Fig. 7
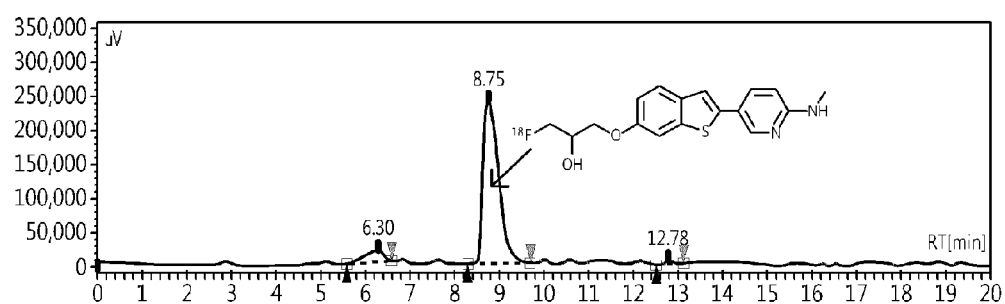

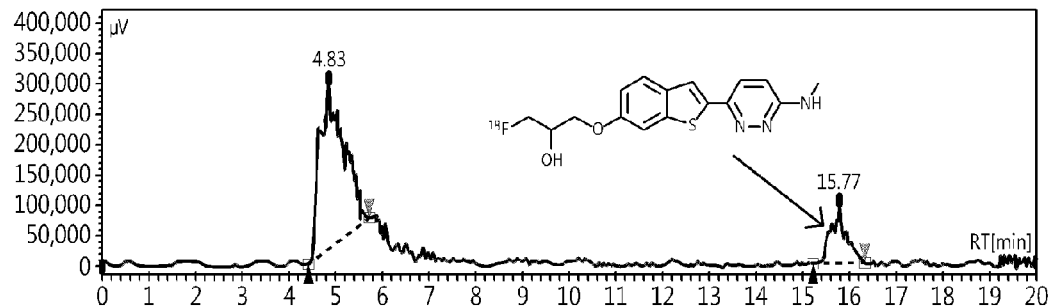
Fig. 8
Fig. 9
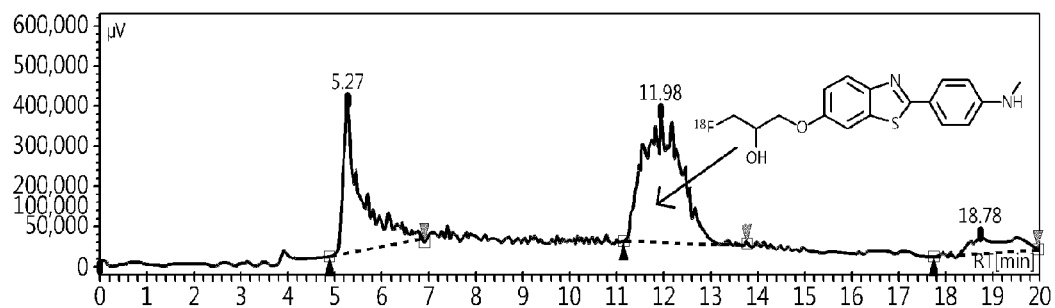

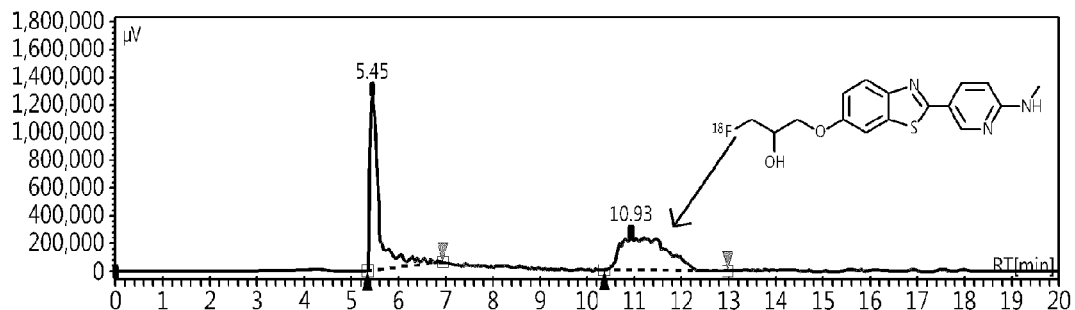
Fig. 10
Fig. 11
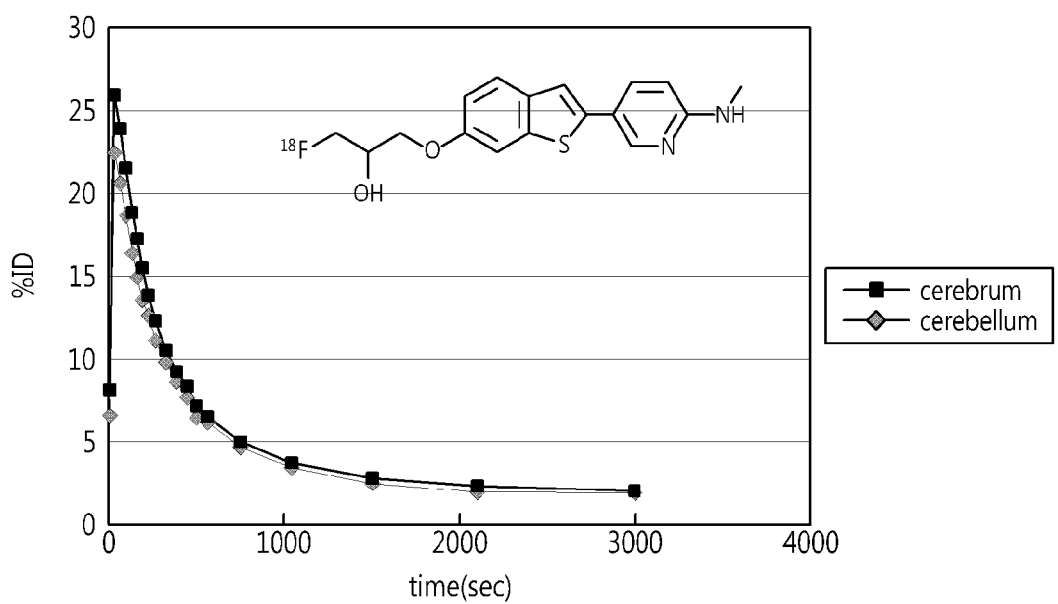

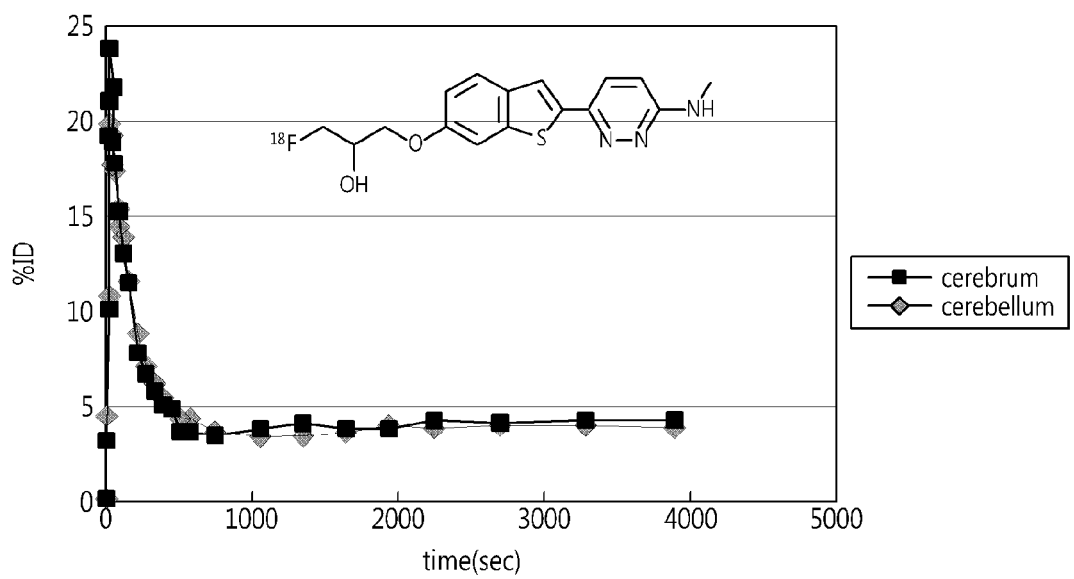
Fig. 12
Fig. 13
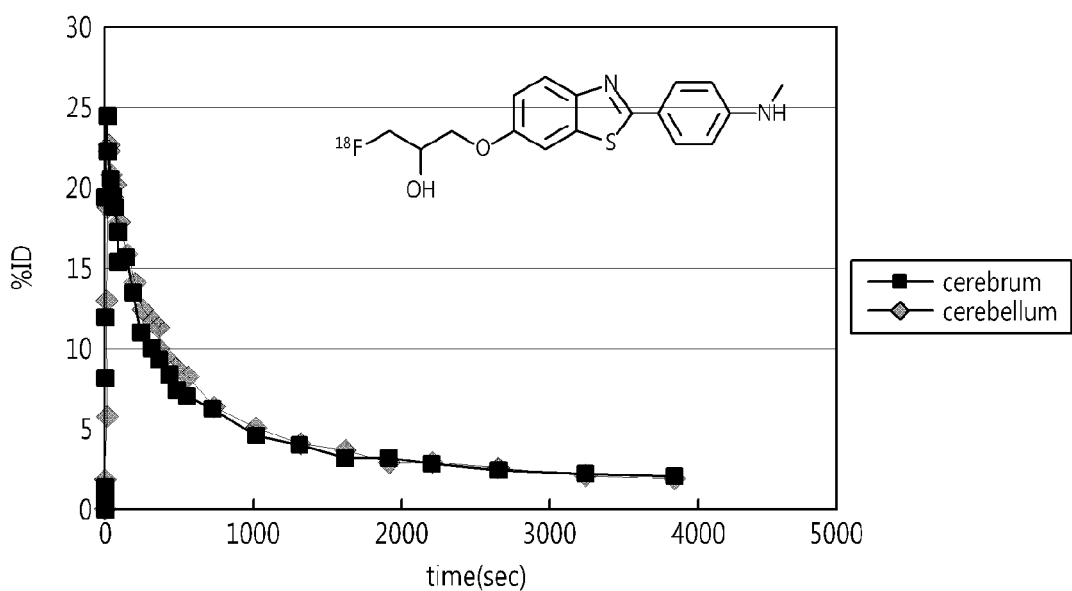

(3-FLUORO-2-HYDROXY)PROPYL-FUNCTIONALIZED ARYL DERIVATIVES OR PHARMACEUTICALLY ACCEPTABLE SALTS THEREOF, METHOD FOR PREPARING SAME, AND PHARMACEUTICAL COMPOSITION CONTAINING SAME AS ACTIVE INGREDIENT FOR THE DIAGNOSIS OR TREATMENT OF NEURODEGENERATIVE BRAIN DISEASES

TECHNICAL FIELD

The present invention relates to (3-fluoro-2-hydroxy)propyl-functionalized aryl derivatives or to the pharmaceutically acceptable salt thereof, to a method for preparing same, and to a pharmaceutical composition containing same as active ingredients for the diagnosis or treatment of degenerative brain diseases.

BACKGROUND ART

Due to the increasing size of the elderly population and negative changes in dietary habits, degenerative brain diseases such as Alzheimer's disease, Parkinson's disease, Huntington's disease, Lou Gehrig's disease and the like are rapidly increasing. Among them, Alzheimer's disease, also known as senile dementia, is a representative degenerative brain disease, causing memory loss, cognitive impairment and death caused by complications if prolonged. Alzheimer's disease may occur at relatively early ages of 40s to 50s. Prevalence increases with age, reaching 40-50% in those who are 85 to 90 years old.

A lot of research results on various degenerative brain diseases including Alzheimer's disease are being reported and drugs targeting various underlying mechanisms are being developed. However, currently available drugs merely slow the progress of diseases and cannot cure them. Thus, at present, early diagnosis is ideal to achieve the best prognosis. Since the pathological change of the degenerative diseases begin about 7 years before symptoms occur, early diagnosis and treatment is essential.

There are two hypotheses as to the causes of Alzheimer's disease. Amyloid plaques and neurofibrillary tangles (NFT) have been found in the brain tissue of patients with Alzheimer's disease. The amyloid plaques are formed outside the nerve cells as amyloid peptides are deposited, and the neurofibrillary tangles are formed inside the nerve cells due to accumulation of tau proteins. The presence of β-amyloid leads to a significant change in biochemical processes, thereby inducing deposition of other proteins and activating phagocytosis by microglia, ultimately resulting in loss of nerve cells and cognitive impairment. The initiation of aggregation of β-amyloid plaques occurs long before clinical symptoms are observed. The current "minimal microscopic criteria for the diagnosis of Alzheimer's disease" are based on the quantity of the β-amyloid plaques detected in the brain. The plaque mainly consists of β-amyloid peptides consisting of 39 to 43 amino acids arranged in 13 sheet structure. Among these, β-amyloid 42 is more toxic and forms plaques more easily than β-amyloid 40 due to the presence of additional hydrophobic amino acid residues.

Accordingly, a compound selectively and strongly binding to β-amyloid aggregates may be developed into a therapeutic agent that suppresses the β-amyloid plaque formation and stops progression of Alzheimer's disease or a molecular probe for β-amyloid aggregates that can be used to diagnose Alzheimer's disease. Until recently, it was impossible to know whether β-amyloid plaques are present in the brain of a patient who is suffering or suspected to be suffering from Alzheimer's disease while the patient is alive. Alzheimer's disease can only be definitively determined based upon staining of brain tissue. The presence of amyloid in the brain can be easily detected by staining the brain tissue with thioflavin S represented by Chemical Formula 1 or congo red represented by Chemical Formula II. When stained with congo red, the amyloid exhibits yellowish green color, which is due to the β sheet structure of the amyloid protein.

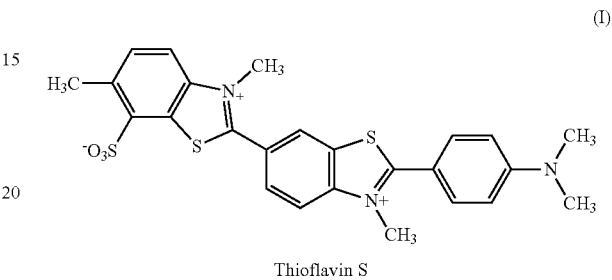

Thioflavin S (I)

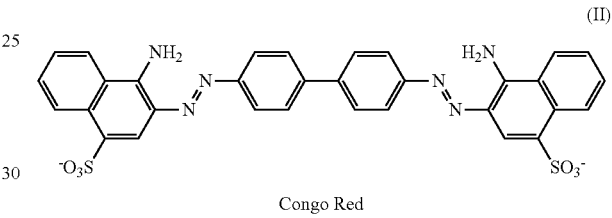

Congo Red (II)

Radioligands that have been reported so far are known to bind at three different sites of the β-amyloid plaque: congo red (Chemical Formula II)-binding site, thioflavin T (Chemical Formula III)-binding site and FDDNP (Chemical Formula IV)-binding site. Among them, the site where thioflavin T binds to the β-amyloid plaque is being studied the most actively.

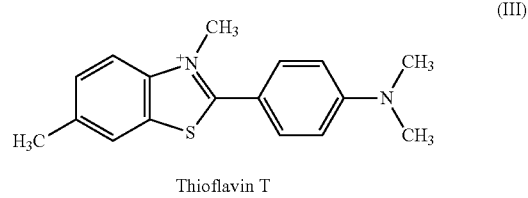

Thioflavin T (III)

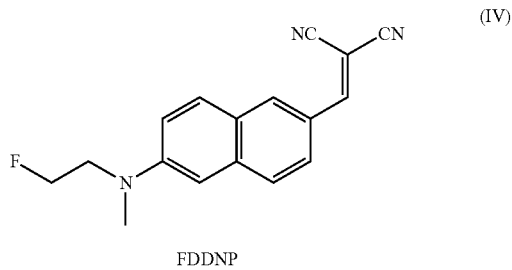

FDDNP (IV)

Thioflavin S, having among the highest sensitivities in detection of senile plaques, is usually used to detect amyloid plaques from the brain tissue of a patient with Alzheimer's disease after death.

In contrast, thioflavin T represented by Chemical Formula III is frequently used as a reagent for studying how the soluble amyloid protein turns into fibrillar aggregates of β sheet structure. Although thioflavin T strongly binds to the β-amyloid plaque, it cannot pass through the blood-brain barrier well when injected into the bloodstream because it exists in the form of an ionic salt.

Recently, electrically neutral derivatives having the 2-arylbenzothiazole structure of thioflavin T but no charge have been developed. These derivatives strongly bind to the β-amyloid plaque and pass through the blood-brain barrier easily. Thereafter, various other analogues having diaryl or conjugated diaryl structures which are characteristic of the 2-arylbenzothiazole were developed by numerous researchers. They were labeled with radioisotopes such as F-18, C-11, I-123, I-125, etc. to detect β-amyloid plaque in vivo and study distribution thereof.

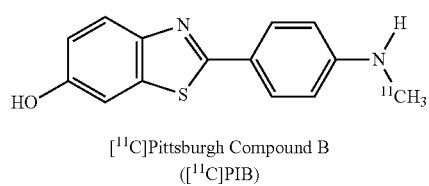

[$^{11}$C]Pittsburgh Compound B
([$^{11}$C]PIB)

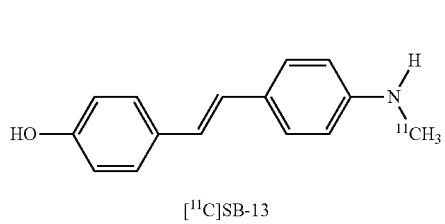

[$^{11}$C]SB-13

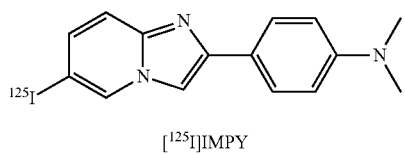

[$^{125}$I]IMPY

[$^{11}$C]PIB (Chemical Formula V, Pittsburgh compound B) is a neutral derivative of the ionic salt thioflavin T. It strongly binds to the β-amyloid plaque and is labeled with C-11 for use as a radiopharmaceutical for positron emission tomography (PET). However, because the half-life of C-11 is only 20 minutes, it is limited in preparation and development of diagnostic reagents. Thus, research is underway into a molecular probe labeled with F-18 (half-life=110 minutes). However, compounds labeled with F-18 tend to have difficulty in passing through the blood-brain barrier because of increased lipophilicity, and it is difficult to obtain clear brain images.

Recently, a stilbene derivative (Chemical Formula VIII, [$^{18}$F]BAY94-9172 or [$^{18}$F]florbetaben) having short-lengthed F-18-containing ethylene glycol has been reported. This stilbene derivative is known to easily pass through the blood-brain barrier because of decreased lipophilicity due to the ethylene glycol group.

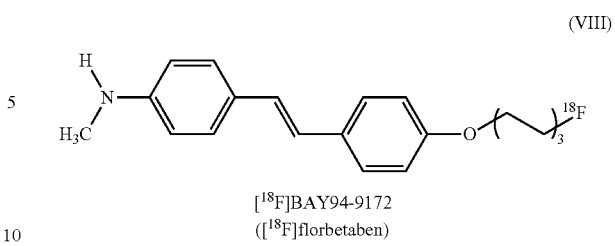

[$^{18}$F]BAY94-9172
([$^{18}$F]florbetaben)

Some of the currently available brain disease-related drugs have inadequate lipophilicity (logP) thus being incapable of passing through the blood-brain barrier. A logP of 2 to 3 enables effective passage through the blood brain barrier. However, F-18-labeled compounds obtained by nucleophilic substitution have increased lipophilicity because of the additionally introduced alkyl groups, and thereby have difficulty in passing through the blood-brain barrier.

The inventors have sought for an F-18-labeled compound capable of solving this problem. They have realized that by introducing a hydroxyl group at an alkyl residue labeled with F-18, a compound may be provided with an adequate logP and be made to pass through the blood-brain barrier easily.

DISCLOSURE

Technical Problem

An aspect of the present disclosure provides aryl derivatives or a pharmaceutically acceptable salt thereof capable of passing through the blood-brain barrier easily.

Another aspect of the present disclosure provides a method for preparing the aryl derivatives.

Another aspect of the present disclosure provides a precursor of the F-18-labeled aryl derivatives.

Another aspect of the present disclosure provides a method for labeling the precursor of the aryl derivatives with F-18.

Another aspect of the present disclosure provides a pharmaceutical composition for the diagnosis or treatment of a degenerative brain disease containing the aryl derivatives or the pharmaceutically acceptable salt thereof as an active ingredient.

Technical Solution

In accordance with an aspect of the present disclosure, there is provided a (3-fluoro-2-hydroxy)propyl-functionalized aryl derivative represented by Chemical Formula 1 or a pharmaceutically acceptable salt thereof:

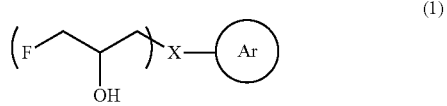

wherein

X and F are the same as defined in Best Mode.

In accordance with another aspect of the present disclosure, there is provided a method for labeling a precursor of the aryl derivative with F-18.

In accordance with another aspect of the present disclosure, there is provided a pharmaceutical composition for the diagnosis or treatment of a degenerative brain disease containing the aryl derivative or the pharmaceutically acceptable salt thereof as an active ingredient.

Advantageous Effects

With the (3-fluoro-2-hydroxy)propyl group introduced, the derivative according to the present disclosure has an increased polarity and thus can easily pass through the blood-brain barrier. Further, since it strongly binds to β-amyloid, it can be used as a diagnostic reagent for detecting Alzheimer's disease early in a noninvasive manner after labeling with an isotope. In addition, since it binds with low molecular weight β-amyloid peptide aggregates and inhibits formation of malignant, high molecular weight β-amyloid plaques, it may be usefully used as a therapeutic agent for a degenerative brain disease such as Alzheimer's disease.

DESCRIPTION OF DRAWINGS

The above and other aspects, features and advantages of the present disclosure will be more clearly understood from the following detailed description taken in conjunction with the accompanying drawings, in which:

FIG. 3 shows a result of chiral HPLC analysis/purification of a compound of Example 4 ((R)-1-2);

FIG. 4 shows a result of chiral HPLC analysis/purification of a compound of Example 7 ((R/S)-1-5);

FIG. 6 shows a result of chiral HPLC analysis/purification of a compound of Example 9 ((R)-1-5);

FIG. 7 shows a result of chiral HPLC analysis/purification of a compound of Example 10 ([$^{18}$F](R/S)-1-2);

FIG. 8 shows a result of HPLC analysis/purification of a compound of Example 11 ([$^{18}$F](R/S)-1-3);

FIG. 9 shows a result of HPLC analysis/purification of a compound of Example 12 ([$^{18}$F](R/S)-1-4);

FIG. 10 shows a result of HPLC analysis/purification of a compound of Example 13 ([$^{18}$F](R/S)-1-5);

FIG. 11 shows a biodistribution curve of the compound of Example 10 ([$^{18}$F](R/S)-1-2) in a rat;

FIG. 12 shows a biodistribution curve of the compound of Example 11 ([$^{18}$F](R/S)-1-3) in a rat;

FIG. 13 shows a biodistribution curve of the compound of Example 12 ([$^{18}$F](R/S)-1-4) in a rat.

BEST MODE

Figure 1:
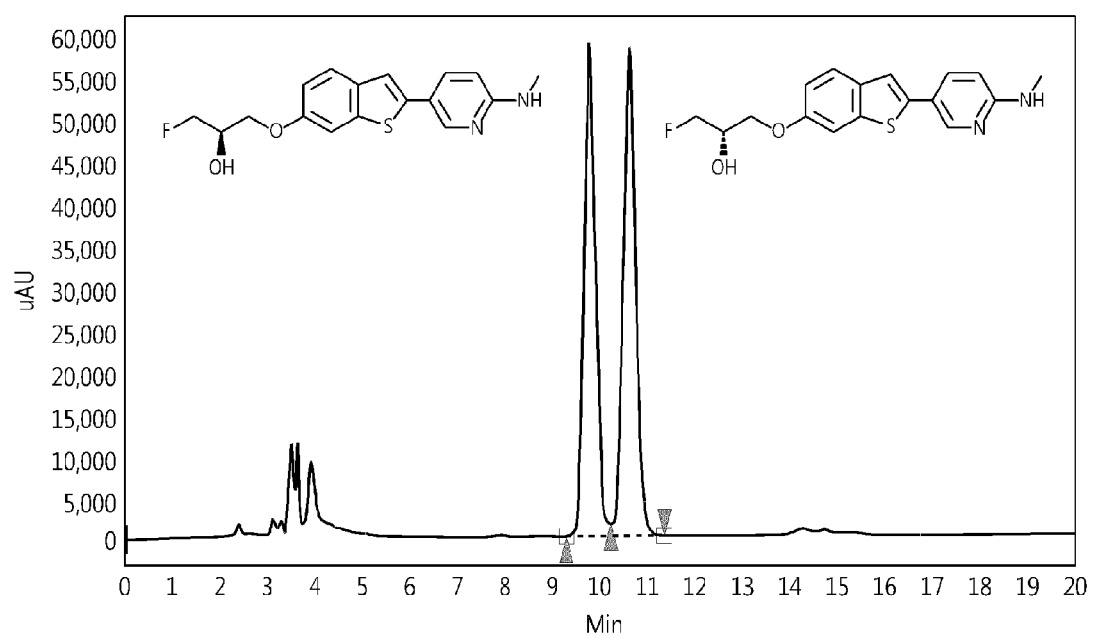
FIG. 1 shows a result of chiral HPLC analysis/purification of a compound of Example 2 ((R/S)-1-2)

Exemplary embodiments of the present disclosure will now be described.

The present disclosure provides (3-fluoro-2-hydroxy)propyl-functionalized aryl derivatives represented by Chemical Formula 1, which are optically active or racemic, or a pharmaceutically acceptable salt thereof:

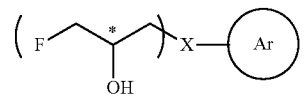 (1)

wherein
F is $^{18}$F or $^{19}$F;
X is O, N or a single bond;

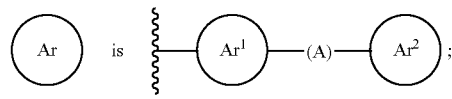

Ar$^1$ and Ar$^2$ are independently C$_{5-12}$ aryl unsubstituted or substituted with one or more

or NR$^1$R$^2$; or C$_{5-12}$ heteroaryl unsubstituted or substituted with one or more

or NR$^1$R$^2$ and containing one or more element(s) selected from a group consisting of O, S and N;
R$^1$ and R$^2$ are independently H or C$_{1-4}$ alkyl;
(A) is

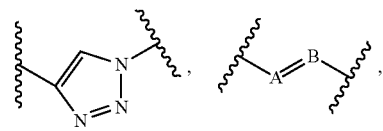

phenyl or a single bond; and
A and B are independently C or N.
Specifically, F may be $^{18}$F or $^{19}$F; X may be O, N or a single bond;

may be

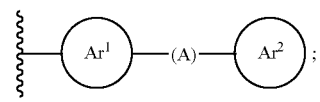

Ar$^1$ and Ar$^2$ may independently be selected from a group consisting of benzothiophene, benzothiazole, benzofuran, indole, benzimidazole, isoindolone, imidazolopyridine, naphthalene, quinoline, quinoxaline, quinazoline, phenyl, pyridine, pyrimidine, pyridazine and pyrazine unsubstituted or substituted with one or more methylamine; (A) may be

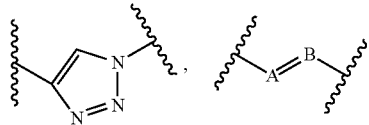

or a single bond; and A and B may independently be C or N.

More specifically, F may be $^{18}F$ or $^{19}F$; X may be O, N or a single bond;

may be

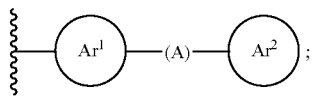

Ar¹ may be selected from a group consisting of

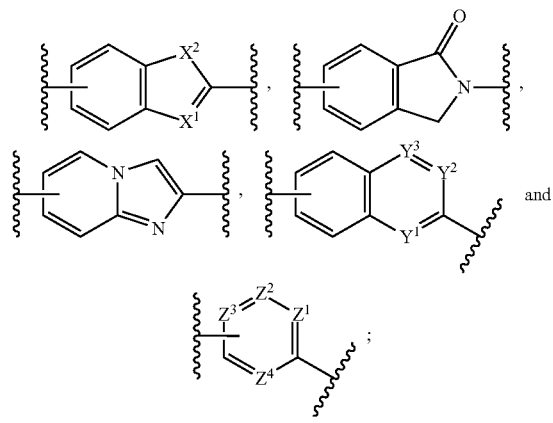

X¹ may be CH or N; X² may be S, O or NH; Y¹, Y² and Y³ may independently be C or N; Z¹, Z², Z³ and Z⁴ may independently be C or N; Ar² may be

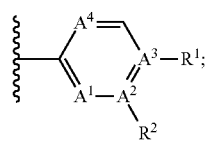

R¹ and R² may independently be H, amine, methylamine or dimethylamine; (A) may be

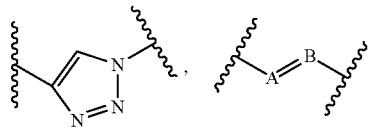

or a single bond; and A and B may independently be C or N.

Specific examples of the novel aryl derivatives represented by Chemical Formula 1 are as follows:

(1) 2-[4-(N-monomethyl)aminophenyl]-6-[(R/S)-3-fluoro-2-hydroxypropoxy]benzothiophene;
(2) 2-[2-(N-monomethyl)aminopyridin-5-yl]-6-[(R/S)-3-fluoro-2-hydroxypropoxy]benzothiophene;
(3) 2-[2-(N-monomethyl)aminopyridin-5-yl]-6-[(S)-3-fluoro-2-hydroxypropoxy]benzothiophene;
(4) 2-[2-(N-monomethyl)aminopyridin-5-yl]-6-[(R)-3-fluoro-2-hydroxypropoxy]benzothiophene;
(5) 2-[4-(N-monomethyl)aminopyridazin-6-yl]-6-[(R/S)-3-fluoro-2-hydroxypropoxy]benzothiophene;
(6) 2-[4-(N-monomethyl)aminophenyl]-6-[(R/S)-3-fluoro-2-hydroxypropoxy]benzothiazole;
(7) 2-[2-(N-monomethyl)aminopyridin-5-yl]-6-[(R/S)-3-fluoro-2-hydroxypropoxy]benzothiazole;
(8) 2-[2-(N-monomethyl)aminopyridin-5-yl]-6-[(S)-3-fluoro-2-hydroxypropoxy]benzothiazole; and
(9) 2-[2-(N-monomethyl)aminopyridin-5-yl]-6-[(R)-3-fluoro-2-hydroxypropoxy]benzothiazole.

The structural formulae of the above compounds are given in Table 1.

TABLE 1

| Compound | Structural formula |
|---|---|
| 1 |  |
| 2 |  |
| 3 |  |
| 4 |  |
| 5 |  |

TABLE 1-continued

| Compound | Structural formula |
|---|---|
| 6 | |
| 7 | |
| 8 | |
| 9 | |

The novel aryl derivatives represented by Chemical Formula 1 may be used in the form of a pharmaceutically acceptable salt. The salt may be an acid addition salt formed from various pharmaceutically or physiologically acceptable organic or inorganic acids. Examples of suitable organic acids include carboxylic acid, phosphonic acid, sulfonic acid, acetic acid, propionic acid, octanoic acid, decanoic acid, glycolic acid, lactic acid, fumaric acid, succinic acid, adipic acid, malic acid, tartaric acid, citric acid, glutamic acid, aspartic acid, maleic acid, benzoic acid, salicylic acid, phthalic acid, phenylacetic acid, benzenesulfonic acid, 2-naphthalenesulfonic acid, methylsulfonic acid, ethylsulfonic acid, dodecylsulfonic acid, or the like. Examples of suitable inorganic acid include hydrochloric acid, sulfuric acid, phosphoric acid, or the like.

In addition to the pharmaceutically acceptable salt, the aryl derivatives according to the present disclosure represented by Chemical Formula 1 may include any salt, hydrate and solvate that may be prepared according to commonly employed methods.

The present disclosure also provides a method for preparing the aryl derivatives represented by Chemical Formula 1.

Specifically, the aryl derivatives according to the present disclosure may be prepared according to Schemes 1 to 3.

Preparation Method 1

As shown in Scheme 1, the aryl derivatives according to the present disclosure may be prepared by:

reacting a compound represented by Chemical Formula 12 in an organic solvent with an allyl compound to prepare a compound represented by Chemical Formula 13 (step 1);

dihydroxylating the resulting compound represented by Chemical Formula 13 in an organic solvent in the presence of an osmium catalyst to prepare a diol derivative represented by Chemical Formula 14 (step 2);

reacting the resulting compound represented by Chemical Formula 14 in an organic solvent with sulfonyl chloride or sulfonic anhydride to prepare a sulfonate derivative represented by Chemical Formula 15 (step 3);

introducing a protecting group at the secondary hydroxyl group of the resulting compound represented by Chemical Formula 15 in an organic solvent in the presence of an acid catalyst to prepare a compound represented by Chemical Formula 16 (step 4);

fluorinating the resulting compound represented by Chemical Formula 16 in an organic solvent (step 5); and deprotecting the resulting fluorinated compound (step 6):

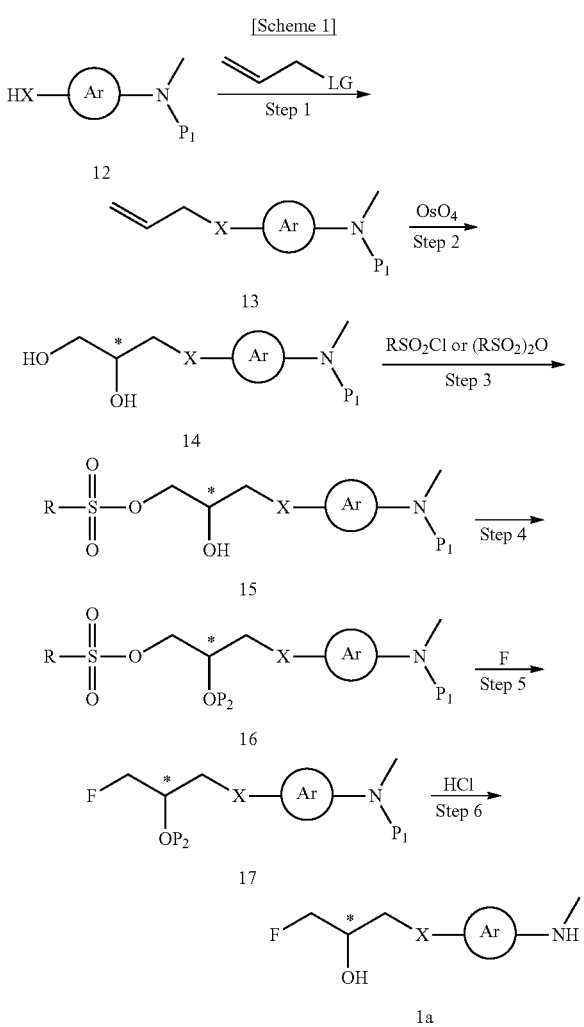

wherein

X and F are the same as defined in Chemical Formula 1,

LG is a leaving group,

R is selected from a group consisting of methyl, trifluoromethyl, p-toluenyl and p-nitrophenyl, $P_1$ is selected from a group consisting of: an amide protecting group such as formyl, acetyl, chloroacetyl, trichloroacetyl, trifluoroacetyl, o-nitrophenylacetyl, o-nitrophenoxyacetyl, acetoacetyl, 3-phenylpropionyl, 3-(p-hydroxyphenyl) propionyl, 2-methyl-2-(o-nitrophenoxy)propionyl, 2-methyl-(o-phenylazophenoxy)propionyl, 4-chlorobutyryl, o-nitrocinnamoyl, picolinoyl, benzoyl or phthalyl; a carbamate protecting group such as methoxycarbonyl, 9-fluorenylmethoxycarbonyl, 2,2,2-trichloroethoxycarbonyl, 1,1-dimethylpropynyloxycarbonyl, 1-methyl-1-phenylethoxycarbonyl, 1-methyl-1-(4-biphenylyl)ethoxycarbonyl, 1,1-dimethyl-2-haloethoxycarbonyl, 1,1-dimethyl-2-cyanoethoxycarbonyl, t-butoxycarbonyl, chlorobutoxycarbonyl, 1-methylcyclobutoxycarbonyl, 1-adamantyloxycarbonyl, vinyloxycarbonyl, allyloxycarbonyl, cinnamyloxycarbonyl, 8-quinolyloxycarbonyl, hydroxypiperidinyloxycarbonyl, benzyloxycarbonyl, p-nitrobenzyloxycarbonyl, 3,4-dimethoxy-6-nitrobenzyloxycarbonyl, 2,4-dichlorobenzyloxycarbonyl, 5-benzoxazolylmethoxycarbonyl, 9-anthrylmethoxycarbonyl, diphenylmethoxycarbonyl or isonicotinyloxycarbonyl; and other protecting groups such as allyl, phenacyl, 3-acetoxypropyl, methoxymethyl, benzyloxymethyl, pivaloyloxymethyl, tetrahydropyranyl, 2,4-dinitrophenyl, benzyl, o-nitrobenzyl, di(p-methoxyphenyl)methyl, triphenylmethyl, (p-methoxyphenyl)diphenylmethyl, diphenyl-4-pyridylmethyl, 2-picolyl N-oxide, benzylidene, p-nitrobenzylidene, salicylidene, 5,5-dimethyl-3-oxo-1-cyclohexenyl, nitro, oxide, diphenylphosphinyl, dimethylthiophosphinyl, benzenesulfenyl, o-nitrobenzenesulfenyl, 2,4,6-trimethylbenzenesulfonyl, toluenesulfonyl, benzylsulfonyl, trifluoromethylsulfonyl or phenacylsulfonyl, $P_2$ is a protecting group selected from a group consisting of $C_{1-6}$ alkyl, methoxymethyl, methylthiomethyl, benzyloxymethyl, p-methoxybenzyloxymethyl, (3,4-dimethoxybenzyloxy)methyl, p-nitrobenzyloxymethyl, 4-methoxyphenoxymethyl, t-butoxymethyl, 2-methoxyethoxymethyl, 2-cyanoethoxymethyl, bis(2-chloroethoxy)methyl, menthoxymethyl, 1,4-dioxan-2-yl, tetrahydropyranyl, tetrahydrothiopyranyl, tetrahydrofuranyl, tetrahydrothiopyranyl, 1-ethoxyethyl, t-butyl, cyclohexyl, 1-(2-cyanoethoxy)ethyl, 2,2,2-trichloroethyl, allyl, benzyl, prenyl, cinnamyl, p-chlorophenyl, p-methoxyphenyl, p-nitrophenyl, 2,4-dinitrophenyl, p-methoxybenzyl, 3,4-dimethoxybenzyl, 2,6-dimethoxybenzyl, o-nitrobenzyl, triphenylmethyl and p-methoxyphenyldiphenylmethyl, and Chemical Formula 1a is included in Chemical Formula 1.

In step 1, the aryl derivative represented by Chemical Formula 12 is reacted in an organic solvent in the presence of a base with an allyl compound to prepare the compound represented by Chemical Formula 13. The aryl derivative represented by Chemical Formula 12 may be purchased commercially, synthesized using known reactions or synthesized according to the method described in the example section of the present disclosure. The base may be sodium hydride (NaH), potassium carbonate ($K_2CO_3$), cesium carbonate ($Cs_2CO_3$), or the like. Specifically, cesium carbonate may be used. The organic solvent may be tetrahydrofuran (THF), acetone, acetonitrile, dimethylformamide (DMF), dimethyl sulfoxide (DMSO), or the like. Specifically, dimethylformamide may be used. The allyl compound may be allyl chloride, allyl bromide, allyl sulfonate, or the like. Specifically, allyl bromide may be used.

For example, the allyl-substituted aryl compound represented by Chemical Formula 13 may be prepared by dissolving the aryl derivative represented by Chemical Formula 12 and cesium carbonate in dimethylformamide, adding allyl bromide thereto, and agitating the mixture at room temperature to 80° C. for 30 minutes to 3 hours.

If X is NH, after the introduction of the aryl group as described above, a protecting group $P_1$ may be introduced. Here, $P_1$ is the same as defined in Scheme 1.

In step 2, the aryl compound represented by Chemical Formula 13 obtained in step 1 is dihydroxylated in an organic solvent in the presence of an osmium catalyst to prepare a diol derivative. The organic solvent may be t-butanol, dichloromethane, tetrahydrofuran, acetone, acetonitrile, dimethylformamide, dimethyl sulfoxide, water or a mixture thereof. Specifically, a tetrahydrofuran/water mixture may be used. The catalyst may be osmium oxide ($OsO_4$(VIII)), potassium osmate ($K_2OsO_4$(VI)), or the like. Specifically, potassium osmate may be used. As a co-oxidant, N-methylmorpholine N-oxide (NMO), potassium ferricyanide ($K_3Fe(CN)_6$), oxone, ammonium cerium(IV) sulfate ($Ce(NH_4)_4(SO_4)_4$), or the like may be used. Specifically, potassium ferricyanide may be used. As a tertiary amine ligand, 1,4-diazabicyclo[2.2.2]octane (DABCO) or an alkaloid such as cinchonide may be used. Specifically, if the compound represented by Chemical Formula 13 is a racemate, DABCO may be used. Additionally, if it is an optically active compound, a cinchonide alkaloid may be used. Additionally, if potassium osmate is used as the catalyst, potassium carbonate may also be included.

AD-mix α or AD-mix β developed for effective asymmetric dihydroxylation may be used in step 2 of Scheme 1.

Specifically, the allyl derivative represented by Chemical Formula 13 obtained in step 1 may be dissolved in a tetrahydrofuran/water (4/1) mixture and, after adding AD-mix α or AD-mix β, the mixture may be agitated at room temperature for 3 to 48 hours to obtain the diol derivative represented by Chemical Formula 14.

In step 3, the diol compound represented by Chemical Formula 14 obtained in step 2 is reacted in an organic solvent with sulfonyl chloride or sulfonic anhydride to prepare a sulfonate derivative. The organic solvent may be dichloromethane, tetrahydrofuran, pyridine, or the like. Specifically, dichloromethane may be used. The base may be triethylamine, diisopropylethylamine (DIEA), 2,6-lutidine, collidine, 4-(dimethylamino)pyridine (DMAP), 1,5-diazabicyclo[4.3.0]non-5-ene (DBN), 1,8-diazabicyclo[5.4.0]undec-7-ene (DBU), or the like. Specifically, triethylamine may be used. The sulfonyl reagent may be methanesulfonyl chloride ($CH_3SO_2Cl$), p-toluenesulfonyl chloride (p-$CH_3C_6H_4SO_2Cl$), p-nitrobenzenesulfonyl chloride (p-$NO_2C_6H_4SO_2Cl$), polyethylene glycol sulfonyl chloride ($CH_3O(CH_2CH_2O)_nCH_2CH_2SO_2Cl$), polystyrene sulfonyl chloride, anhydrides thereof, anhydrous trifluoromethanesulfonate ($(CF_3SO_2)O$), or the like. Specifically, methanesulfonyl chloride may be used.

Specifically, the sulfonate derivatives represented by Chemical Formula 15 may be obtained by dissolving the diol compound represented by Chemical Formula 14 obtained in step 2 in dichloromethane, sequentially adding methanesulfonyl chloride and triethylamine after cooling to 0° C., and agitating the mixture at 0° C. for about 30 minutes.

In step 4, a protecting group is introduced at the secondary hydroxyl group of the sulfonate compound represented by Chemical Formula 15 obtained in step 3 in organic solvent in the presence of an acid catalyst. The solvent may be dichloromethane, benzene, toluene, tetrahydrofuran, or the like. Specifically, tetrahydrofuran may be used. The protecting group $P_2$ may be the same as defined in Scheme 1. Specifically, 3,4-dihydro-2H-pyran (DHP) may be used. The acid catalyst may be pyridinium p-toluenesulfonate (PPTS), p-toluenesulfonic acid (TsOH), a Lewis acid, or the like. Specifically, pyridinium p-toluenesulfonate may be used.

Specifically, the sulfonate derivatives represented by Chemical Formula 16 with a 3,4,5,6-tetrahydro-2H-pyranyl (THP) protecting group introduced may be prepared by dissolving the sulfonate compound represented by Chemical Formula 15 obtained in step 3 and pyridinium p-toluenesulfonate in dichloromethane, adding DHP, and agitating the mixture at room temperature for about 3 hours.

In step 5, the sulfonate compound represented by Chemical Formula 16 obtained in step 4 is fluorinated in an organic solvent. The organic solvent may be acetonitrile, dimethylformamide, dimethyl sulfoxide, a tertiary alcohol such as t-butanol and t-amyl alcohol, or the like. Specifically, t-amyl alcohol may be used. A fluoride reagent such as cesium fluoride (CsF), tetrabutylammonium fluoride (TBAF), or the like may be used. Specifically, tetrabutylammonium fluoride may be used.

Specifically, the fluoro derivatives represented by Chemical Formula 17 may be prepared by dissolving the sulfonate compound represented by Chemical Formula 16 obtained in step 4 and tetrabutylammonium fluoride in t-amyl alcohol and heating to 100~120° C. for 30 minutes to 3 hours.

In step 6, the fluoro compound represented by Chemical Formula 17 obtained in step 5 is deprotected in an organic solvent to obtain the compound represented by Chemical Formula 1 (1a). The reaction solvent may be methanol, tetrahydrofuran, dichloromethane, acetonitrile, or the like. Specifically, a tetrahydrofuran/methanol mixture may be used. The acid catalyst may be an aqueous solution of a Brønsted acid or a Lewis acid in aqueous solution. Specifically, a 2 N HCl aqueous solution may be used.

Specifically, the compound represented by Chemical Formula 1 may be prepared by dissolving the fluorinated compound represented by Chemical Formula 17 obtained in step 5 in a tetrahydrofuran/methanol mixture, adding 2 N HCl, and then heating to 60 to 80° C. for 30 minutes to 3 hours.

The preparation method according to Scheme 1 may further comprise a step of substituting the (3-fluoro-2-hydroxy)propoxy-functionalized or N-(3-fluoro-2-hydroxypropyl) amino group-functionalized aryl derivative with another substituent. Further substitution may be performed according to commonly employed methods.

Preparation Method 2

As shown in Scheme 2, the aryl derivatives according to the present disclosure may be prepared by:

reacting an aryl derivative represented by Chemical Formula 12 with a (2,2-dimethyl-1,3-dioxolan-4-yl)methyl derivative represented by Chemical Formula 18 in an organic solvent in the presence of a base to prepare a compound represented by Chemical Formula 19 (step 1');

removing the ketal protecting group of the resulting compound represented by Chemical Formula 19 in an organic solvent in the presence of an acid catalyst to prepare a compound represented by Chemical Formula 14 (step 2');

reacting the resulting compound represented by Chemical Formula 14 in an organic solvent with sulfonyl chloride or sulfonic anhydride to prepare sulfonate derivatives represented by Chemical Formula 15 (step 3);

introducing a protecting group at the secondary hydroxyl group of the resulting compound represented by Chemical Formula 15 in an organic solvent in the presence of an acid catalyst to prepare a compound represented by Chemical Formula 16 (step 4);

fluorinating the resulting compound represented by Chemical Formula 16 in an organic solvent (step 5); and deprotecting the resulting fluorinated compound (step 6):

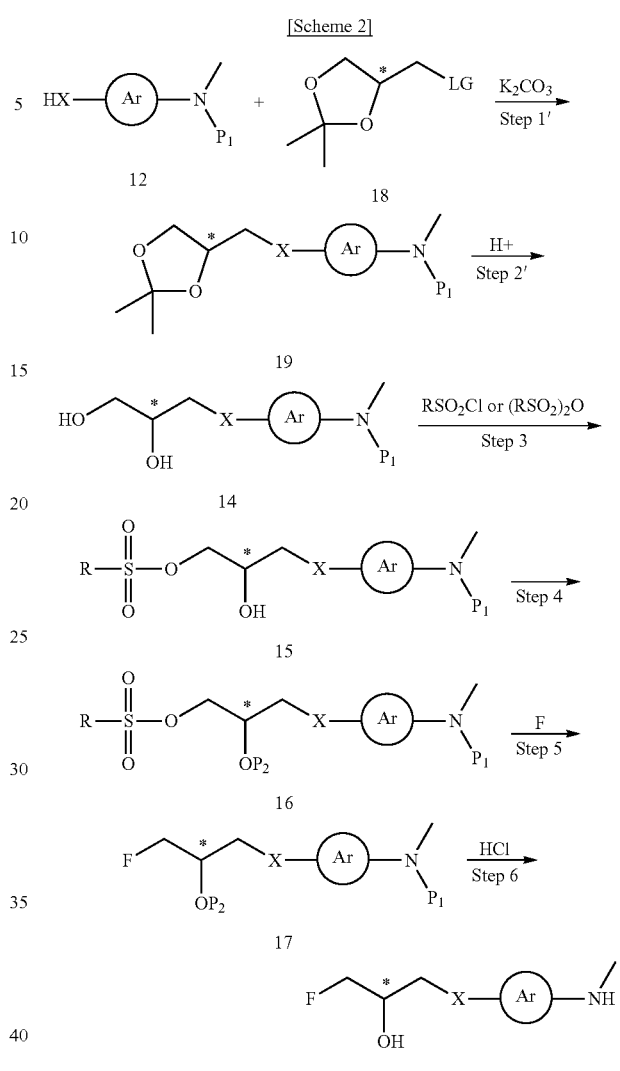

wherein

F and X are the same as defined in Chemical Formula 1, LG, R, $P_1$ and $P_2$ are the same as defined in Scheme 1, and Chemical Formula 1a is included in Chemical Formula 1 of claim 1.

In step 1', the aryl derivative represented by Chemical Formula 12 is reacted with the (2,2-dimethyl-1,3-dioxolan-4-yl)methyl derivative represented by Chemical Formula 18 in an organic solvent in the presence of a base to obtain the compound represented by Chemical Formula 19. The base may be sodium hydride (NaH), potassium carbonate ($K_2CO_3$), cesium carbonate ($Cs_2CO_3$), or the like. Specifically, cesium carbonate may be used. The organic solvent may be tetrahydrofuran, acetone, acetonitrile, dimethylformamide, dimethyl sulfoxide, or the like. Specifically, dimethylformamide may be used. The (2,2-dimethyl-1,3-dioxolan-4-yl)methyl derivatives may be (2,2-dimethyl-1,3-dioxolan-4-yl)methyl chloride, (2,2-dimethyl-1,3-dioxolan-4-yl)

methyl bromide, (2,2-dimethyl-1,3-dioxolan-4-yl)methyl sulfonate, or the like. Specifically, (2,2-dimethyl-1,3-dioxolan-4-yl)methyl sulfonate may be used. When optically active (R)-(2,2-dimethyl-1,3-dioxolan-4-yl)methyl sulfonate or (S)-(2,2-dimethyl-1,3-dioxolan-4-yl)methyl sulfonate is used, the resulting aryl compound represented by Chemical Formula 19 may be optically pure.

Specifically, the aryl compound represented by Chemical Formula 13 may be obtained by dissolving the aryl derivatives represented by Chemical Formula 12 and cesium carbonate in dimethylformamide, adding (2,2-dimethyl-1,3-dioxolan-4-yl)methyl sulfonate, and agitating at room temperature to 80° C. for 30 minutes to 3 hours.

If X is NH, after the addition of the aryl group as described above, a protecting group $P_1$ may be introduced. Here, $P_1$ is the same as defined in Scheme 1.

In step 2', the aryl compound represented by Chemical Formula 19 obtained in step 1 is reacted in an organic solvent in the presence of an acid catalyst to remove the ketal protecting group. The organic solvent may be tetrahydrofuran, dichloromethane, acetonitrile, dimethylformamide, dimethylacetamide, dimethyl sulfoxide, methanol, ethanol, water or a mixture thereof. Specifically, a methanol/water mixture may be used. The catalyst may be a Brønsted acid, a Lewis acid, a resin, or the like. Specifically, Dowex 50WX2 (strong acid) may be used.

Specifically, the diol derivative represented by Chemical Formula 14 may be obtained by dissolving the aryl compound represented by Chemical Formula 19 obtained in step 1' in methanol, adding water and then Dowex 50WX2, and agitating at room temperature to 60° C. for 3 to 24 hours.

The following steps 3 to 6 may be performed in the same manner as described in Scheme 1.

Preparation Method 3

As shown in Scheme 3, the aryl derivatives according to the present disclosure may be prepared by:

reacting an aryl derivative represented by Chemical Formula 12 with a 2-oxiranylmethyl derivative represented by Chemical Formula 20 in an organic solvent in the presence of a base to prepare a compound represented by Chemical Formula 21 (step 1");

opening the epoxide ring of the resulting aryl compound represented by Chemical Formula 21 in an organic solvent under acidic or basic conditions to prepare a compound represented by Chemical Formula 14 (step 2");

reacting the resulting compound represented by Chemical Formula 14 in an organic solvent with sulfonyl chloride or sulfonic anhydride to prepare a sulfonate derivative represented by Chemical Formula 15 (step 3);

introducing a protecting group at the secondary hydroxyl group of the resulting compound represented by Chemical Formula 15 in an organic solvent in the presence of an acid catalyst to prepare a compound represented by Chemical Formula 16 (step 4);

fluorinating the resulting compound represented by Chemical Formula 16 in an organic solvent (step 5); and deprotecting the resulting fluorinated compound (step 6):

[Scheme 3]

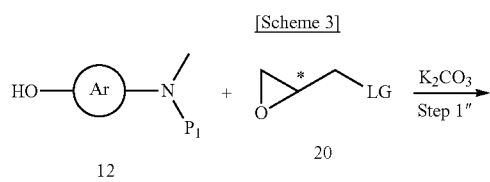

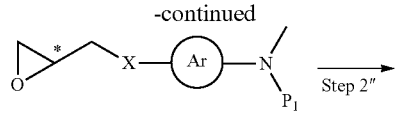

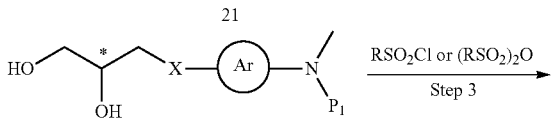

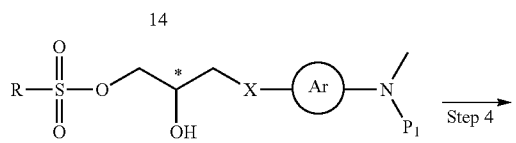

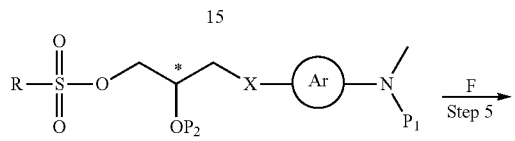

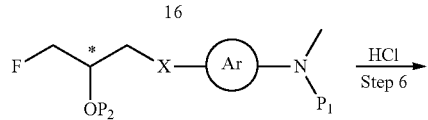

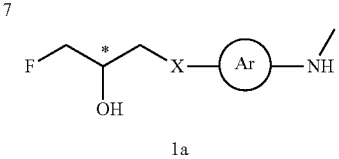

wherein

F and X are the same as defined in Chemical Formula 1, LG, R, $P_1$ and $P_2$ are the same as defined in Scheme 1, and Chemical Formula 1a is included in Chemical Formula 1.

In step 1", the aryl derivative represented by Chemical Formula 12 is reacted with the 2-oxiranylmethyl-derivative represented by Chemical Formula 20 in an organic solvent in the presence of a base to obtain the compound represented by Chemical Formula 21. The base may be sodium hydride (NaH), potassium carbonate ($K_2CO_3$), cesium carbonate ($Cs_2CO_3$), or the like. Specifically, cesium carbonate may be used. The organic solvent may be tetrahydrofuran, acetone, acetonitrile, dimethylformamide, dimethyl sulfoxide, or the like. Specifically, dimethylformamide may be used. The 2-oxiranylmethyl derivative may be 2-oxiranylmethyl chloride (epichlorohydrin), 2-oxiranylmethyl bromide (epibromohydrin), 2-oxiranylmethyl sulfonate, or the like. Specifically, 2-oxiranylmethyl chloride may be used. When optically active (R)-2-oxiranylmethyl sulfonate or (S)-2-oxiranylmethyl sulfonate is used, the resulting aryl compound represented by Chemical Formula 21 may be optically pure.

Specifically, the aryl compound represented by Chemical Formula 21 may be obtained by dissolving the aryl derivative represented by Chemical Formula 12 and cesium carbonate in dimethylformamide, adding 2-oxiranylmethyl chloride, and agitating the mixture at room temperature to 80° C. for 30 minutes to 3 hours.

If X is NH, after the addition of the 2-oxiranylmethyl group as described above, a protecting group $P_1$ may be introduced. Here, $P_1$ is the same as defined in Scheme 3.

In step 2", the epoxide ring of the aryl compound represented by Chemical Formula 21 obtained in step 1" is opened in an organic solvent under an acidic or basic condition. The organic solvent may be tetrahydrofuran, dichloromethane, acetonitrile, dimethylformamide, dimethylacetamide, dimethyl sulfoxide, methanol, ethanol, water or a mixture thereof. Specifically, a tetrahydrofuran/water mixture may be used. An acid catalyst such as a Brønsted acid, a Lewis acid, a resin, or the like may be used. Specifically, a 4 M sulfuric acid aqueous solution may be used.

Specifically, the diol derivative represented by Chemical Formula 14 may be obtained by dissolving the aryl compound represented by Chemical Formula 21 obtained in step 1" in tetrahydrofuran, adding water and then aqueous 4 M sulfuric acid, and agitating at room temperature to 60° C. for 3 to 24 hours.

Also, the epoxide ring of the aryl compound represented by Chemical Formula 21 obtained in step 1" may be opened under basic conditions. In this case, the organic solvent includes tetrahydrofuran, dichloromethane, acetonitrile, dimethylformamide, dimethylacetamide, dimethyl sulfoxide, methanol, ethanol, water or a mixture thereof. Specifically, a dimethyl sulfoxide/water mixture may be used. A base such as NaOH, KOH, KOAc/KOH, TBAOH, or the like may be used. Specifically, a KOAc/KOH mixture may be used.

Specifically, the diol derivative represented by Chemical Formula 14 may be obtained by adding dimethyl sulfoxide to a reactor containing the aryl compound represented by Chemical Formula 21 obtained in step 1" and potassium acetate (KOAc), agitating at room temperature for about 30 minutes to 12 hours, adding 0.2 M aqueous potassium hydroxide, and then agitating at room temperature for 30 minutes to 3 hours.

If the aryl compound is optically pure, the 1,2-diol compound obtained by using the base in step 1" of Scheme 3 may retain optical activity.

Further, the present disclosure provides a precursor of the aryl derivative or the pharmaceutically acceptable salt thereof for labeling with $^{18}$F, which is represented by Chemical Formula 16:

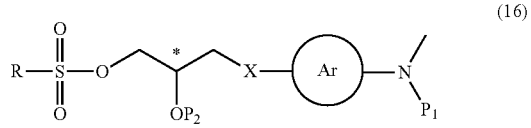

(16)

wherein

and X are the same as defined in Chemical Formula 1 and R, $P_1$ and $P_2$ are the same as defined in Scheme 1.

The precursor according to the present disclosure may be prepared as described in Scheme 1.

The precursor of the aryl derivative according to the present disclosure may be labeled with $^{18}$F as described in steps 5 and 6 of Scheme 1. The labeling may be performed in various ways with or without using a polymer cartridge.

If a polymer cartridge is used, a [$^{18}$F]fluoride/[$^{18}$O]H$_2$O aqueous solution produced in a cyclotron is passed through a Chromafix or quaternary alkylammonium (QMA) cartridge to capture [$^{18}$F]fluoride in the cartridge while removing water using methanol. Then, a methanol solution containing TBAHCO$_3$ or TBAOMs is flown to the cartridge to elute the [$^{18}$F]fluoride captured in the cartridge. Then, water and methanol are completely removed by heating at 100~120° C. for 1-3 minutes while passing nitrogen gas over the solution. Thus prepared precursor compound represented by Chemical Formula 16 for labeling with $^{18}$F is added to a reactor and then dissolved by adding a reaction solvent. After heating the resulting reaction mixture at 100~130° C. for 3~30 minutes, the solvent is removed at the same temperature while passing nitrogen gas over the reaction mixture. Then, acetonitrile is added to the residue to dissolve the remaining compound. After adding 1 N HCl and heating at 50~100° C. for 2~10 minutes and cooling to room temperature, the mixture is neutralized with 1 N aqueous sodium bicarbonate. After adding distilled water to the neutralized mixture, the resulting reaction mixture is passed through a C-18 cartridge (SepPak) and washed with distilled water. After eluting the compound remaining in the C-18 cartridge using acetonitrile, a portion or all thereof may be subjected to high-performance liquid chromatography (HPLC) to separate the $^{18}$F-labeled compound.

In case a polymer cartridge is not used, a [$^{18}$F]fluoride/[$^{18}$O]H$_2$O aqueous solution produced is added to a reactor. Then, after adding TBAHCO$_3$ or TBAOH, water is completely removed by adding acetonitrile and heating at 100~120° C. while passing nitrogen gas over the solution. The procedure of adding and then removing acetonitrile is repeated 3-4 times until water is completely removed. Thus the prepared precursor compound represented by Chemical Formula 16 for labeling with $^{18}$F is added to a reactor and then dissolved by adding a reaction solvent. After heating the resulting reaction mixture at 100~130° C. for 3~30 minutes, the solvent is removed at the same temperature while passing nitrogen gas over the reaction mixture. Then, acetonitrile is added to the residue with the solvent removed to dissolve the remaining compound. After adding 1 N HCl and heating at 50~100° C. for 2~10 minutes and cooling to room temperature, the mixture is neutralized with 1 N sodium bicarbonate aqueous solution. After adding distilled water to the neutralized mixture, the resulting reaction mixture is passed through a C-18 cartridge (SepPak) and washed with distilled water. After eluting the compound remaining in the C-18 cartridge by flowing acetonitrile, a portion or all thereof may be subjected to HPLC to separate the $^{18}$F-labeled compound.

The present disclosure further provides a pharmaceutical composition for the diagnosis or treatment of a degenerative brain disease containing the aryl derivative represented by Chemical Formula 1 or a pharmaceutically acceptable salt thereof as an active ingredient.

The degenerative brain disease may be Alzheimer's disease.

Alzheimer's disease (AD) is the most common form of dementia and is usually diagnosed clinically based on pathological features. Pathologically, various morphological changes are observed. The two most important morphological changes are senile plaques and neurofibrillary degeneration widely distributed in the neocortex. The neurofibrillary degeneration is observed as neurofibrillary tangles and neuropil threads resulting from abnormally phosphorylated tau filaments twisted in pairs. The senile plaque consists of amyloid. The deposition of amyloid beta (Aβ) plays a critical role in Alzheimer's disease. A large amount of experimental evidence supports the theory that aggregated β-amyloid proteins, comprising the majority of senile plaques, are the major cause of Alzheimer's disease.

β-Amyloid is a metabolite of a type I integral membrane protein called the amyloid precursor protein (APP) by a protease. It is a peptide of 39-43 amino acids consisting of an extracellular domain and a membrane domain. According to the generally accepted hypothesis, Aβ induces death of neurons as follows. As APP is fragmented by gradual proteolysis to form Aβ, Aβ forms aggregates in to clumps, thereby producing β-sheets. As they are further aggregated, the senile plaques are formed and the neurons eventually die. Therefore, if β-amyloid can be detected before the senile plaques or neurofibrillary tangles are formed, Alzheimer's disease may be diagnosed earlier.

According to an experiment carried out to test the binding ability of the aryl derivative represented by Chemical Formula 1 of the present disclosure to the β-amyloid peptide, the compounds of the present disclosure exhibit stronger binding affinity ($K_i$) to β-amyloid than the [$^{11}$C]PIB compound, as shown in Table 2. Especially, the compounds of Examples 1, 2, 5 and 6 show superior binding affinity of 1.20 nM, 0.49 nM, 0.42 nM and 1.06 nM, respectively. In particular, the derivatives of the present disclosure have such an excellent binding ability to β-amyloid as to inhibit the binding of [$^{125}$I]TZDM (48), which is known to have a strong binding ability to the β-amyloid peptide.

Additionally, according to an experiment carried out to study the in vivo distribution of the aryl derivative represented by Chemical Formula 1 labeled with F-18, as shown in Table 3, the aryl derivative according to the present disclosure with a hydroxyl group introduced at the propyl residue exhibits a very large initial inflow rate to the brain and a good penetration rate through the blood-brain barrier.

Accordingly, the aryl derivative represented by Chemical Formula 1 of the present disclosure may be usefully used as an agent for preventing or treating Alzheimer's disease induced by β-amyloid. Furthermore, the aryl derivative represented by Chemical Formula 1 of the present disclosure, labeled with a radioactive isotope such as $^{18}$F or $^{11}$C, may be used as a radiopharmaceutical for scientific diagnosis of Alzheimer's disease.

The aryl derivative represented by Chemical Formula 1 or the pharmaceutically acceptable salt thereof may be administered orally or parenterally in the form of various formulations for clinical purposes. Such formulations are usually prepared using a commonly employed diluent or excipient, such as a filler, a thickening agent, a binder, a wetting agent, a disintegrant, a surfactant, etc.

Solid preparations intended for oral administration may take the form of tablets, pills, powders, granules, capsules, troches, and the like. These solid preparations may be formulated, in addition to one or more of the aryl derivative(s) represented by Chemical Formula 1 or the pharmaceutically acceptable salt(s) thereof, in combination with at least one excipient such as, starch, calcium carbonate, sucrose, lactose or gelatin. In addition, a lubricant such as magnesium stearate, talc, or the like may be used. Liquid preparations intended for oral administration may include suspensions, liquid agents for internal use, emulsions, syrups, or the like. In addition to a simple diluent such as water or liquid paraffin, various excipients, such as wetting agents, sweeteners, aromatics, preservatives, or the like may be included.

Preparations for parenteral administration may include sterilized aqueous solutions, non-aqueous solvents, suspensions, emulsions, lyophilizates, suppositories, and the like. Injectable propylene glycol, polyethylene glycol, vegetable oils such as olive oil, esters such as ethyl oleate, or the like may be suitable for non-aqueous solvents and suspensions. The basic materials of suppositories may include Witepsol, macrogol, Tween 61, cacao butter, laurin butter, glycerol, gelatin, and the like.

An administration dose of the aryl derivative represented by Chemical Formula 1 or the pharmaceutically acceptable salt thereof for a human patient will depend on age, weight, sex and physical condition of the patient, route of administration and severity of the disease. For an adult patient weighing 70 kg, a typical dose may be 0.1 to 1000 mg/day, specifically 1 to 500 mg/day, administered in a single dose or divided into several doses per day according to the instructions of a physician or a pharmacist.

MODE FOR INVENTION

Next, examples of the present disclosure will be described in detail. However, it will be apparent to those skilled in the art that the present disclosure is not limited to these examples disclosed below but can be implemented in various ways.

Preparation Example 1

Preparation of 2-[4-(N-methyl-N—BOC)aminophenyl]-6-hydroxybenzothiophene

Step 1: Preparation of 6-(t-butyldimethylsilyloxy)benzothiophene-2-boronic acid

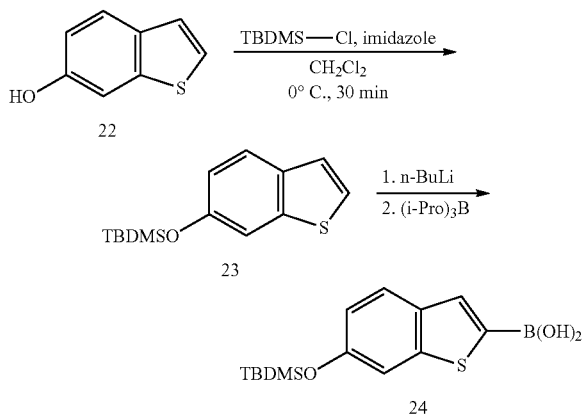

6-Hydroxybenzothiophene (22, 8.55 g, 56.9 mmol) and imidazole (4.65 g, 68.3 mmol) were dissolved in dichloromethane (120 mL) and TBDMS-Cl (9.73 g, 62.6 mmol) dissolved in dichloromethane (50 mL) was slowly added at 0° C. The reaction mixture was agitated at 0° C. for 1 hour. After adding water and transferring the resulting solution to a separatory funnel, the dichloromethane layer was separated. The remaining organic compound was extracted three times with dichloromethane. After removing water using sodium sulfate, the solvent was removed under reduced pressure. Column chromatography yielded 6-(t-butyldimethylsilyloxy)benzothiophene (23, 13.6 g, 90%) as a liquid.

$^1$H NMR (400 MHz, CDCl$_3$) δ 0.26 (s, 6H), 1.05 (s, 9H), 6.94 (dd, J=8.4, 1.6 Hz, 1H), 7.27 (d, J=5.6 Hz, 1H), 7.30 (d, J=5.6 Hz), 7.35 (d, J=2.0 Hz, 1H), 7.69 (d, J=8.4 Hz);

$^{13}$C NMR (100 MHz, CDCl$_3$) δ −4.4, 18.2, 25.7, 112.6, 118.6, 123.4, 123.9, 124.0, 134.1, 140.9, 153.0.

2.5 M n-butyllithium (23 mL, 57.5 mmol) in hexane was slowly added to the 6-(t-butyldimethylsilyloxy)benzothiophene (23, 13.6 g, 51.0 mmol) dissolved in anhydrous tetrahydrofuran (150 mL) at −78° C. under nitrogen atmosphere. 15 minutes later, the mixture was agitated at room temperature for 1 hour. After cooling again to −78° C., triisopropyl borate ((i-PrO)$_3$B; 14.0 mL, 62.0 mmol) was slowly added. Then, after slowly heating to room temperature and agitating for 3 hours, water was added to quench the reaction. After extracting the organic compound with ethyl acetate and removing water using sodium sulfate, column chromatography yielded the target compound 6-(t-butyldimethylsilyloxy)benzothiophene-2-boronic acid (24, 9.75 g, 62%).

$^1$H NMR (400 MHz, DMSO-d$_6$) δ 0.22 (s, 6H), 0.97 (s, 9H), 6.91 (dd, J=8.4, 2.0 Hz, 1H), 7.43 (d, J=2.0 Hz, 1H), 7.76 (s, 1H), 7.80 (d, J=8.4 Hz, 1H);

$^{13}$C NMR (100 MHz, DMSO-d$_6$) δ −4.5, 18.0, 25.6, 112.1, 118.3, 124.7, 130.7, 132.5, 135.5, 144.2, 153.1.

Step 2: Preparation of 2-[4-(N-methyl-N—BOC)aminophenyl]-6-(t-butyldimethylsilyloxy)benzothiophene

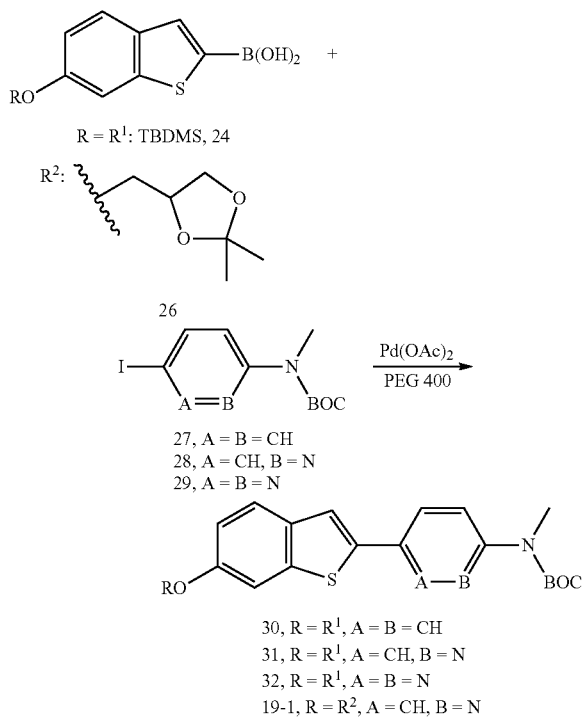

6-(t-Butyldimethylsilyloxy)benzothiophene-2-boronic acid (24, 300 mg, 0.973 mmol) obtained in step 1 was dissolved in PEG 400 (7 mL) and slowly added to 4-(N-methyl-N—BOC)amino-1-iodobenzene (27, 295 mg, 0.885 mmol), K$_2$CO$_3$ (207 mg, 1.459 mmol) and Pd(OAc)$_2$ (5 mg, 0.020 mmol) dissolved in PEG 400 (7 mL) at room temperature. After agitating the reaction mixture at room temperature for 3 hours and adding water, the organic compound was extracted with ethyl acetate. After treating the collected ethyl acetate solution with sodium sulfate, column chromatography yielded the target compound 2-[4-(N-methyl-N—BOC)-aminophenyl]-6-(t-butyldimethylsilyloxy)benzothiophene (30, 255 mg, 71%).

$^1$H NMR (400 MHz, CDCl$_3$) δ 0.01 (s, 6H), 0.78 (s, 9H), 1.23 (s, 9H), 3.06 (s, 3H), 6.66 (dd, J=8.4, 2.0 Hz, 1H), 7.03 (d, J=3.2 Hz, 1H), 7.04 (d, J=9.2 Hz, 2H), 7.37 (d, J=8.4 Hz, 1H), 7.38 (d, J=8.4 Hz, 2H);

$^{13}$C NMR (100 MHz, CDCl$_3$) δ −4.4, 18.2, 25.7, 28.3, 29.7, 37.1, 112.5, 118.6, 118.9, 124.0, 125.6, 126.3, 131.4, 135.3, 140.7, 141.4, 143.4, 153.2, 154.6.

Step 3: Preparation of 2-[4-(N-methyl-N—BOC)aminophenyl]-6-hydroxybenzothiophene

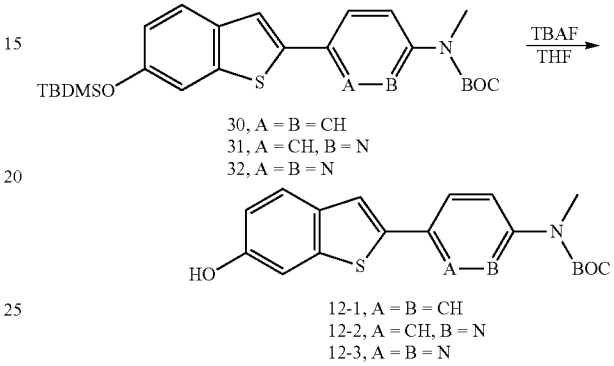

2-[4-(N-Methyl-N—BOC)aminophenyl]-6-(t-butyldimethylsilyloxy)benzothiophene (30, 377 mg, 0.717 mmol) obtained in step 2 and tetrabutylammonium fluoride (TBAF; 188 mg, 0.717 mmol) were dissolved in tetrahydrofuran. After agitating at room temperature for 30 minutes, water was added. The resulting product was extracted with ethyl acetate and water was removed using sodium sulfate. Column chromatography yielded the target compound 2-[4-(N-methyl-N—BOC)aminophenyl]-6-hydroxybenzothiophene (12-1, 232 mg, 91%).

$^1$H NMR (400 MHz, CDCl$_3$) δ 1.48 (s, 9H), 3.28 (s, 3H), 6.90 (dd, J=8.4, 2.0 Hz, 1H), 7.23-7.30 (m, 3H), 7.39 (s, 1H), 7.56-7.61 (m, 3H);

$^{13}$C NMR (100 MHz, CDCl$_3$) δ 28.2, 37.1, 107.3, 114.5, 118.9, 124.1, 125.7, 126.1, 131.7, 134.0, 140.0, 140.9, 142.9, 154.4.

Preparation Example 2

Preparation of 2-[2-(N-methyl-N—BOC)aminopyridin-5-yl]-6-hydroxybenzothiophene

Step 1: Preparation of 6-(t-butyldimethylsilyloxy)benzothiophene-2-boronic acid 6-(t-Butyldimethylsilyloxy)benzothiophene-2-boronic acid (24) was prepared in the same manner as step 1 of Preparation Example 1.

Step 2: Preparation of 2-[2-(N-methyl-N—BOC)aminopyridin-5-yl]-6-(t-butyldimethylsilyloxy)benzothiophene 6-(t-Butyldimethylsilyloxy)benzothiophene-2-boronic acid (24, 300 mg, 0.973 mmol) obtained in step 1 dissolved in PEG 400 (5 mL) was slowly added to 2-(N-methyl-N—BOC)amino-5-iodopyridine (28, 358 mg, 1.070 mmol), K$_2$CO$_3$ (202 mg, 1.459 mmol) and Pd(OAc)$_2$ (4.4 mg, 0.02 mmol) dissolved in PEG 400 (5 mL) at room temperature. After agitating the reaction mixture at room temperature for 3 hours and adding water, the organic compound was extracted with ethyl acetate. After treating the collected ethyl acetate solution with sodium sulfate, column chromatography yielded the target compound 2-[4-(N-methyl-N—BOC)aminopyridin-5-yl]-6-(t-butyldimethylsilyloxy)benzothiophene (31, 318 mg, 69%).

$^1$H NMR (400 MHz, CDCl$_3$) δ 0.23 (s, 6H), 1.01 (s, 9H), 1.54 (s, 9H), 3.44 (s, 3H), 6.90 (dd, J=11.0, 6.6 Hz, 1H), 7.27 (d, J=3.0 Hz, 1H), 7.42 (s, 1H), 7.62 (d, J=8.8 Hz, 1H), 7.76 (d, J=8.8 Hz, 1H), 7.86 (dd, J=8.8, 2.4 Hz, 1H), 8.67 (d, J=2.6 Hz, 1H);

$^{13}$C NMR (100 MHz, CDCl$_3$) δ −4.4, 18.2, 25.7, 28.3, 34.1, 81.4, 122.5, 118.7, 119.0, 119.5, 124.1, 126.0, 134.3, 135.1, 137.9, 140.7, 144.5, 153.4, 154.3, 154.4.

Step 3: Preparation of 2-[2-(N-methyl-N—BOC)aminopyridin-5-yl]-6-hydroxybenzothiophene The target compound 2-[2-(N-methyl-N—BOC)aminopyridin-5-yl]-6-hydroxybenzothiophene (12-2, 194 mg, 90%) was obtained in the same manner as step 3 of Preparation Example 1 using 2-[2-(N-methyl-N—BOC)aminopyridin-5-yl]-6-(t-butyldimethylsilyloxy)benzothiophene (31, 295 mg, 0.606 mmol) obtained in step 2 and tetrabutylammonium fluoride (TBAF; 159 mg, 0.606 mmol).

$^1$H NMR (400 MHz, CDCl$_3$) δ 1.55 (s, 9H), 3.44 (s, 3H), 5.11 (s, 1H), 6.90 (dd, J=8.4, 1.4 Hz, 1H), 7.42 (s, 1H), 7.63 (d, J=8.8 Hz, 1H), 7.75 (d, J=8.4 Hz, 1H), 7.85 (dd, J=8.4, 2.2 1H), 8.67 (d, J=2.2 Hz, 1H);

$^{13}$C NMR (100 MHz, CDCl$_3$) δ 28.2, 29.6, 34.3, 81.6, 107.3, 114.8, 119.1, 119.7, 124.3, 126.4, 133.9, 134.3, 136.5, 141.2, 144.3, 154.1, 154.3, 154.7.

Preparation Example 3

Preparation of 2-[3-(N-methyl-N—BOC)aminopyridazin-6-yl]-6-hydroxybenzothiophene Step 1: Preparation of 6-(t-butyldimethylsilyloxy)benzothiophene-2-boronic acid 6-(t-Butyldimethylsilyloxy)benzothiophene-2-boronic acid (24) was prepared in the same manner as step 1 of Preparation Example 1.

Step 2: Preparation of 2-[3-(N-methyl-N—BOC)aminopyridazin-6-yl]-6-(t-butyldimethylsilyloxy)benzothiophene The target compound 2-[3-(N-methyl-N—BOC)aminopyridazin-6-yl]-6-(t-butyldimethylsilyloxy)benzothiophene (32) was obtained in the same manner as step 2 of Preparation Example 1, except that 6-(t-butyldimethylsilyloxy)benzothiophene-2-boronic acid (24, 902 mg, 2.92 mmol) obtained in step 1,3-(N-methyl-N—BOC)amino-6-iodopyridazine (29, 652 mg, 1.947 mmol), K$_2$CO$_3$ (303 mg, 2.19 mmol) and Pd(OAc)$_2$ (20 mg, 0.029 mmol) were used. The resulting reaction mixture was subjected to the following step without separation.

Step 3: Preparation of 2-[3-(N-methyl-N—BOC)aminopyridazin-6-yl]-6-hydroxybenzothiophene The reaction mixture of 2-[3-(N-methyl-N—BOC)aminopyridazin-6-yl]-6-(t-butyldimethylsilyloxy)benzothiophene (32) obtained in step 2 was dissolved in THF (30 mL). After adding TBAF (1.145 g, 4.38 mmol), the mixture was agitated at room temperature for 3 hours. After adding water, extracting the organic compound with ethyl acetate and removing water using sodium sulfate, column chromatography yielded the target compound 2-[3-(N-methyl-N—BOC)aminopyridazin-6-yl]-6-hydroxybenzothiophene (12-3, 628 mg, 90%) as a yellow solid.

$^1$H NMR (200 MHz, CDCl$_3$ and CD$_3$OH (4 drops)) δ 1.56 (s, 9H), 3.59 (s, 3H), 6.94 (dd, J=8.4, 2.2 Hz, 1H), 7.33 (d, J=2.2 Hz, 1H), 7.65 (d, J=8.8 Hz, 1H), 7.71 (s, 1H), 7.81 (d, J=9.8 Hz, 1H), 8.09 (d, J=9.8 Hz, 1H);

$^{13}$C NMR (50 MHz, CDCl$_3$ and CD$_3$OH (4 drops)) δ 28.1, 34.4, 82.4, 107.5, 115.0, 122.3, 123.1, 123.2, 125.0, 133.4, 137.0, 142.7, 151.8, 153.9, 155.6, 156.7.

Preparation Example 4

Preparation of 2-[4-(N-methyl-N—BOC)aminophenyl]-6-hydroxybenzothiophene

Step 1: Preparation of N-(4-methoxyphenyl)-4-nitrobenzamide

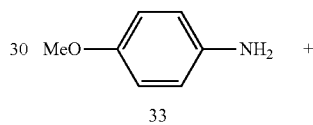

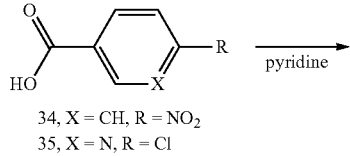

34, X = CH, R = NO$_2$
35, X = N, R = Cl

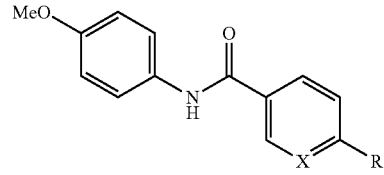

36, X = CH, R = NO$_2$
37, X = N, R = Cl

After adding 4-nitrobenzoyl chloride (34, 7.534 g, 185.57 mmol) to p-anisidine (33, 5.00 g, 40.60 mmol) dissolved in pyridine (50 mL), the reaction mixture was heated for 2 hours at 100° C. After adding water and aqueous 4 N HCl (300 mL), extracting with ethyl acetate and removing water using sodium sulfate, column chromatography yielded the target compound N-(4-methoxyphenyl)-4-nitrobenzamide (36, 8.594 g, 78%).

$^1$H NMR (200 MHz, acetone-d$_6$) δ 9.76 (br s, 1H), 8.35 (d, J=9.2 Hz, 2H), 8.22 (d, J=9.0 Hz, 2H), 7.75 (d, J=9.0 Hz, 2H), 6.94 (d, J=9.2 Hz, 2H), 3.80 (s, 3H);

¹³C NMR (50 MHz, acetone-d₆) δ 164.2, 157.4, 150.4, 142.0, 132.9, 129.7, 124.3, 122.7, 114.6, 55.6.

Step 2: Preparation of N-(4-methoxyphenyl)-6-methoxybenzothiazole

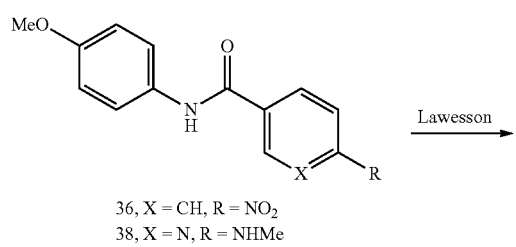

36, X = CH, R = NO₂
38, X = N, R = NHMe

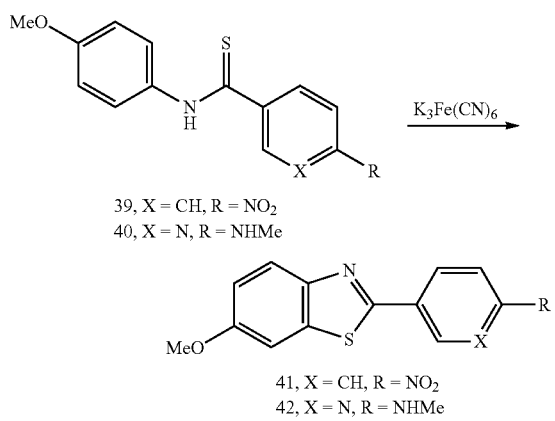

39, X = CH, R = NO₂
40, X = N, R = NHMe

41, X = CH, R = NO₂
42, X = N, R = NHMe

N-(4-Methoxyphenyl)-4-nitrobenzamide (36, 8.479 g, 31.14 mmol) obtained in step 1 and Lawesson's reagent (7.558 g, 18.69 mmol) were dissolved in chlorobenzene (20 mL) and refluxed for 6 hours. After cooling to room temperature, the resulting precipitate was filtered and the solvent was removed under reduced pressure to yield N-(4-methoxyphenyl)-4-nitrobenzothioamide (39, 6.0 g, 67%).

¹H NMR (200 MHz, acetone-d₆) δ 3.83 (s, 3H), 7.00 (d, J=9.2 Hz, 2H), 7.88 (d, J=9.2 Hz, 2H), 8.09 (d, J=8.6 Hz, 2H), 8.28 (d, J=9.0 Hz, 2H);

¹³C NMR (50 MHz, acetone-d₆) δ 55.7, 114.5, 124.1, 126.0, 129.2, 133.6, 149.3, 149.5, 159.0, 195.5.

N-(4-Methoxyphenyl)-4-nitrobenzothioamide (39, 6.0 g, 20.81 mmol) was drenched in ethanol (1 mL) and 30% NaOH aqueous solution (6.66 g, 166.48 mmol) was added. The resulting reaction mixture was diluted with water (60 mL) and K₃Fe(CN)₆ (18.0 g, 41.62 mmol) dissolved in water (50 mL) was slowly added at 90° C. After heating the reaction mixture for 1 hour at 90° C. and cooling to room temperature, the produced precipitate was filtered and washed with water. After dissolving the remaining precipitate in ethyl acetate and removing drying over sodium sulfate, column chromatography yielded the target compound 2-(4-nitrophenyl)-6-methoxybenzothiazole (41, 1.718 g, 30%) as a yellow solid.

¹H NMR (200 MHz, DMSO-d₆) δ 3.87 (s, 3H), 7.18 (dd, J=9.2, 2.6 Hz, 1H), 7.77 (d, J=2.6 Hz, 1H), 8.01 (d, J=9.2 Hz, 1H), 8.26 (d, J=9.2 Hz, 2H), 8.36 (d, J=8.8 Hz, 2H);

¹³C NMR (50 MHz, DMSO-d₆) δ 55.9, 104.9, 116.8, 124.2, 124.6, 127.9, 136.9, 138.6, 148.0, 148.4, 158.2, 162.0.

Step 3: Preparation of 2-[4-(N-monomethyl)aminophenyl]-6-methoxybenzothiazole

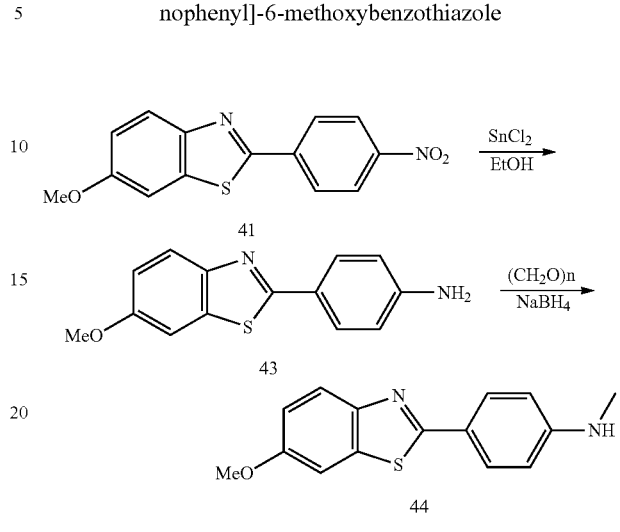

SnCl₂ (5.798 g, 30.58 mmol) was added to 2-(4-nitrophenyl)-6-methoxybenzothiazole (41, 1.459 g, 5.10 mmol) obtained in step 2 dissolved in ethanol (300 mL). The resulting reaction mixture was refluxed for 4 hours under a nitrogen atmosphere and the solvent was removed under reduced pressure. Then, the remaining mixture was dissolved in ethyl acetate and, after washing with 1N NaOH aqueous solution (50 mL) and water (100 mL), water was removed using sodium sulfate. After removing the solvent by distilling under reduced pressure, 2-(4-aminophenyl)-6-methoxybenzothiazole (43, 1.305 g, 99%) was yielded as a yellow solid without further purification.

¹H NMR (200 MHz, CDCl₃) δ 3.87 (s, 3H), 3.97 (br s, 2H), 6.73 (d, J=8.4 Hz, 2H), 7.04 (dd, J=9.2, 2.6 Hz, 1H), 7.32 (d, J=2.6 Hz, 1H), 7.90-7.82 (m, 3H);

¹³C NMR (50 MHz, CDCl₃) δ 55.8, 104.2, 114.8, 115.0, 122.9, 124.1, 128.7, 135.8, 148.8, 157.2, 166.1.

2-(4-Aminophenyl)-6-methoxybenzothiazole (43, 779 mg, 3.04 mmol) and paraformaldehyde (487 mg, 15.2 mmol) were dissolved in methanol and then added to 0.5 M NaOMe in methanol (30 mL, 15.2 mmol). The resulting reaction mixture was agitated for 4 hours at room temperature and, after adding NaBH₄ (1.0 g, 26.5 mmol), heated for 1.5 hours under reflux. After removing methanol by distilling under reduced pressure, the residue was dissolved in ethyl acetate (100 mL) and water was added thereto. After extracting the organic compound with ethyl acetate, removing water using sodium sulfate and removing the solvent under reduced pressure, column chromatography yielded the target compound 2-[4-(N-monomethyl)aminophenyl]-6-methoxybenzothiazole (44, 588 mg, 72%) as yellow solid.

¹H NMR (200 MHz, CDCl₃) δ 2.88 (s, 3H), 3.86 (s, 3H), 4.10 (br s, 1H), 6.62 (d, J=8.8 Hz, 2H), 7.03 (dd, J=8.8, 2.6 Hz, 1H), 7.30 (d, J=2.6 Hz, 1H), 7.90-7.84 (m, 3H);

¹³C NMR (50 MHz, CDCl₃) δ 30.3, 55.7, 104.3, 112.0, 114.9, 122.7, 128.7, 135.7, 148.8, 151.2, 157.1, 166.4.

Step 4: Preparation of 2-[4-(N-methyl-N—BOC)aminophenyl]-6-hydroxybenzothiazole

After adding BBr₃ (1.0 M in CH₂Cl₂, 10.5 mL, 10.5 mmol) to 2-[4-(N-monomethyl)aminophenyl]-6-methoxybenzothiazole (44, 588 mg, 2.06 mmol) obtained in step 3 dissolved in dichloromethane (25 mL), the mixture was agitated for 12 hours at room temperature. After cautiously adding water and sodium bicarbonate aqueous solution, the organic compound was extracted using dichloromethane. Then, after removing water using sodium sulfate, 2-[4-(N-monomethyl) aminophenyl]-6-hydroxybenzothiazole (45, 530 mg, 99%) was yielded as a yellow solid without further purification.

$^1$H NMR (200 MHz, DMSO-d$_6$) δ 2.74 (d, J=4.8 Hz, 3H), 6.38 (brd, J=5.0 Hz, 1H), 6.62 (d, J=8.4 Hz, 2H), 6.90 (dd, J=8.8, 2.2 Hz, 1H), 7.31 (d, J=2.2 Hz, 1H), 7.69 (d, J=8.8 Hz, 1H), 7.73 (d, J=8.4 Hz, 2H), 9.70 (s, 1H);

$^{13}$C NMR (100 MHz, DMSO-d$_6$) δ 29.3, 106.7, 111.4, 115.4, 120.4, 122.3, 128.1, 135.1, 147.3, 152.0, 154.8, 164.4.

2-[4-(N-monomethyl)aminophenyl]-6-hydroxybenzothiazole (45, 520 mg, 2.03 mmol) was dissolved in tetrahydrofuran (15 mL) and (BOC)$_2$O (974 mg, 4.46 mmol) and N,N-dimethylaminopyridine (DMAP; 496 mg, 4.06 mmol) were sequentially added thereto. After agitating the resulting reaction mixture for 16 hours at room temperature and removing the solvent under reduced pressure, the mixture was dissolved again in dichloromethane (40 mL). Then, after adding piperidine (4.0 mL, 40.6 mmol), the reaction mixture was agitated for 1 hour at room temperature and ammonium chloride aqueous solution was added. After extracting the organic compound with dichloromethane and removing water using sodium sulfate, column chromatography yielded the target compound 2-[2-(N-monomethyl)amino)pyridin-5-yl]-6-hydroxybenzothiazole (12-4, 519 mg, 72%) as a white solid.

$^1$H NMR (200 MHz, acetone-d$_6$) δ 1.47 (s, 9H), 3.31 (s, 3H), 7.07 (dd, J=8.8, 2.2 Hz, 1H), 7.51-1.45 (m, 3H), 7.85 (d, J=8.8 Hz, 1H), 8.02 (d, J=8.4 Hz, 2H);

$^{13}$C NMR (50 MHz, acetone-d$_6$) δ 28.4, 37.2, 80.9, 107.5, 116.8, 124.5, 126.2, 127.8, 131.0, 137.3, 147.0, 154.6, 156.6, 164.3.

Preparation Example 5

Preparation of 2-[2-(N-methyl-N—BOC)aminopyridin-5-yl]-6-hydroxybenzothiazole

Step 1: Preparation of 6-chloro-N-(4-methoxyphenyl)nicotinamide

6-Chloronicotinoyl chloride (35, 17.6 g, 100.0 mmol) was added to p-anisidine (33, 12.3 g, 100.0 mmol) dissolved in pyridine (150 mL) solution and the resulting reaction mixture was heated for 3 hours at 120° C. After cooling to room temperature and adding water, the produced gray precipitate was filtered and washed with 5% sodium bicarbonate aqueous solution. Then, the solvent was removed under reduced pressure to obtain the target compound 6-chloro-N-(4-methoxyphenyl)nicotinamide (37, 16.0 g, 60%).

$^1$H NMR (400 MHz, DMSO-d$_6$) δ 3.71 (s, 3H), 6.90 (dd, J=7.2, 2.0 Hz, 2H), 7.61 (dd, J=7.2, 2.0 Hz, 2H), 7.65 (d, J=8.4 Hz, 1H), 8.26 (dd, J=8.2, 2.6 Hz, 1H), 8.89 (d, J=2.8 Hz, 1H), 10.31 (s, 1H);

$^{13}$C NMR (100 MHz, DMSO-d$_6$) δ 55.2, 113.8, 122.0, 124.1, 130.0, 131.6, 138.9, 149.2, 152.6, 155.8, 162.4.

Step 2: Preparation of 6-(N-monomethylamino)-N-(4-methoxyphenyl)nicotinamide

Methanol (20 mL), triethylamine (1.59 mL, 11.4 mmol) and monomethylamine (2.0 M in MeOH, 19 mL, 38.0 mmol) were added to a pressure tube containing 6-chloro-N-(4-methoxyphenyl)nicotinamide (37, 2.0 g, 7.61 mmol) obtained in step 1. After agitating at 100° C. overnight and then cooling to room temperature, the product was removed by filtration. Removal of the solvent under reduced pressure yielded the target compound 6-(N-monomethylamino)-N-(4-methoxyphenyl)nicotinamide (38, 1.76 g, 90%) without further purification.

$^1$H NMR (200 MHz, DMSO-d$_6$) δ 2.87 (d, J=4.8 Hz, 3H), 3.77 (s, 3H), 6.53 (d, J=8.8 Hz, 1H), 6.94 (d, J=8.8 Hz, 2H), 7.18 (d, J=4.8 Hz, 1H), 7.67 (d, J=9.0 Hz, 2H), 7.96 (dd, J=8.8, 2.2 Hz, 1H), 8.68 (d, J=2.2 Hz, 1H), 9.85 (s, 1H);

$^{13}$C NMR (50 MHz, DMSO-d$_6$) δ 27.8, 55.2, 113.6, 117.8, 121.8, 122.0, 132.5, 135.8, 148.7, 155.2, 160.8, 164.0.

Step 3: Preparation of 2-[2-(N-monomethyl)aminopyridin-5-yl]-6-methoxybenzothiazole N-(4-Methoxyphenyl)-6-(N-monomethylamino)nicotinethioamide (40, 404 mg, 50%) was obtained in the same manner as step 2 of Preparation Example 4 using 6-(N-monomethylamino)-N-(4-methoxyphenyl)nicotinamide (38, 760 mg, 2.95 mmol) obtained in step 2 and Lawesson's reagent (739 mg, 1.77 mmol).

$^1$H NMR (400 MHz, DMSO-d$_6$) δ 2.80 (d, J=4.8 Hz, 3H), 3.73 (s, 3H), 6.42 (d, J=8.8 Hz, 1H), 6.92 (d, J=8.8 Hz, 2H), 7.14 (d, J=4.4 Hz, 1H), 7.57 (d, J=8.4 Hz, 2H), 7.95 (d, J=8.0 Hz, 1H), 8.58 (s, 1H), 11.18 (s, 1H);

$^{13}$C NMR (100 MHz, DMSO-d$_6$) δ 27.9, 55.2, 113.5, 125.4, 126.1, 133.2, 136.7, 147.7, 157.0, 160.7, 193.9.

The target compound 2-[2-(N-monomethyl)aminopyridin-5-yl]-6-methoxybenzothiazole (42, 650 mg, 88%) was obtained in the same manner as in step 4 of Preparation Example 4 using 6-(N-monomethylamino)-N-(4-methoxyphenyl)nicotinethioamide (40, 740 mg, 2.71 mmol), 30% NaOH aqueous solution (867 mg, 21.7 mmol) and K$_3$Fe (CN)$_6$ (3.6 g, 10.8 mmol) dissolved in water (12 mL).

$^1$H NMR (400 MHz, DMSO-d$_6$) δ 2.81 (d, J=4.8 Hz, 3H), 3.78 (s, 3H), 6.53 (d, J=8.8 Hz, 7.02 (dd, J=9.0, 2.6 Hz, 1H), 7.16 (d, J=5.2 Hz, 1H), 7.58 (d, J=2.8 Hz, 1H), 7.78 (d, J=8.8 Hz, 1H), 7.92 (dd, J=8.8, 2.4 Hz, 1H), 8.60 (d, J=2.8 Hz, 1H);

$^{13}$C NMR (100 MHz, DMSO-d$_6$) δ 27.8, 55.7, 104.9, 107.9, 115.3, 117.4, 122.4, 134.8, 135.0, 147.3, 148.0, 156.9, 160.5, 163.3.

Step 4: Preparation of 2-[2-(N-methyl-N—BOC-amino)pyridin-5-yl]-6-hydroxybenzothiazole 2-[2-(N-Monomethyl)aminopyridin-5-yl]-6-methoxybenzothiazole (42, 650 mg, 2.40 mmol) obtained in step 3 was dissolved in [bmim][BF$_4$] (13 mL) and, after adding bromic acid (48%, 2.4 mL), the reaction mixture was held at 130° C. overnight. After cooling to room temperature and adding water and sodium bicarbonate aqueous solution, the solid thus obtained was filtered and washed with water. After removing the solvent under reduced pressure, recrystallization from methanol and dichloromethane solvent yielded 2-[2-(N-monomethyl)aminopyridin-5-yl]-6-hydroxybenzothiazole (46, 550 mg, 89%) as a brown solid.

$^1$H NMR (400 MHz, DMSO-d$_6$) δ 2.80 (d, J=4.4 Hz, 3H), 6.52 (d, J=8.8 Hz, 1H), 6.89 (dq, J=8.4, 1.1 Hz, 1H), 7.13 (d, J=4.4 Hz, 1H), 7.31 (d, J=2.4 Hz, 1H), 7.70 (d, J=8.8 Hz, 1H), 7.90 (dd, J=8.8, 2.0 Hz, 1H), 8.57 (d, J=2.4 Hz, 1H), 9.69 (s, 1H);

$^{13}$C NMR (100 MHz, DMSO-d$_6$) δ 28.5, 107.4, 108.6, 116.2, 118.2, 123.2, 135.3, 135.6, 147.8, 150.2, 155.8, 161.1, 162.8.

The target compound 2-[2-(N-methyl-N—BOC)aminopyridin-5-yl]-6-hydroxybenzothiazole (12-5, 350 mg, 46%)

was obtained in the same manner as in step 4 of Preparation Example 4 using 2-[2-(N-monomethyl)aminopyridin-5-yl]-6-hydroxybenzothiazole (46, 550 mg, 2.14 mmol), (BOC)$_2$O (589 mg, 2.56 mmol) and N,N-dimethylaminopyridine (DMAP; 261 mg, 2.14 mmol).

$^1$H NMR (400 MHz, DMSO-d$_6$) δ 1.45 (s, 9H), 3.32 (s, 3H), 6.96 (dq, J=8.8, 1.3 Hz, 1H), 7.39 (m, 1H), 7.82 (dd, J=8.6, 1.4 Hz, 2H), 8.25 (dq, J=8.6, 1.5 Hz, 1H), 8.90 (dd, J=1.4, 1.0 Hz, 1H), 9.88 (s, 1H);

$^{13}$C NMR (100 MHz, DMSO-d$_6$) δ 28.4, 34.5, 82.0, 107.5, 117.0, 119.0, 124.1, 125.3, 135.9, 136.5, 146.0, 147.6, 153.9, 156.4, 156.6, 160.9.

Preparation Example 6

Preparation of 6-[(R/S)-(2,2-dimethyl-1,3-dioxolan-4-yl)methyloxy]benzothiophene-2-boronic acid

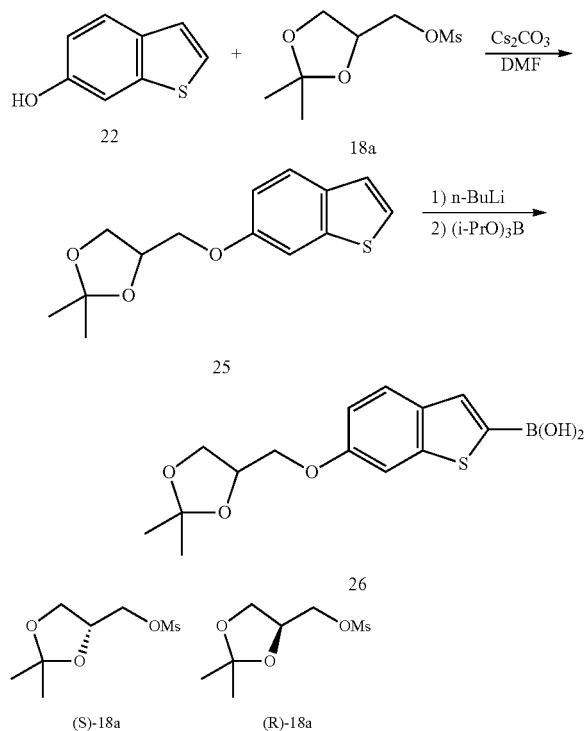

Step 1: Preparation of 6-[(R/S)-(2,2-dimethyl-1,3-dioxolan-4-yl)methyloxy]benzothiophene Dimethylformamide (10 mL) was added to a reactor containing 6-hydroxybenzothiophene (22, 619 mg, 4.12 mmol), (R/S)-(2,2-dimethyl-1,3-dioxolan-4-yl)methyl methanesulfonate ((R/S)-18a, 1.04 g, 4.95 mmol) and Cs$_2$CO$_3$ (1.61 g, 4.95 mmol). The reaction mixture was agitated at 100° C. for 6 hours and then cooled to room temperature. After adding water, extracting with ethyl acetate, washing with saturated ammonium chloride aqueous solution, and removing water using sodium sulfate, column chromatography yielded 6-[(R/S)-(2,2-dimethyl-1,3-dioxolan-4-yl)methyloxy]benzothiophene ((R/S)-25, 1.08 g, 99%) as a liquid.

$^1$H NMR (200 MHz, CDCl$_3$) δ 1.42 (s, 3H), 1.48 (s, 3H), 3.89-4.04 (m, 2H), 4.09-4.23 (m, 2H), 4.47-4.58 (m, 1H), 7.02 (dd, J=8.8, 2.2 Hz, 1H), 7.22-7.26 (m, 2H), 7.36 (d, J=2.2 Hz, 1H), 7.69 (d, J=8.4 Hz, 1H);

$^{13}$C NMR (50 MHz, CDCl$_3$) δ 25.4, 26.8, 66.9, 69.3, 74.0, 105.8, 109.8, 114.7, 123.4, 124.0, 124.1, 134.0, 156.3.

Step 2: Preparation of 6-[(R/S)-(2,2-dimethyl-1,3-dioxolan-4-yl)methyloxy]benzothiophene-2-boronic acid 2.5 M n-butyllithium (1.75 mL, 4.37 mmol) in hexane was slowly added to 6-[(R/S)-(2,2-dimethyl-1,3-dioxolan-4-yl)methyloxy]benzothiophene ((R/S)-25, 1.05 g, 3.97 mmol) obtained in step 1 dissolved in anhydrous tetrahydrofuran (150 mL) at −78° C. under nitrogen atmosphere. 15 Minutes later, the resulting mixture was agitated at room temperature for 1 hour. After cooling again to −78° C., triisopropyl borate ((i-PrO)$_3$B; 1.10 mL, 4.77 mmol) was slowly added. After slowly heating to room temperature and agitating for 3 hours, water was added to quench the reaction. After extracting the organic compound with ethyl acetate and drying with sodium sulfate, column chromatography yielded the target compound 6-[(R/S)-(2,2-dimethyl-1,3-dioxolan-4-yl)methyloxy]benzothiophene-2-boronic acid ((R/S)-26, 880 mg, 72%).

$^1$H NMR (400 MHz, CDCl$_3$) δ 1.44 (s, 1H), 1.51 (s, 3H), 3.90-3.94 (m, 2H), 4.05-4.08 (m, 1H), 4.17-4.21 (m, 1H), 4.47-4.51 (m, 1H), 7.00 (dd, J=8.6, 1.8 Hz, 1H), 7.30 (s, 1H), 7.76 (d, J=8.8 Hz, 1H), 8.04 (s, 1H);

$^{13}$C NMR (100 MHz, CDCl$_3$) δ 25.6, 27.1, 67.0, 69.5, 74.1, 105.3, 110.2, 115.7, 125.9, 135.1, 136.9, 146.8, 158.0.

Preparation Example 7

Preparation of 6-[(R)-(2,2-dimethyl-1,3-dioxolan-4-yl)methyloxy]benzothiophene-2-boronic acid Step 1: Preparation of 6-[(R)-(2,2-dimethyl-1,3-dioxolan-4-yl)methyloxy]benzothiophene The target compound 6-[(R)-(2,2-dimethyl-1,3-dioxolan-4-yl)methyloxy]benzothiophene ((R)-25, 1.36 g, 89%) was obtained as a liquid in the same manner as in step 1 of Preparation Example 6 using 6-hydroxybenzothiophene (22, 867 mg, 5.77 mmol), (R)-(2,2-dimethyl-1,3-dioxolan-4-yl)methyl methanesulfonate ((R)-18a, 1.33 g, 6.35 mmol) and Cs$_2$CO$_3$ (2.26 g, 6.93 mmol).

$^1$H NMR (200 MHz, CDCl$_3$) δ 1.42 (s, 3H), 1.48 (s, 3H), 3.89-4.04 (m, 2H), 4.09-4.23 (m, 2H), 4.47-4.58 (m, 1H), 7.02 (dd, J=8.8, 2.2 Hz, 1H), 7.22-7.26 (m, 2H), 7.36 (d, J=2.2 Hz, 1H), 7.69 (d, J=8.4 Hz, 1H);

$^{13}$C NMR (50 MHz, CDCl$_3$) δ 25.4, 26.8, 66.9, 69.3, 74.0, 105.8, 109.8, 114.7, 123.4, 124.0, 124.1, 134.0, 156.3.

Step 2: Preparation of 6-[(R)-(2,2-dimethyl-1,3-dioxolan-4-yl)methyloxy]benzothiophene-2-boronic acid The target compound 6-[(R)-(2,2-dimethyl-1,3-dioxolan-4-yl]methyloxy)benzothiophene-2-boronic acid ((R)-26, 960 mg, 44%) was obtained in the same manner as in step 2 of Preparation Example 6 using 6-[(R)-(2,2-dimethyl-1,3-dioxolan-4-yl)methyloxy]benzothiophene ((R)-25, 1.865 g, 7.06 mmol) obtained in step 1, 2.5 M n-butyllithium (5.6 mL, 14.1 mmol) in hexane and triisopropyl borate ((i-PrO)$_3$B; 3.2 mL, 13.92 mmol).

$^1$H NMR (400 MHz, CDCl$_3$) δ 1.44 (s, 1H), 1.51 (s, 3H), 3.90-3.94 (m, 2H), 4.05-4.08 (m, 1H), 4.17-4.21 (m, 1H), 4.47-4.51 (m, 1H), 7.00 (dd, J=8.6, 1.8 Hz, 1H), 7.30 (s, 1H), 7.76 (d, J=8.8 Hz, 1H), 8.04 (s, 1H);

$^{13}$C NMR (100 MHz, CDCl$_3$) δ 25.6, 27.1, 67.0, 69.5, 74.1, 105.3, 110.2, 115.7, 125.9, 135.1, 136.9, 146.8, 158.0.

Preparation Example 8

Preparation of 6-[(S)-(2,2-dimethyl-1,3-dioxolan-4-yl)methyloxy]benzothiophene-2-boronic acid Step 1: Preparation of 6-[(S)-(2,2-dimethyl-1,3-dioxolan-4-yl)methyloxy]benzothiophene The target compound 6-[(S)-(2,2-dimethyl-1,3-dioxolan-4-yl)methyloxy]benzothiophene ((S)-25, 1.42 g, 95%) was obtained as a liquid in the same manner as in step 1 of Preparation Example 6 using 6-hydroxybenzothiophene (22, 844 mg, 5.62 mmol), (S)-(2,2-dimethyl-1,3-dioxolan-4-yl)methyl methanesulfonate ((S)-18a, 1.30 g, 6.18 mmol) and Cs$_2$CO$_3$ (2.20 g, 6.74 mmol).

$^1$H NMR (200 MHz, CDCl$_3$) δ 1.42 (s, 3H), 1.48 (s, 3H), 3.89-4.04 (m, 2H), 4.09-4.23 (m, 2H), 4.47-4.58 (m, 1H), 7.02 (dd, J=8.8, 2.2 Hz, 1H), 7.22-7.26 (m, 2H), 7.36 (d, J=2.2 Hz, 1H), 7.69 (d, J=8.4 Hz, 1H);

$^{13}$C NMR (50 MHz, CDCl$_3$) δ 25.4, 26.8, 66.9, 69.3, 74.0, 105.8, 109.8, 114.7, 123.4, 124.0, 124.1, 134.0, 156.3.

Step 2: Preparation of 6-[(S)-(2,2-dimethyl-1,3-dioxolan-4-yl)methyloxy]benzothiophene-2-boronic acid The target compound 6-[(S)-(2,2-dimethyl-1,3-dioxolan-4-yl)methyloxy]benzothiophene-2-boronic acid ((S)-26, 610 mg, 48%) was obtained in the same manner as in step 2 of Preparation Example 6 using 6-[(S)-(2,2-dimethyl-1,3-dioxolan-4-yl)methyloxy]benzothiophene ((S)-25, 1.10 g, 4.16 mmol) obtained in Preparation Example 3, 2.5 M n-butyllithium (3.33 mL, 8.32 mmol) in hexane and triisopropyl borate ((i-PrO)$_3$B, 1.91 mL, 8.31 mmol).

$^1$H NMR (400 MHz, CDCl$_3$) δ 1.44 (s, 1H), 1.51 (s, 3H), 3.90-3.94 (m, 2H), 4.05-4.08 (m, 1H), 4.17-4.21 (m, 1H), 4.47-4.51 (m, 1H), 7.00 (dd, J=8.6, 1.8 Hz, 1H), 7.30 (s, 1H), 7.76 (d, J=8.8 Hz, 1H), 8.04 (s, 1H);

$^{13}$C NMR (100 MHz, CDCl$_3$) δ 25.6, 27.1, 67.0, 69.5, 74.1, 105.3, 110.2, 115.7, 125.9, 135.1, 136.9, 146.8, 158.0.

Example 1

Preparation of 2-[4-(N-monomethyl)aminophenyl]-6-[(R/S)-3-fluoro-2-hydroxypropoxy]benzothiophene Step 1: Preparation of 2-[4-(N-methyl-N—BOC) aminophenyl]-6-allyloxybenzothiophene

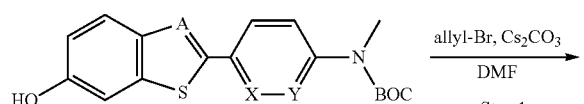

12-1, A = X = Y = CH
12-2, A = X = CH, Y = N
12-3, A = CH, X = Y = N
12-4, A = N, X = Y = CH
12-5, A = Y= N, X = CH

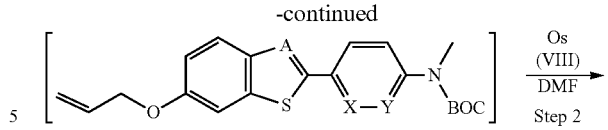

13-1, A = X = Y = CH
13-2, A = X = CH, Y = N
13-3, A = CH, X = Y = N
13-4, A = N, X = Y = CH
13-5, A = Y= N, X = CH 14-1, A = X = Y = CH
14-2, A = X = CH, Y = N
14-3, A = CH, X = Y = N
14-4, A = N, X = Y = CH
14-5, A = Y= N, X = CH

2-[4-(N-Methyl-N—BOC)aminophenyl]-6-allyloxybenzothiophene (13-1) was prepared by adding allyl bromide (0.062 mL, 0.716 mmol) and Cs$_2$CO$_3$ (388 g, 1.192 mmol) to 2-[4-(N-methyl-N—BOC)aminophenyl]-6-hydroxybenzothiophene (12-1, 212 mg, 0.596 mmol) obtained in Preparation Example 1 dissolved in dimethylformamide (DMF; 5 mL) and heating for 1 hour at 100° C. The prepared compound was used in the subsequent step without purification.

Step 2: Preparation of 2-[4-(N-methyl-N—BOC) aminophenyl)-6-((R/S)-2,3-dihydroxypropoxy)benzothiophene After sequentially adding osmium tetroxide (OsO$_4$, 4 wt % in H$_2$O, 0.038 mL, 0.006 mmol), N-methylmorpholine N-oxide (105 mg, 0.894 mmol) and DABCO (5 mg, 0.045 mmol) to 2-[4-(N-methyl-N—BOC)aminophenyl]-6-allyloxybenzothiophene (13-1) prepared in step 1, reaction was performed at 45° C. for 24 hours. After adding water to the reaction mixture, extracting the organic compound using ethyl acetate and drying with sodium sulfate, column chromatography yielded the target compound 2-[4-(N-methyl-N—BOC)aminophenyl]-6-((R/S)-2,3-dihydroxypropoxy) benzothiophene (14-1, 200 mg, 78%).

$^1$H NMR (400 MHz, CDCl$_3$+CD$_3$OD) δ 1.47 (s, 9H), 3.28 (s, 3H), 3.73 (dd, J=11.6, 5.2 Hz, 1H), 3.82 (dd, J=11.2, 3.2 Hz, 1H), 4.07-4.11 (m, 3H), 6.98 (dd, J=8.8, 2.4 Hz, 1H), 7.23 (s, 1H), 7.30 (s, 1H), 7.31 (d, J=2.4 Hz, 1H), 7.41 (s, 1H), 7.60-7.63 (m, $^3$H);

¹³C NMR (100 MHz, CDCl₃+CD₃OD) δ 28.2, 37.1, 63.4, 69.5, 70.3, 80.7, 105.9, 114.7, 118.8, 124.1, 125.6, 126.1, 131.4, 135.0, 140.8, 141.2, 143.2, 154.7, 156.3

Step 3: Preparation of 2-[4-(N-methyl-N—BOC) aminophenyl]-6-[(R/S)-3-methanesulfonyloxy-2-hydroxypropoxy]benzothiophene

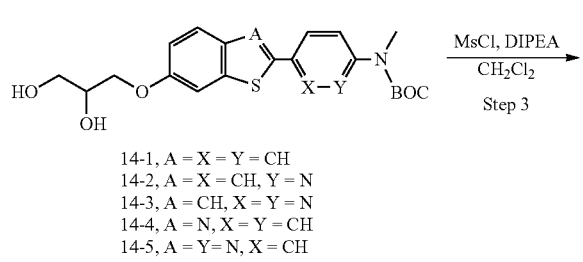

14-1, A = X = Y = CH
14-2, A = X = CH, Y = N
14-3, A = CH, X = Y = N
14-4, A = N, X = Y = CH
14-5, A = Y = N, X = CH

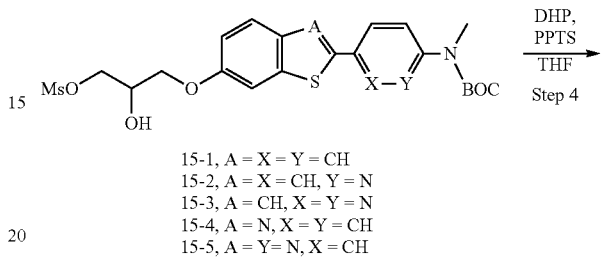

15-1, A = X = Y = CH
15-2, A = X = CH, Y = N
15-3, A = CH, X = Y = N
15-4, A = N, X = Y = CH
15-5, A = Y = N, X = CH

After dissolving 2-[4-(N-methyl-N—BOC)aminophenyl]-6-((R/S)-2,3-dihydroxypropoxy)benzothiophene (14-1, 180 mg, 0.419 mmol) obtained in step 2 in dichloromethane (13 mL) and cooling to −10° C., diisopropylethylamine (DIPEA; 0.088 mL, 0.503 mmol) and methanesulfonyl chloride (MsCl; 0.036 mL, 0.461 mmol) were sequentially added thereto. After agitating the reaction mixture at −10° C. for 30 minutes, adding water, extracting the resulting product using ethyl acetate, and drying with sodium sulfate, column chromatography yielded the target compound 2-[4-(N-methyl-N—BOC)aminophenyl]-6-[(R/S)-3-methanesulfonyloxy-2-hydroxypropoxy]benzothiophene (15-1, 103 mg, 48%).

¹H NMR (400 MHz, CDCl₃) δ 1.48 (s, 9H), 3.09 (s, 3H), 3.29 (s, 3H), 4.12 (d, J=5.2 Hz, 2H), 4.30-4.47 (m, 3H), 6.97 (dd, J=8.8, 2.6 Hz, 1H), 7.26-7.31 (m, 3H), 7.41 (s, 1H), 7.59-7.66 (m, 3H);

¹³C NMR (100 MHz, CDCl₃) δ 28.3, 37.1, 37.6, 68.2, 70.2, 80.7, 106.0, 114.6, 118.8, 124.3, 125.6, 126.3, 131.2, 135.4, 140.8, 141.7, 143.5, 154.6, 155.8.

Step 4: Preparation of 2-[4-(N-methyl-N—BOC) aminophenyl]-6-[(R/S)-3-methanesulfonyloxy-2-(tetrahydropyran-2-yloxy)propoxy]benzothiophene

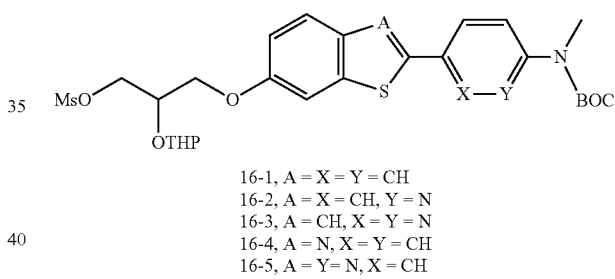

15-1, A = X = Y = CH
15-2, A = X = CH, Y = N
15-3, A = CH, X = Y = N
15-4, A = N, X = Y = CH
15-5, A = Y = N, X = CH 16-1, A = X = Y = CH
16-2, A = X = CH, Y = N
16-3, A = CH, X = Y = N
16-4, A = N, X = Y = CH
16-5, A = Y = N, X = CH

After dissolving 2-[4-(N-methyl-N—BOC)aminophenyl]-6-[(R/S)-3-methanesulfonyloxy-2-hydroxypropoxy]benzothiophene (15-1, 100 mg, 0.197 mmol) obtained in step 3 and pyridinium p-toluenesulfonate (PPTS; 10 mg, 0.039 mmol) in dichloromethane (3 mL) and adding dihydropyran (DHP; 33.4 mL, 0.394 mmol), the reaction mixture was agitated at room temperature for 17 hours. After adding water to the reaction mixture, extracting the organic compound with dichloromethane and drying with sodium sulfate, column chromatography yielded the target compound 2-[4-(N-methyl-N—BOC)aminophenyl]-6-[(R/S)-3-methanesulfonyloxy-2-(tetrahydropyran-2-yloxy)propoxy]benzothiophene (16-1, 110 mg, 94%).

¹H NMR (200 MHz, CDCl₃) δ 1.48 (s, 9H), 1.52-1.64 (m, 4H), 1.74-1.83 (m, 2H), 3.05 (s, 1.5H), 3.19 (s, 1.5H), 3.29 (s, 3H), 3.48-3.61 (m, 2H), 3.83-4.07 (m, 2H), 4.10-4.21 (m, 2H), 4.24-4.46 (m, 2H), 4.51-4.61 (m, 1H), 4.83-4.97 (m, 1H), 6.98 (dt, J=8.8, 2.0 Hz, 1H), 7.31-7.34 (m, 3H), 7.42 (s, 1H), 7.59-7.67 (m, 3H);

¹³C NMR (50 MHz, CDCl₃) δ 19.5, 19.7, 25.2, 25.4, 28.3, 29.7, 30.56, 30.62, 30.7, 37.1, 37.4, 37.5, 37.6, 62.9, 67.3, 68.2, 68.4, 70.2, 72.6, 73.0, 80.6, 94.6, 98.9, 99.3, 105.9, 106.0, 114.6, 114.7, 118.7, 118.8, 124.2, 124.3, 125.6, 126.26, 126.27, 131.17, 131.23, 135.1, 135.2, 135.4, 140.8, 141.4, 141.5, 141.7, 143.45, 143.47, 143.51, 154.6, 155.8, 156.00, 156.08.

Steps 5 and 6: Preparation of 2-[4-(N-monomethyl) aminophenyl]-6-[(R/S)-3-fluoro-2-hydroxypropoxy] benzothiophene

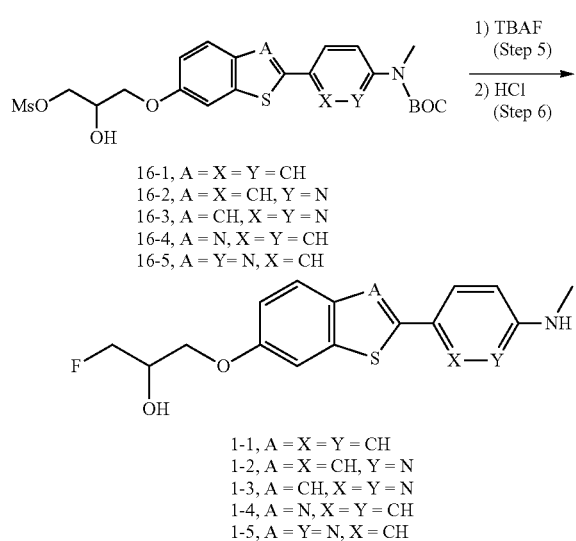

16-1, A = X = Y = CH
16-2, A = X = CH, Y = N
16-3, A = CH, X = Y = N
16-4, A = N, X = Y = CH
16-5, A = Y= N, X = CH 1-1, A = X = Y = CH
1-2, A = X = CH, Y = N
1-3, A = CH, X = Y = N
1-4, A = N, X = Y = CH
1-5, A = Y= N, X = CH

2-[4-(N-Methyl-N—BOC)aminophenyl]-6-[(R/S)-3-methanesulfonyloxy-2-(tetrahydropyran-2-yloxy)propoxy] benzothiophene (16-1, 120 mg, 0.203 mmol) obtained in step 4 and tetrabutylammonium fluoride (TBAF; 63 mg, 0.243 mmol) were dissolved in t-amyl alcohol (3 mL) and agitated at 100° C. for 6 hours. After cooling to room temperature, removing the solvent under reduced pressure and adding 4 M HCl (0.5 mL) and tetrahydrofuran (2 mL), the mixture was agitated at 80° C. for 30 minutes. After cooling to room temperature, adding water, treating with saturated sodium bicarbonate aqueous solution, extracting the organic compound with ethyl acetate, and drying with sodium sulfate, column chromatography yielded the target compound 2-[4-(N-monomethyl)aminophenyl]-6-[(R/S)-3-fluoro-2-hydroxypropoxy]benzothiophene (1-1, 65 mg, 81%).

$^1$H NMR (400 MHz, THF-$d_8$) δ 2.79 (d, J=5.2 Hz, 3H), 4.04-4.15 (m, 3H), 4.49 (dddd, J=47.9, 23.6, 9.2, 4.8 Hz, 2H), 4.69 (d, J=4.8 Hz, 1H), 5.17 (q, J=4.8 Hz, 1H), 6.56 (d, J=8.4 Hz, 2H), 6.92 (dd, J=8.4, 2.0 Hz, 1H), 7.28 (s, 1H), 7.38 (d, J=2.4 Hz, 1H), 7.45 (d, J=8.8 Hz, 2H), 7.54 (d, J=8.8 Hz, 1H);

$^{13}$C NMR (100 MHz, THF-$d_8$) δ 30.3, 69.5 (d, J=19.3 Hz), 69.8 (d, J=7.4 Hz), 85.2 (d, J=168.9 Hz), 106.6, 112.6, 115.1, 116.4, 123.4, 124.0, 127.7, 136.5, 140.9, 143.9, 151.0, 157.1.

Example 2

Preparation of 2-[2-(N-monomethyl)aminopyridin-5-yl]-6-[(R/S)-3-fluoro-2-hydroxypropoxy]benzothiophene Step 1: Preparation of 2-[2-(N-methyl-N—BOC) aminopyridin-5-yl]-6-allyloxybenzothiophene 2-[2-(N-methyl-N—BOC)aminopyridin-5-yl]-6-allyloxybenzothiophene (13-2, 520 mg, 1.31 mmol, 72%) was prepared in the same manner as in step 1 of Example 1 using 2-[2-(N-methyl-N—BOC)-aminopyridin-5-yl]-6-hydroxybenzothiophene (12-2, 650 mg, 1.82 mmol) obtained in Preparation Example 2. The compound thus prepared was used in the subsequent step without purification.

Step 2: Preparation of 2-[2-(N-methyl-N—BOC) aminopyridin-5-yl]-6-((R/S)-2,3-dihydroxypropoxy) benzothiophene 2-[2-(N-methyl-N—BOC)aminopyridin-5-yl]-6-allyloxybenzothiophene (13-2, 520 mg, 1.31 mmol) prepared in step 1 was dissolved in tetrahydrofuran/water (5 mL/5 mL). After sequentially adding osmium tetroxide (4 wt % in H$_2$O, 0.082 mL, 0.013 mmol), N-methylmorpholine N-oxide (231 mg, 1.965 mmol) and DABCO (5 mg, 0.045 mmol), the target compound 2-[3-(N-methyl-N—BOC)aminopyridin-5-yl]-6-((R/S)-2,3-dihydroxypropoxy)benzothiophene (14-2, 470 mg, 83%) was obtained in the same manner as in step 2 of Example 1.

$^1$H NMR (400 MHz, CDCl$_3$) δ 1.55 (s, 9H), 3.43 (s, 3H), 3.79 (d, J=4.6 Hz, 1H), 3.84 (d, J=3.6 Hz, 1H), 4.10 (s, 3H), 6.98 (dd, J=8.8, 2.2 Hz, 1H), 7.29 (d, J=2.2 Hz, 1H), 7.34 (s, 1H), 7.62 (d, J=8.8 Hz, 1H), 7.74 (d, J=8.8 Hz, 1H), 7.84 (dd, J=8.8, 2.6 Hz, 1H), 8.64 (d, J=2.6 Hz, 1H);

$^{13}$C NMR (100 MHz, CDCl$_3$) δ 28.3, 29.7, 34.2, 63.9, 69.6, 70.4, 81.5, 105.9, 114.8, 118.7, 119.4, 124.3, 125.9, 134.2, 134.9, 137.9, 140.9, 144.5, 154.3, 154.4, 156.4.

Step 3: Preparation of 2-[2-(N-methyl-N—BOC) aminopyridin-5-yl]-6-[(R/S)-3-methanesulfonyloxy-2-hydroxy propoxy]benzothiophene The target compound 2-[2-(N-methyl-N—BOC)aminopyridin-5-yl]-6-[(R/S)-3-methanesulfonyloxy-2-hydroxy propoxy]benzothiophene (15-2, 430 mg, 77%) was obtained in the same manner as in step 3 of Example 1 using 2-[2-(N-methyl-N—BOC)aminopyridin-5-yl]-6-((R/S)-2,3-dihydroxypropoxy)benzothiophene (14-2, 470 mg, 1.10 mmol) obtained in step 2, diisopropylethylamine (DIPEA; 0.23 mL, 1.32 mmol) and methanesulfonyl chloride (MsCl; 0.094 mL, 1.21 mmol).

$^1$H NMR (400 MHz, CDCl$_3$+CD$_3$OD) δ 1.55 (s, 9H), 3.01 (s, 3H), 3.43 (s, 3H), 4.12 (d, J=5.2 Hz, 2H), 4.30-4.51 (m, 3H), 7.50 (dd, J=8.8, 2.2 Hz, 1H), 7.43 (s, 1H), 7.66 (d, J=8.8 Hz, 1H), 7.75 (d, J=8.8 Hz, 1H), 7.87 (dd, J=9.2, 2.6 Hz, 1H), 8.66 (d, J=2.2 Hz, 1H);

$^{13}$C NMR (100 MHz, CDCl$_3$) δ 28.2, 34.2, 37.5, 67.9, 68.4, 70.5, 81.5, 106.0, 114.8, 118.8, 119.4, 124.4, 125.9, 134.3, 135.1, 138.1, 140.9, 144.5, 154.3, 154.4, 156.0.

Step 4: Preparation of 2-[2-(N-methyl-N—BOC) aminopyridin-5-yl]-6-[(R/S)-3-methanesulfonyloxy-2-(tetrahydropyran-2-yloxy)propoxy]benzothiophene The target compound 2-[2-(N-methyl-N—BOC)aminopyridin-5-yl]-6-[(R/S)-3-methanesulfonyloxy-2-(tetrahydropyran-2-yloxy)propoxy]benzothiophene (16-2, 103 mg, 75%) was obtained in the same manner as in step 4 of Example 1 except for using 2-[2-(N-methyl-N—BOC)aminopyridin-5-yl]-6-[(R/S)-3-methanesulfonyloxy-2-hydroxy propoxy]benzothiophene (15-2, 117 mg, 0.230 mmol) obtained in step 3.

$^1$H NMR (400 MHz, CDCl$_3$) δ 1.55 (s, 9H), 1.56-1.61 (m, 4H), 1.74-1.86 (m, 2H), 3.05 (s, 1.5H), 3.10 (s, 1.5H), 3.44 (s, 3H), 3.54-3.59 (m, 1H), 3.93-4.09 (m, 2H), 4.11-4.22 (m, 2H), 4.26-4.44 (m, 2H), 4.49-4.59 (m, 1H), 4.83-4.88 (m,

1H), 7.00 (dt, J=8.8, 2.8 Hz, 1H), 7.34 (dd, J=8.4, 2.0 Hz, 1H), 7.43 (s, 1H), 7.66 (d, J=8.4 Hz, 1H), 7.77 (d, J=8.4 Hz, 1H), 7.86 (dd, J=8.4, 2.4 Hz, 1H), 8.67 (d, J=2.4 Hz, 1H);

$^{13}$C NMR (100 MHz, CDCl$_3$) δ 19.5, 25.2, 28.3, 29.7, 30.57, 30.63, 34.1, 37.46, 37.50, 62.9, 66.8, 67.3, 68.9, 69.5, 72.6, 73.0, 81.4, 98.9, 99.3, 105.9, 106.0, 114.9, 118.7, 119.4, 124.3, 125.8, 134.3, 134.9, 135.0, 138.0, 138.1, 140.9, 144.5, 154.2, 154.8, 156.2, 156.3.

Steps 5 and 6: Preparation of 2-[2-(N-monomethyl)aminopyridin-5-yl]-6-[(R/S)-3-fluoro-2-hydroxypropoxy]benzothiophene 2-[2-(N-Methyl-N—BOC)aminopyridin-5-yl]-6-[(R/S)-3-methanesulfonyloxy-2-(tetrahydropyran-2-yloxy)propoxy]benzothiophene (16-2, 80 mg, 0.135 mmol) obtained in step 4 and tetrabutylammonium fluoride (TBAF; 43 mg, 0.162 mmol) were dissolved in t-amyl alcohol (3 mL) and agitated at 100° C. for 6 hours. After cooling to room temperature, removing the solvent under reduced pressure and adding 4 M HCl (0.27 mL) and tetrahydrofuran (1.08 mL), the target compound 2-[2-(N-monomethyl)aminopyridin-5-yl]-6-[(R/S)-3-fluoro-2-hydroxypropoxy]benzothiophene (1-2, 35 mg, 78%) was obtained in the same manner as steps 5 and 6 of Example 1 (see FIG. 1).

$^1$H NMR (400 MHz, THF-d$_8$) δ 3.59 (s, 3H), 4.10-4.19 (m, 3H), 4.40-4.61 (m, 2H), 4.81 (br s, 1H), 6.01 (br s, 1H), 6.42 (d, J=8.8 Hz, 1H), 6.95 (d, J=8.4 Hz, 1H), 7.33 (s, 1H), 7.41 (s, 1H), 7.58 (d, J=8.8 Hz, 1H), 7.67 (d, J=8.8 Hz, 1H), 8.37 (s, 1H);

$^{13}$C NMR (100 MHz, THF-d$_8$) δ 28.6, 69.5 (d, J=20.1 Hz), 69.7 (d, J=7.5 Hz), 85.2 (d, J=168.9 Hz), 106.6, 107.7, 115.3, 117.3, 119.7, 124.2, 134.9, 136.2, 140.7, 141.0, 146.5, 157.3, 160.3.

Example 2-1

Preparation of 2-[2-(N-monomethyl)aminopyridin-5-yl]-6-[(R/S)-3-fluoro-2-hydroxypropoxy]benzothiophene Step 1': Preparation of 2-[2-(N-methyl-N—BOC)aminopyridin-5-yl]-6-[(R/S)-(2,2-dimethyl-1,3-dioxolan-4-yl)methyloxy]benzothiophene 6-[(R/S)-(2,2-Dimethyl-1,3-dioxolan-4-yl)methyloxy]benzothiophene-2-boronic acid ((R/S)-26, 315 mg, 1.022 mmol) prepared in Preparation Example 6 dissolved in PEG 400 (5 mL) was slowly added to 2-(N-methyl-N—BOC)amino-5-iodopyridine (28, 410 mg, 1.227 mmol), K$_2$CO$_3$ (212 mg, 1.533 mmol) and Pd(OAc)$_2$ (11 mg, 0.045 mmol) dissolved in PEG 400 (5 mL) at room temperature. After agitating the reaction mixture at room temperature for 3 hours and adding water, the organic compound was extracted with ethyl acetate. After treating the collected ethyl acetate solution with sodium sulfate, column chromatography yielded the target compound 2-[2-(N-methyl-N—BOC)aminopyridin-5-yl]-6-[(R/S)-(2,2-dimethyl-1,3-dioxolan-4-yl) methyloxy] benzothiophene ((R/S)-19-1, 200 mg, 42%).

$^1$H NMR (400 MHz, CDCl$_3$) δ 1.42 (s, 3H), 1.49 (s, 3H), 1.54 (s, 9H), 3.44 (s, 3H), 3.92-3.95 (m, 1H), 3.99-4.03 (m, 1H), 4.11-4.14 (m, 1H), 4.17-4.21 (m, 1H), 4.49-4.55 (m, 1H), 7.01 (dd, J=8.8, 2.4 Hz, 1H), 7.31 (d, J=2.4 Hz, 1H), 7.42 (s, 1H), 7.65 (d, J=8.8 Hz, 1H), 7.77 (d, J=8.8 Hz, 1H), 7.85 (dd, J=8.8, 2.8 Hz, 1H), 8.67 (d, J=2.4 Hz, 1H);

$^{13}$C NMR (100 MHz, CDCl$_3$) δ 25.6, 27.1, 28.6, 34.4, 67.1, 69.5, 74.2, 81.7, 106.1, 110.1, 115.3, 118.9, 119.7, 124.5, 126.1, 134.5, 135.1, 138.2, 141.1, 144.8, 154.5, 154.7, 156.8.

Step 2': Preparation of 2-[2-(N-methyl-N—BOC)aminopyridin-5-yl]-6-[(R/S)-2,3-dihydroxypropoxy]benzothiophene

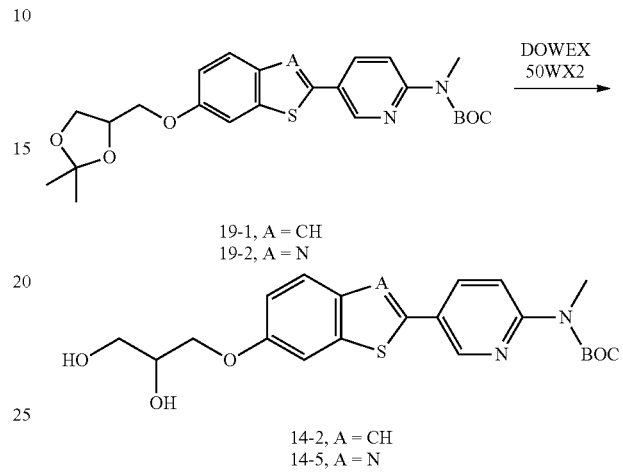

19-1, A = CH
19-2, A = N 14-2, A = CH
14-5, A = N

After adding Dowex 50WX2 (66 mg) resin to 2-[2-(N-methyl-N—BOC)aminopyridin-5-yl]-6-[(R/S)-(2,2-dimethyl-1,3-dioxolan-4-yl)methyloxy]benzothiophene ((R/S)-19-1, 60 mg, 0.128 mmol) obtained in step 1' dissolved in 10% H$_2$O/MeOH (2 mL), the reaction mixture was agitated at 40° C. for 25 hours. After filtering the reaction mixture and removing the solvent under reduced pressure, column chromatography yielded the target compound 2-[2-(N-methyl-N—BOC)aminopyridin-5-yl]-6-[(R/S)-2,3-dihydroxypropoxy]benzothiophene (14-2, 32 mg, 58%).

$^1$H NMR (400 MHz, CDCl$_3$) δ 1.55 (s, 9H), 3.43 (s, 3H), 3.79 (d, J=4.6 Hz, 1H), 3.84 (d, J=3.6 Hz, 1H), 4.10 (s, 3H), 6.98 (dd, J=8.8, 2.2 Hz, 1H), 7.29 (d, J=2.2 Hz, 1H), 7.34 (s, 1H), 7.62 (d, J=8.8 Hz, 1H), 7.74 (d, J=8.8 Hz, 1H), 7.84 (dd, J=8.8, 2.6 Hz, 1H), 8.64 (d, J=2.6 Hz, 1H);

$^{13}$C NMR (100 MHz, CDCl$_3$) δ 28.3, 29.7, 34.2, 63.9, 69.6, 70.4, 81.5, 105.9, 114.8, 118.7, 119.4, 124.3, 125.9, 134.2, 134.9, 137.9, 140.9, 144.5, 154.3, 154.4, 156.4.

Steps 3 to 6: Preparation of 2-[2-(N-monomethyl)aminopyridin-5-yl]-6-[(R/S)-3-fluoro-2-hydroxypropoxy]benzothiophene The target compound (35 mg, 78%) was obtained in the same manner as steps 3 to 6 of Example 2 except for using 2-[2-(N-methyl-N—BOC)aminopyridin-5-yl]-6-[(R/S)-3-fluoro-2-hydroxypropoxy]benzothiophene (470 mg, 1.10 mmol) prepared in step 2'.

$^1$H NMR (400 MHz, THF-d$_8$) δ 3.59 (s, 3H), 4.10-4.19 (m, 3H), 4.40-4.61 (m, 2H), 4.81 (br s, 1H), 6.01 (br s, 1H), 6.42 (d, J=8.8 Hz, 1H), 6.95 (d, J=8.4 Hz, 1H), 7.33 (s, 1H), 7.41 (s, 1H), 7.58 (d, J=8.8 Hz, 1H), 7.67 (d, J=8.8 Hz, 1H), 8.37 (s, 1H);

$^{13}$C NMR (100 MHz, THF-d$_8$) δ 28.6, 69.5 (d, J=20.1 Hz), 69.7 (d, J=7.5 Hz), 85.2 (d, J=168.9 Hz), 106.6, 107.7, 115.3, 117.3, 119.7, 124.2, 134.9, 136.2, 140.7, 141.0, 146.5, 157.3, 160.3.

Example 3

Preparation of 2-[2-(N-monomethyl)aminopyridin-5-yl]-6-[(S)-3-fluoro-2-hydroxypropoxy]benzothiophene

Step 1': Preparation of 2-[2-(N-methyl-N—BOC)aminopyridin-5-yl]-6-[(S)-(2,2-dimethyl-1,3-dixolan-4-yl)methyloxy]benzothiophene The target compound 2-[2-(N-methyl-N—BOC)aminopyridin-5-yl]-6-[(S)-(2,2-dimethyl-1,3-dioxolan-4-yl)methyloxy]benzothiophene ((S)-19-1, 1.00 g, 76%) was obtained in the same manner as step 1 of Example 2-1 using 6-[(S)-(2,2-dimethyl-1,3-dioxolan-4-yl)methyloxy]benzothiophene-2-boronic acid ((S)-26, 860 mg, 2.79 mmol) obtained in Preparation Example 7, 2-(N-methyl-N—BOC)amino-5-iodopyridine (1.40 mg, 4.19 mmol), $K_2CO_3$ (771 mg, 5.58 mmol) and $Pd(OAc)_2$ (31 mg, 0.127 mmol).

$^1$H NMR (400 MHz, $CDCl_3$) δ 1.42 (s, 3H), 1.49 (s, 3H), 1.54 (s, 9H), 3.44 (s, 3H), 3.92-3.95 (m, 1H), 3.99-4.03 (m, 1H), 4.11-4.14 (m, 1H), 4.17-4.21 (m, 1H), 4.49-4.55 (m, 1H), 7.01 (dd, J=8.8, 2.4 Hz, 1H), 7.31 (d, J=2.4 Hz, 1H), 7.42 (s, 1H), 7.65 (d, J=8.8 Hz, 1H), 7.77 (d, J=8.8 Hz, 1H), 7.85 (dd, J=8.8, 2.8 Hz, 1H), 8.67 (d, J=2.4 Hz, 1H);
$^{13}$C NMR (100 MHz, $CDCl_3$) δ 25.6, 27.1, 28.6, 34.4, 67.1, 69.5, 74.2, 81.7, 106.1, 110.1, 115.3, 118.9, 119.7, 124.5, 126.1, 134.5, 135.1, 138.2, 141.1, 144.8, 154.5, 154.7, 156.8.

Step 2': Preparation of 2-[2-(N-methyl-N—BOC)aminopyridin-5-yl]-6-[(R)-2,3-dihydroxypropoxy]benzothiophene 2-[2-(N-Methyl-N—BOC)aminopyridin-5-yl]-6-[(R)-2,3-dihydroxypropoxy]benzothiophene ((R)-14-2, 160 mg, 20%) was obtained in the same manner as step 2' of Example 2 except that 2-[2-(N-methyl-N—BOC)aminopyridin-5-yl]-6-[(S)-(2,2-dimethyl-1,3-dioxolan-4-yl)methyloxy]benzothiophene ((S)-19-1, 900 mg, 1.91 mmol) obtained in step 1' and Dowex 50WX2 (900 mg) resin were used.

$^1$H NMR (400 MHz, $CDCl_3$) δ 1.55 (s, 9H), 3.43 (s, 3H), 3.79 (d, J=4.6 Hz, 1H), 3.84 (d, J=3.6 Hz, 1H), 4.10 (s, 3H), 6.98 (dd, J=8.8, 2.2 Hz, 1H), 7.29 (d, J=2.2 Hz, 1H), 7.34 (s, 1H), 7.62 (d, J=8.8 Hz, 1H), 7.74 (d, J=8.8 Hz, 1H), 7.84 (dd, J=8.8, 2.6 Hz, 1H), 8.64 (d, J=2.6 Hz, 1H);
$^{13}$C NMR (100 MHz, $CDCl_3$) δ 28.3, 29.7, 34.2, 63.9, 69.6, 70.4, 81.5, 105.9, 114.8, 118.7, 119.4, 124.3, 125.9, 134.2, 134.9, 137.9, 140.9, 144.5, 154.3, 154.4, 156.4.

Step 3: Preparation of 2-[2-(N-methyl-N—BOC)aminopyridin-5-yl]-6-[(S)-3-methanesulfonyloxy-2-hydroxypropoxy]benzothiophene The target compound 2-[2-(N-methyl-N—BOC)aminopyridin-5-yl]-6-[(S)-3-methanesulfonyloxy-2-hydroxypropoxy]benzothiophene ((S)-15-2, 118 mg, 62%) was obtained in the same manner as in step 3 of Example 1 using 2-[2-(N-methyl-N—BOC)aminopyridin-5-yl]-6-((R)-2,3-dihydroxypropoxy)benzothiophene ((R)-14-2, 160 mg, 0.372 mmol) obtained in step 2', diisopropylethylamine (DIPEA; 0.097 mL, 0.557 mmol) and methanesulfonyl chloride (MsCl; 0.032 mL, 0.409 mmol).

$^1$H NMR (400 MHz, $CDCl_3+CD_3OD$) δ 1.55 (s, 9H), 3.01 (s, 3H), 3.43 (s, 3H), 4.12 (d, J=5.2 Hz, 2H), 4.30-4.51 (m, 3H), 7.50 (dd, J=8.8, 2.2 Hz, 1H), 7.43 (s, 1H), 7.66 (d, J=8.8 Hz, 1H), 7.75 (d, J=8.8 Hz, 1H), 7.87 (dd, J=9.2, 2.6 Hz, 1H), 8.66 (d, J=2.2 Hz, 1H);
$^{13}$C NMR (100 MHz, $CDCl_3$) δ 28.2, 34.2, 37.5, 67.9, 68.4, 70.5, 81.5, 106.0, 114.8, 118.8, 119.4, 124.4, 125.9, 134.3, 135.1, 138.1, 140.9, 144.5, 154.3, 154.4, 156.0.

Step 4: Preparation of 2-[2-(N-methyl-N—BOC)aminopyridin-5-yl]-6-[(S)-3-methanesulfonyloxy-2-(tetrahydro pyran-2-yloxy)propoxy]benzothiophene The target compound 2-[2-(N-methyl-N—BOC)aminopyridin-5-yl]-6-[(S)-3-methanesulfonyloxy-2-(tetrahydro pyran-2-yloxy)propoxy]benzothiophene ((S)-16-2, 100 mg, 78%) was obtained in the same manner as in step 4 of Example 1 except that 2-[2-(N-methyl-N—BOC)aminopyridin-5-yl]-6-[(S)-3-methanesulfonyloxy-2-hydroxypropoxy]benzothiophene ((S)-15-2, 110 mg, 0.216 mmol) obtained in step 3, dihydropyran (DHP; 0.040 mL, 0.432 mmol) and pyridinium p-toluenesulfonate (PPTS; 11 mg, 0.042 mmol) were used.

$^1$H NMR (400 MHz, $CDCl_3$) δ 1.55 (s, 9H), 1.56-1.61 (m, 4H), 1.74-1.86 (m, 2H), 3.05 (s, 1.5H), 3.10 (s, 1.5H), 3.44 (s, 3H), 3.54-3.59 (m, 1H), 3.93-4.09 (m, 2H), 4.11-4.22 (m, 2H), 4.26-4.44 (m, 2H), 4.49-4.59 (m, 1H), 4.83-4.88 (m, 1H), 7.00 (dt, J=8.8, 2.8 Hz, 1H), 7.34 (dd, J=8.4, 2.0 Hz, 1H), 7.43 (s, 1H), 7.66 (d, J=8.4 Hz, 1H), 7.77 (d, J=8.4 Hz, 1H), 7.86 (dd, J=8.4, 2.4 Hz, 1H), 8.67 (d, J=2.4 Hz, 1H);
$^{13}$C NMR (100 MHz, $CDCl_3$) δ 19.5, 25.2, 28.3, 29.7, 30.57, 30.63, 34.1, 37.46, 37.50, 62.9, 66.8, 67.3, 68.9, 69.5, 72.6, 73.0, 81.4, 98.9, 99.3, 105.9, 106.0, 114.9, 118.7, 119.4, 124.3, 125.8, 134.3, 134.9, 135.0, 138.0, 138.1, 140.9, 144.5, 154.2, 154.8, 156.2, 156.3.

Figure 2:
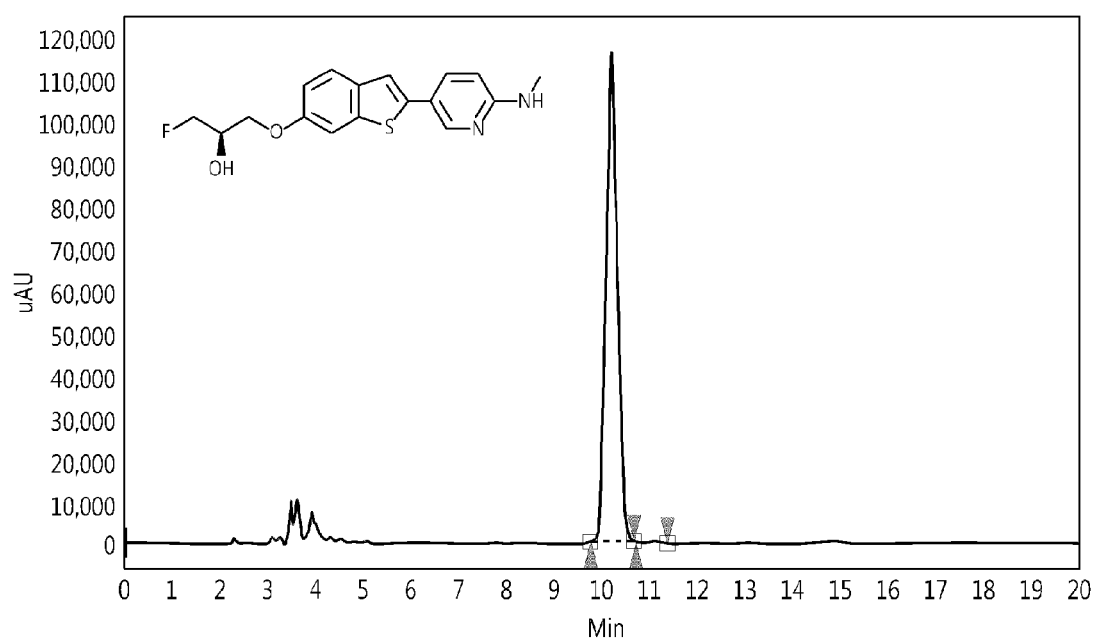
FIG. 2 shows a result of chiral HPLC analysis/purification of a compound of Example 3 ((S)-1-2)

Steps 5 and 6: Preparation of 2-[2-(N-monomethyl)aminopyridin-5-yl]-6-[(S)-3-fluoro-2-hydroxypropoxy]benzothiophene 2-[2-(N-Methyl-N—BOC)aminopyridin-5-yl]-6-[(S)-3-methanesulfonyloxy-2-(tetrahydropyran-2-yloxy)propoxy]benzothiophene ((S)-16-2, 170 mg, 0.287 mmol) obtained in step 4 and tetrabutylammonium fluoride (TBAF; 92 mg, 0.344 mmol) were dissolved in t-amyl alcohol (3 mL) and agitated at 100° C. for 6 hours. After cooling to room temperature, removing the solvent under reduced pressure and adding 4 M HCl (0.6 mL) and tetrahydrofuran (2.0 mL), the target compound 2-[2-(N-monomethyl)aminopyridin-5-yl]-6-[(S)-3-fluoro-2-hydroxypropoxy]benzothiophene ((S)-1-2, 72 mg, 76%) was obtained in the same manner as in steps 5 and 6 of Example 1 (see FIG. 2).

$^1$H NMR (400 MHz, TI-IF-$d_8$) δ 3.59 (s, 3H), 4.10-4.19 (m, 3H), 4.40-4.61 (m, 2H), 4.81 (br s, 1H), 6.01 (br s, 1H), 6.42 (d, J=8.8 Hz, 1H), 6.95 (d, J=8.4 Hz, 1H), 7.33 (s, 1H), 7.41 (s, 1H), 7.58 (d, J=8.8 Hz, 1H), 7.67 (d, J=8.8 Hz, 1H), 8.37 (s, 1H);
$^{13}$C NMR (100 MHz, THF-dg) δ 28.6, 69.5 (d, J=20.1 Hz), 69.7 (d, J=7.5 Hz), 85.2 (d, J=168.9 Hz), 106.6, 107.7, 115.3, 117.3, 119.7, 124.2, 134.9, 136.2, 140.7, 141.0, 146.5, 157.3, 160.3.

Example 4

Preparation of 2-[2-(N-monomethyl)aminopyridin-5-yl]-6-[(R)-3-fluoro-2-hydroxypropoxy]benzothiophene

Step 1': Preparation of 2-[2-(N-methyl-N—BOC)aminopyridin-5-yl]-6-[(R)-(2,2-dimethyl-1,3-dioxolan-4-methyloxy]benzothiophene The target compound 2-[2-(N-methyl-N—BOC)aminopyridin-5-yl]-6-[(R)-(2,2-dimethyl-1,3-dioxolan-4-yl)methyloxy]benzothiophene ((R)-19-1, 650 mg, 76%) was obtained in the same manner as in step 1 of Example 2-1 using 6-[(R)-(2,2-dimethyl-1,3-dioxolan-4-yl)methyloxy]benzothiophene-2-boronic acid ((R)-26, 560 mg, 1.82 mmol), 2-(N-methyl-N—BOC)amino-5-iodopyridine (911 mg, 2.73 mmol), $K_2CO_3$ (502 mg, 3.63 mmol) and $Pd(OAc)_2$ (20 mg, 0.082 mmol).

$^1$H NMR (400 MHz, $CDCl_3$) δ 1.42 (s, 3H), 1.49 (s, 3H), 1.54 (s, 9H), 3.44 (s, 3H), 3.92-3.95 (m, 1H), 3.99-4.03 (m, 1H), 4.11-4.14 (m, 1H), 4.17-4.21 (m, 1H), 4.49-4.55 (m, 1H), 7.01 (dd, J=8.8, 2.4 Hz, 1H), 7.31 (d, J=2.4 Hz, 1H), 7.42 (s, 1H), 7.65 (d, J=8.8 Hz, 1H), 7.77 (d, J=8.8 Hz, 1H), 7.85 (dd, J=8.8, 2.8 Hz, 1H), 8.67 (d, J=2.4 Hz, 1H);

$^{13}$C NMR (100 MHz, $CDCl_3$) δ 25.6, 27.1, 28.6, 34.4, 67.1, 69.5, 74.2, 81.7, 106.1, 110.1, 115.3, 118.9, 119.7, 124.5, 126.1, 134.5, 135.1, 138.2, 141.1, 144.8, 154.5, 154.7, 156.8.

Step 2': Preparation of 2-[2-(N-methyl-N—BOC) aminopyridin-5-yl]-6-[(S)-2,3-dihydroxypropoxy] benzothiophene 2-[2-(N-Methyl-N—BOC)aminopyridin-5-yl]-6-[(S)-2,3-dihydroxypropoxy]benzothiophene ((S)-14-2, 300 mg, 39%) was obtained in the same manner as in step 2' of Example 2 except that 2-[2-(N-methyl-N—BOC)aminopyridin-5-yl]-6-[(R)-(2,2-dimethyl-1,3-dioxolan-4-yl)methyloxy]benzothiophene ((R)-19-1, 850 mg, 1.806 mmol) obtained in step 1' and Dowex 50WX2 (850 mg) resin were used.

$^1$H NMR (400 MHz, $CDCl_3$) δ 1.55 (s, 9H), 3.43 (s, 3H), 3.79 (d, J=4.6 Hz, 1H), 3.84 (d, J=3.6 Hz, 1H), 4.10 (s, 3H), 6.98 (dd, J=8.8, 2.2 Hz, 1H), 7.29 (d, J=2.2 Hz, 1H), 7.34 (s, 1H), 7.62 (d, J=8.8 Hz, 1H), 7.74 (d, J=8.8 Hz, 1H), 7.84 (dd, J=8.8, 2.6 Hz, 1H), 8.64 (d, J=2.6 Hz, 1H);

$^{13}$C NMR (100 MHz, $CDCl_3$) δ 28.3, 29.7, 34.2, 63.9, 69.6, 70.4, 81.5, 105.9, 114.8, 118.7, 119.4, 124.3, 125.9, 134.2, 134.9, 137.9, 140.9, 144.5, 154.3, 154.4, 156.4.

Step 3: Preparation of 2-[2-(N-methyl-N—BOC) aminopyridin-5-yl]-6-[(R)-3-methanesulfonyloxy-2-hydroxypropoxy]benzothiophene The target compound 2-[2-(N-methyl-N—BOC)aminopyridin-5-yl]-6-[(R)-3-methanesulfonyloxy-2-hydroxypropoxy]benzothiophene ((R)-15-2, 430 mg, 77%) was obtained in the same manner as in step 3 of Example 1 using 2-[2-(N-methyl-N—BOC)aminopyridin-5-yl]-6-((S)-2,3-dihydroxypropoxy)benzothiophene ((S)-14-2, 300 mg, 0.697 mmol) obtained in step 2', diisopropylethylamine (DIPEA; 0.146 mL, 0.836 mmol) and methanesulfonyl chloride (MsCl; 0.059 mL, 0.767 mmol).

$^1$H NMR (400 MHz, $CDCl_3$+$CD_3OD$) δ 1.55 (s, 9H), 3.01 (s, 3H), 3.43 (s, 3H), 4.12 (d, J=5.2 Hz, 2H), 4.30-4.51 (m, 3H), 7.50 (dd, J=8.8, 2.2 Hz, 1H), 7.43 (s, 1H), 7.66 (d, J=8.8 Hz, 1H), 7.75 (d, J=8.8 Hz, 1H), 7.87 (dd, J=9.2, 2.6 Hz, 1H), 8.66 (d, J=2.2 Hz, 1H);

$^{13}$C NMR (100 MHz, $CDCl_3$) δ 28.2, 34.2, 37.5, 67.9, 68.4, 70.5, 81.5, 106.0, 114.8, 118.8, 119.4, 124.4, 125.9, 134.3, 135.1, 138.1, 140.9, 144.5, 154.3, 154.4, 156.0.

Step 4: Preparation of 2-[2-(N-methyl-N—BOC) aminopyridin-5-yl]-6-[(R)-3-methanesulfonyloxy-2-(tetrahydropyran-2-yloxy)propoxy]benzothiophene The target compound 2-[2-(N-methyl-N—BOC)aminopyridin-5-yl]-6-[(R)-3-methanesulfonyloxy-2-(tetrahydropyran-2-yloxy)propoxy]benzothiophene ((R)-16-2, 200 mg, 95%) was obtained in the same manner as in step 4 of Example 1 except that 2-[2-(N-methyl-N—BOC)aminopyridin-5-yl]-6-[(R)-3-methanesulfonyloxy-2-hydroxypropoxy]benzothiophene ((R)-15-2, 180 mg, 0.354 mmol) obtained in step 3, dihydropyran (DHP; 0.067 mL, 0.708 mmol) and pyridinium p-toluenesulfonate (PPTS; 18 mg, 0.069 mmol) were used.

$^1$H NMR (400 MHz, $CDCl_3$) δ 1.55 (s, 9H), 1.56-1.61 (m, 4H), 1.74-1.86 (m, 2H), 3.05 (s, 1.5H), 3.10 (s, 1.5H), 3.44 (s, 3H), 3.54-3.59 (m, 1H), 3.93-4.09 (m, 2H), 4.11-4.22 (m, 2H), 4.26-4.44 (m, 2H), 4.49-4.59 (m, 1H), 4.83-4.88 (m, 1H), 7.00 (dt, J=8.8, 2.8 Hz, 1H), 7.34 (dd, J=8.4, 2.0 Hz, 1H), 7.43 (s, 1H), 7.66 (d, J=8.4 Hz, 1H), 7.77 (d, J=8.4 Hz, 1H), 7.86 (dd, J=8.4, 2.4 Hz, 1H), 8.67 (d, J=2.4 Hz, 1H);

$^{13}$C NMR (100 MHz, $CDCl_3$) δ 19.5, 25.2, 28.3, 29.7, 30.57, 30.63, 34.1, 37.46, 37.50, 62.9, 66.8, 67.3, 68.9, 69.5, 72.6, 73.0, 81.4, 98.9, 99.3, 105.9, 106.0, 114.9, 118.7, 119.4, 124.3, 125.8, 134.3, 134.9, 135.0, 138.0, 138.1, 140.9, 144.5, 154.2, 154.8, 156.2, 156.3.

Steps 5 and 6: Preparation of 2-[2-(N-monomethyl) aminopyridin-5-yl]-6-[R)-3-fluoro-2-hydroxypropoxy]benzothiophene 2-[2-(N-Methyl-N—BOC)aminopyridin-5-yl]-6-[(R)-3-methanesulfonyloxy-2-(tetrahydropyran-2-yloxy)propoxy]benzothiophene ((R)-16-2, 140 mg, 0.236 mmol) obtained in step 4 and tetrabutylammonium fluoride (TBAF; 76 mg, 0.283 mmol) were dissolved in t-amyl alcohol (3 mL) and then agitated at 100° C. for 6 hours. After cooling to room temperature, removing the solvent under reduced pressure and adding 4 M HCl (0.5 mL) and tetrahydrofuran (4.0 mL), the target compound 2-[2-(N-monomethyl)aminopyridin-5-yl]-6-[(R)-3-fluoro-2-hydroxypropoxy]benzothiophene ((R)-1-2, 55 mg, 70%) was obtained in the same manner as in steps 5 and 6 of Example 1 (see FIG. 3).

$^1$H NMR (400 MHz, THF-$d_8$) δ 3.59 (s, 3H), 4.10-4.19 (m, 3H), 4.40-4.61 (m, 2H), 4.81 (br s, 1H), 6.01 (br s, 1H), 6.42 (d, J=8.8 Hz, 1H), 6.95 (d, J=8.4 Hz, 1H), 7.33 (s, 1H), 7.41 (s, 1H), 7.58 (d, J=8.8 Hz, 1H), 7.67 (d, J=8.8 Hz, 1H), 8.37 (s, 1H);

$^{13}$C NMR (100 MHz, THF-$d_8$) δ 28.6, 69.5 (d, J=20.1 Hz), 69.7 (d, J=7.5 Hz), 85.2 (d, J=168.9 Hz), 106.6, 107.7, 115.3, 117.3, 119.7, 124.2, 134.9, 136.2, 140.7, 141.0, 146.5, 157.3, 160.3.

Example 5

Preparation of 2-[3-(N-monomethyl)aminopyridazin-6-yl]-6-[(R/S)-3-fluoro-2-hydroxypropoxy]benzothiophene Step 1: Preparation of 2-[3-(N-methyl-N—BOC) aminopyridazin-6-yl]-6-allyloxybenzothiophene 2-[3-(N-Methyl-N—BOC)aminopyridazin-6-yl]-6-allyloxybenzothiophene (13-3) was prepared in the same manner as step 1 of Example 1 using 2-[3-(N-methyl-N—BOC)aminopyridazin-6-yl]-6-hydroxybenzothiophene (12-3, 628 mg, 1.73 mmol) obtained in Preparation Example 3, allyl bromide (251 mg, 2.07 mmol) and $Cs_2CO_3$ (1.2 g, 3.46 mmol). The compound thus prepared was used in the subsequent step without purification.

Step 2: Preparation of 2-[3-(N-methyl-N—BOC) aminopyridazin-6-yl]-6-((R/S)-2,3-dihydroxypropoxy)benzothiophene After sequentially adding osmium tetroxide (4 wt % in $H_2O$, 0.108 mL, 0.017 mmol), N-methylmorpholine N-oxide (304 mg, 2.595 mmol) and DABCO (4 mg, 0.034 mmol) to 2-[3-(N-methyl-N—BOC)aminopyridazin-6-yl]-6-allyloxybenzothiophene (13-3) prepared in step 1, the target compound 2-[3-(N-methyl-N—BOC)aminopyridazin-6-yl]-6-((R/S)-2,3-dihydroxypropoxy)benzothiophene (14-3, 256 mg, 34%) was obtained in the same manner as in step 2 of Example 1.

$^1$H NMR (200 MHz, CDCl$_3$) δ 1.56 (s, 9H), 3.60 (s, 3H), 3.82 (m, 2H), 4.09 (m, 3H), 7.00 (dd, J=2.2, 1.1 Hz, 1H), 7.37 (d, J=2.2 Hz, 1H), 7.73 (m, 3H), 8.14 (d, J=9.6 Hz, 1H);

$^{13}$C NMR (100 MHz, CDCl$_3$) δ 28.5, 34.6, 63.9, 69.8, 70.6, 82.6, 106.1, 115.4, 122.1, 123.1, 123.3, 125.2, 134.6, 138.7, 142.8, 151.7, 154.1, 157.1, 157.4.

Step 3: Preparation of 2-[3-(N-methyl-N—BOC) aminopyridazin-6-yl]-6-[(R/S)-3-methanesulfonyloxy-2-hydroxypropoxy]benzothiophene The target compound 2-[3-(N-methyl-N—BOC)aminopyridazin-6-yl]-6-β-methanesulfonyloxy-2-hydroxyprop oxy) benzothiophene (15-3, 139 mg, 50%) was obtained in the same manner as in step 3 of Example 1 using 2-[3-(N-methyl-N—BOC)aminopyridazin-6-yl]-6-((R/S)-2,3-dihydroxypropoxy)benzothiophene (14-3, 236 mg, 0.550 mmol) obtained in step 2, methanesulfonyl chloride (MsCl; 0.047 mL, 0.601 mmol) and diisopropylethylamine (0.114 mL, 0.660 mmol), and was immediately subjected to the following reaction.

Step 4: Preparation of 2-[3-(N-methyl-N—BOC) aminopyridazin-6-yl]-6-[(R/S)-3-methanesulfonyloxy-2-(tetrahydropyran-2-yloxy)propoxy]benzothiophene The target compound 2-[3-(N-methyl-N—BOC)aminopyridazin-6-yl]-6-[(R/S)-3-methanesulfonyloxy-2-(tetrahydropyran-2-yloxy)propoxy]benzothiophene (16-3, 132 mg, 82%) was obtained in the same manner as in step 4 of Example 1 except that 2-[3-(N-methyl-N—BOC)aminopyridazin-6-yl]-6-[(R/S)-3-methanesulfonyloxy-2-hydroxypropoxy]benzothiophene (15-3, 139 mg, 0.270 mmol) obtained in step 3, dihydropyran (DHP; 0.040 mL, 0.540 mmol) and pyridinium p-toluenesulfonate (PPTS; 14 mg, 0.054 mmol) were used.

$^1$H NMR (200 MHz, CDCl$_3$) δ 1.53 (s, 9H), 3.02 (d, J=5.2 Hz, 3H), 3.6 (s, 3H), 4.3 (m., 8H), 4.9 (s, 1H), 7.00 (d, J=8.0 Hz, 1H), 7.32 (dd, J=8.0, 2.2 Hz, 1H), 7.7 (m, 3H), 8.13 (d, J=9.6 Hz, 1H);

$^{13}$C NMR (50 MHz, CDCl$_3$) δ 19.8, 25.5, 28.5, 30.8, 30.9, 34.6, 37.7, 37.8, 63.2, 66.9, 67.4, 69.1, 69.8, 72.7, 73.2, 82.6, 99.2, 99.6, 106.0, 106.2, 115.37, 115.40, 122.0, 123.0, 123.3, 125.20, 125.22, 134.6, 134.7, 142.8, 151.7, 154.1, 157.1, 157.2, 157.3.

Steps 5 and 6: Preparation of 2-[3-(N-monomethyl) aminopyridazin-6-yl]-6-[(R/S)-3-fluoro-2-hydroxypropoxy]benzothiophene 2-[3-(N-Methyl-N—BOC)aminopyridazin-6-yl]-6-[(R/S)-3-methanesulfonyloxy-2-(tetrahydropyran-2-yloxy)propoxy]benzothiophene (16-3, 132 mg, 0.22 mmol) obtained in step 4 and tetrabutylammonium fluoride (TBAF; 87 mg, 0.33 mmol) were dissolved in t-amyl alcohol (3 mL) and then agitated at 100° C. for 6 hours. After cooling to room temperature, removing the solvent under reduced pressure, and adding 4 M HCl (0.6 mL) and tetrahydrofuran (2.0 mL), the target compound 2-[3-(N-monomethyl)aminopyridazin-6-yl]-6-[(R/S)-3-fluoro-2-hydroxypropoxy]benzothiophene (1-3, 63 mg, 86%) was obtained in the same manner as steps 5 and 6 of Example 1.

$^1$H NMR (200 MHz, acetone-d$_6$) δ 3.03 (d, J=1.4 Hz, 3H), 4.17 (m, 2H), 4.32 (m, 1H), 4.48 (m, 1H), 4.70 (m, 1H), 6.29 (br s, 1H), 6.92 (d, J=9.6 Hz, 1H), 6.99 (dd, J=8.8, 2.2, 8.8 Hz, 1H), 7.53 (d, J=2.6 Hz, 1H), 7.71 (d, J=9.4 Hz, 2H), 7.86 (d, J=9.0 Hz, 1H);

$^{13}$C NMR (100 MHz, CDCl$_3$ & CD$_3$OD) δ 30.2, 68.3 (d, J=7.4 Hz), 68.6 (d, J=19.4 Hz), 84.1 (d, J=169 Hz), 106.0, 114.7, 114.9, 119.7, 124.6, 124.9, 125.5, 134.7, 139.7, 141.9, 147.2, 156.9, 158.7.

Example 6

Preparation of 2-[4-(N-monomethyl)aminophenyl]-6-[(R/S)-3-fluoro-2-hydroxypropoxy]benzothiazole

Step 1: Preparation of 2-[4-(N-methyl-N—BOC) aminophenyl]-6-allyloxybenzothiazole 2-[4-(N-Methyl-N—BOC)aminophenyl]-6-allyloxybenzothiazole (13-4) was prepared in the same manner as step 1 of Example 1 using 2-[4-(N-monomethyl)aminophenyl)-6-hydroxybenzothiazole (12-4, 519 mg, 1.46 mmol) obtained in Preparation Example 4, allyl bromide (0.152 mL, 1.75 mmol) and Cs$_2$CO$_3$ (951 mg, 2.92 mmol). Thus prepared compound was used in the subsequent step without purification.

Step 2: Preparation of 2-[3-(N-methyl-N—BOC) aminopyridazin-6-yl]-6-((R/S)-2,3-dihydroxypropoxy)benzothiophene After sequentially adding osmium tetroxide (4 wt % in H$_2$O, 0.092 mL, 0.015 mmol), N-methylmorpholine N-oxide (256 mg, 2.190 mmol) and DABCO (4 mg, 0.030 mmol) to 2-[4-(N-methyl-N—BOC)aminophenyl]-6-allyloxybenzothiazole (13-4) prepared in step 1, the target compound 2-[4-(N-methyl-N—BOC)aminophenyl]-6-((R/S)-2,3-dihydroxypropoxy)benzothiazole (14-4, 495 mg, 78%) was obtained in the same manner as step 2 of Example 1.

$^1$H NMR (200 MHz, acetone-d$_6$) δ 8.03 (d, J=8.8 Hz, 2H), 7.90 (d, J=9.0 Hz, 1H), 7.62 (d, J=2.2 Hz, 1H), 7.49 (d, J=8.4 Hz, 2H), 7.15 (dd, J=8.8, 2.2 Hz, 1H), 4.24-4.01 (m, 4H), 3.90-3.84 (m, 1H), 3.73-3.66 (m, 2H), 3.31 (s, 3H), 1.47 (s, 9H);

$^{13}$C NMR (50 MHz, acetone-d$_6$) δ 165.1, 158.3, 154.5, 149.6, 147.1, 137.2, 130.9, 127.9, 126.1, 124.3, 117.1, 106.0, 80.9, 71.3, 71.1, 64.0, 37.1, 28.4.

Step 3: Preparation of 2-[4-(N-methyl-N—BOC) aminophenyl]-6-[(R/S)-3-methanesulfonyloxy-2-hydroxypropoxy]benzothiazole The target compound 2-[4-(N-methyl-N—BOC)aminophenyl]-6-[(R/S)-3-methanesulfonyloxy-2-hydroxypropoxy]benzothiazole (15-4, 300 mg, 51%) was obtained as white solid in the same manner as in step 3 of Example 1 using 2-[3-(N-methyl-N—BOC)aminophenyl]-6-((R/S)-2,3-dihydroxypropoxy)benzothiophene (14-4, 495 mg, 1.15 mmol) obtained in step 2, methanesulfonyl chloride (0.098 mL, 1.26 mmol) and diisopropylethylamine (0.240 mL, 1.38 mmol).

$^1$H NMR (200 MHz, CDCl$_3$) δ 1.49 (s, 9H), 3.09 (s, 3H), 3.31 (s, 3H), 4.10 (d, J=5.2 Hz, 2H), 4.28-4.37 (m, 1H), 4.42-4.51 (m, 2H), 7.05 (dd, J=8.8, 2.4 Hz, 1H), 7.32 (d, J=2.6 Hz, 1H), 7.37 (d, J=8.4 Hz, 2H), 7.91 (d, J=9.2 Hz, 1H), 7.98 (d, J=8.8 Hz, 2H);
$^{13}$C NMR (50 MHz, CDCl$_3$) δ 28.2, 37.0, 37.5, 37.8, 66.5, 68.0, 68.5, 79.2, 81.0, 105.1, 115.7, 123.6, 125.2, 127.4, 130.0, 136.2, 145.8, 149.0, 154.3, 156.0, 165.5.

Step 4: Preparation of 2-[4-(N-methyl-N—BOC) aminophenyl]-6-[(R/S)-3-methanesulfonyloxy-2-(tetrahydropyran-2-yloxy)propoxy]benzothiazole The target compound 2-[4-(N-methyl-N—BOC)aminophenyl]-6-[(R/S)-3-methanesulfonyloxy-2-(tetrahydropyran-2-yloxy)propoxy]benzothiazole (16-4, 278 mg, 88%) was obtained in the same manner as in step 4 of Example 1 except that 2-[4-(N-methyl-N—BOC)aminophenyl]-6-[(R/S)-3-methanesulfonyloxy-2-hydroxypropoxy]benzothiazole (15-4, 272 mg, 0.54 mmol) obtained in step 3, dihydropyran (DHP; 0.147 mL, 1.60 mmol) and pyridinium p-toluenesulfonate (PPTS; 68 mg, 0.27 mmol) were used.

$^1$H NMR (200 MHz, CDCl$_3$) δ 1.49 (s, 9H), 1.65-1.52 (m, 1.83-1.75 (m, 2H), 3.05 (s, 1.5H), 3.07 (s, 1.5H) 3.32 (s, 3H), 3.63-3.50 (m, 1H), 4.02-3.90 (m, 1H), 4.38-4.13 (m, 3H), 4.61-4.44 (m, 2H), 4.90-4.80 (m, 1H), 7.09 (dm, J=8.8 Hz, 1H), 7.42-7.34 (m, 3H), 7.94 (d, J=9.2 Hz, 1H), 7.99 (d, J=8.4 Hz, 2H);
$^{13}$C NMR (50 MHz, CDCl$_3$) δ 19.4, 25.1, 28.2, 30.48, 30.54, 36.9, 37.37, 37.42, 62.9, 64.2, 67.0, 67.4, 68.8, 69.5, 72.5, 72.8, 80.8, 99.0, 99.2, 105.1, 105.2, 115.8, 123.6, 125.2, 127.3, 130.1, 136.2, 145.8, 148.9, 149.0, 154.2, 156.2, 156.3, 165.2, 165.3.

Step 5 and 6: Preparation of 2-[4-(N-monomethyl) aminophenyl]-6-[(R/S)-3-fluoro-2-hydroxypropoxy] benzothiazole 2-[4-(N-Methyl-N—BOC)aminophenyl]-6-[(R/S)-3-methanesulfonyloxy-2-(tetrahydropyran-2-yloxy)propoxy]benzothiazole (16-4, 80 mg, 0.135 mmol) obtained in step 4 and tetrabutylammonium fluoride (TBAF; 53 mg, 0.20 mmol) were dissolved in t-amyl alcohol (3 mL) and then agitated at 100° C. for 6 hours. After cooling to room temperature, removing the solvent under reduced pressure, and adding 4 M HCl (0.40 mL) and tetrahydrofuran (1.6 mL), the target compound 2-[4-(N-monomethyl)aminophenyl]-6-[(R/S)-3-fluoro-2-hydroxypropoxy]benzothiazole (1-4, 35 mg, 78%) was obtained in the same manner as in steps 5 and 6 of Example 1.

$^1$H NMR (200 MHz, DMSO-d$_6$) δ 2.75 (d, J=4.8 Hz, 3H), 4.18-3.98 (m, 3H), 4.51 (dm, J=46.8 Hz, 2H), 5.49 (d, J=3.6 Hz, 1H), 6.41 (brs, 1H), 6.63 (d, J=8.8 Hz, 2H), 7.07 (dd, J=8.8, 2.2 Hz, 1H), 7.64 (d, J=2.2 Hz, 1H), 7.76 (d, J=8.8 Hz, 1H), 7.79 (d, J=8.8 Hz, 2H);
$^{13}$C NMR (50 MHz, DMSO-d$_6$) δ 29.4, 67.7 (d, J=19.4 Hz), 68.8 (d, J=7.6 Hz), 84.5 (d, J=166.6 Hz), 105.8, 111.5, 115.5, 120.3, 122.3, 128.4, 135.1, 148.5, 152.2, 155.8, 165.9.

Example 7

Preparation of 2-[2-(N-monomethyl)aminopyridin-6-yl]-6-[(R/S)-3-fluoro-2-hydroxypropoxy]benzothiazole Step 1: Preparation of 2-[2-(N-methyl-N—BOC) aminopyridin-5-yl]-6-allyloxybenzothiazole 2-[2-(N-Methyl-N—BOC)aminopyridin-5-yl]-6-allyloxybenzothiazole (13-5) was prepared in the same manner as step 1 of Example 1 using 2-[2-(N-methyl-N—BOC)aminopyridin-5-yl]-6-hydroxybenzothiazole (12-5, 310 mg, 0.867 mmol) obtained in Preparation Example 5, allyl bromide (0.111 mL, 1.30 mmol) and Cs$_2$CO$_3$ (571 mg, 1.73 mmol). The compound thus prepared was used in the subsequent step without purification.

Step 2: Preparation of 2-[2-(N-methyl-N—BOC) aminopyridin-5-yl]-6-((R/S)-2,3-dihydroxypropoxy) benzothiazole After sequentially adding osmium tetroxide (4 wt % in H$_2$O, 0.057 mL, 0.009 mmol), N-methylmorpholine N-oxide (152 mg, 1.30 mmol) and DABCO (2 mg, 0.018 mmol) to 2-[2-(N-methyl-N—BOC)aminopyridin-5-yl]-6-allyloxybenzothiazole (13-5) prepared in step 1, the target compound 2-[2-(N-methyl-N—BOC)aminopyridin-5-yl]-6-((R/S)-2,3-dihydroxypropoxy)benzothiazole (14-5, 320 mg, 95%) was obtained in the same manner as step 2 of Example 1.

$^1$H NMR (200 MHz, CDCl$_3$) δ 1.62 (s, 9H), 2.44 (t, J=5.9 Hz, 1H), 2.99 (d, J=4.2 Hz, 1H), 3.53 (s, 3H), 3.82-3.95 (m, 2H), 4.16-4.24 (m, 3H), 7.14 (dd, J=9.2, 2.6 Hz, 1H), 7.40 (d, J=2.6 Hz, 1H), 7.80 (dd, J=8.8, 2.6 Hz, 2H), 8.30 (dd, J=9.0, 2.4 Hz, 1H), 9.01 (d, J=2.6 Hz, 1H);
$^{13}$C NMR (125 MHz, CDCl$_3$) δ 28.3, 34.1, 63.5, 69.8, 70.3, 81.9, 105.4, 116.0, 118.3, 123.7, 124.9, 135.1, 136.1, 146.1, 148.9, 154.1, 156.5, 156.7, 162.6.

Step 3: Preparation of 2-[2-(N-methyl-N—BOC) aminopyridin-5-yl]-6-[(R/S)-3-methanesulfonyloxy-2-hydroxy propoxy]benzothiazole The target compound 2-[2-(N-methyl-N—BOC)aminopyridin-5-yl]-6-[(R/S)-3-methanesulfonyloxy-2-hydroxy propoxy]benzothiazole (15-5, 189 mg, 50%) was obtained in the same manner as in step of Example 1 using 2-[2-(N-methyl-N—BOC)aminopyridin-5-yl]-6-((R/S)-2,3-dihydroxypropoxy)benzothiazole (14-5, 320 mg, 0.742 mmol) obtained in step 2, methanesulfonyl chloride (MsCl; 0.063 mL, 0.815 mmol) and diisopropylethylamine (0.155 mL, 0.890 mmol).

$^1$H NMR (200 MHz, CDCl$_3$) δ 1.62 (s, 3H), 3.04 (d, J=5.2 Hz, 1H), 3.17 (s, 3H), 3.53 (s, 3H), 4.21 (d, J=4.6 Hz, 1H), 4.38-4.58 (m, 3H), 7.15 (dd, J=9.0, 2.2 Hz, 1H), 7.42 (d, J=2.2 Hz, 1H), 7.98 (d, J=8.8 Hz, 1H), 8.00 (d, J=8.8 Hz, 1H), 8.31 (dd, J=8.8, 2.4 Hz, 1H), 9.02 (d, J=2.2 Hz, 1H);
$^{13}$C NMR (125 MHz, CDCl$_3$) δ 28.3, 34.1, 37.6, 68.2, 68.6, 70.2, 81.9, 105.3, 115.9, 118.3, 123.8, 124.8, 135.2, 136.1, 146.1, 149.1, 154.1, 156.3, 156.5, 162.8.

Step 4: Preparation of 2-[2-(N-methyl-N—BOC) aminopyridin-5-yl]-6-[(R/S)-3-methanesulfonyloxy-2-(tetrahydropyran-2-yloxy)propoxy]benzothiazole The target compound 2-[2-(N-methyl-N—BOC)aminopyridin-5-yl]-6-[(R/S)-3-methanesulfonyloxy-2-(tetrahydropyran-2-yloxy)propoxy]benzothiazole (16-5, 260 mg, 89%) was obtained in the same manner as step 4 of Example 1 except that 2-[2-(N-methyl-N—BOC)aminopyridin-5-yl]-6-[(R/S)-3-methanesulfonyloxy-2-hydroxy propoxy]benzothiazole (15-5, 250 mg, 0.491 mmol) obtained in step 3, dihydropyran (DHP; 92 mg, 0.981 mmol) and pyridinium p-toluenesulfonate (PPTS; 25 mg, 0.098 mmol) were used.

$^1$H NMR (400 MHz, CDCl$_3$) δ 1.58 (s, 9H), 1.49-1.64 (m, 3H), 1.72-1.83 (m, 3H), 3.05 (s, 1.5H), 3.06 (s, 1.5H), 3.46 (s, 3H), 3.50-3.56 (m, 1H), 3.91-3.97 (m, 1H), 4.12-4.21 (m, 1.5H), 4.24-4.33 (m, 1.5H), 4.39-4.43 (m, 0.5H), 4.47-4.57 (m, 1.5H), 4.81-4.85 (m, 1H), 7.11-7.07 (m, 1H), 7.37 (dd,

J=7.6, 2.4 Hz, 1H), 7.91 (t, J=8.8 Hz, 2H), 8.23 (dd, J=8.8, 2.8 Hz, 1H), 8.95 (d, J=2.4 Hz, 1H);

$^{13}$C NMR (100 MHz, CDCl$_3$) δ 19.8, 25.4, 25.6, 28.5, 30.8, 30.9, 34.3, 37.7, 37.8, 63.2, 67.3, 67.7, 69.1, 69.8, 72.8, 73.2, 77.0, 77.3, 77.6, 82.0, 99.3, 99.6, 105.4, 105.5, 116.3, 118.5, 124.0, 125.10, 125.13, 135.4, 136.4, 146.3, 149.1, 149.2, 154.3, 156.68, 156.72, 156.80, 156.72, 156.8, 162.76, 162.82.

Steps 5 and 6: Preparation of 2-[2-(N-monomethyl) aminopyridin-5-yl]-6-[(R/S)-3-fluoro-2-hydroxypropoxy]benzothiazole 2-[2-(N-Methyl-N—BOC)aminopyridin-5-yl]-6-[(R/S)-3-methanesulfonyloxy-2-(tetrahydropyran-2-yloxy)propoxy]benzothiazole (16-5, 150 mg, 0.253 mmol) obtained in step 4 and tetrabutylammonium fluoride (TBAF; 81 mg, 0.303 mmol) were dissolved in t-amyl alcohol (3 mL) and then agitated at 100° C. for 6 hours. After cooling to room temperature, removing the solvent under reduced pressure, and adding 4 M HCl (0.63 mL) and tetrahydrofuran (2.5 mL), the target compound 2-[2-(N-monomethyl)aminopyridin-5-yl]-6-[(R/S)-3-fluoro-2-hydroxypropoxy]benzothiazole (1-5, 60 mg, 71%) was obtained in the same manner as in steps 5 and 6 of Example 1 (see FIG. 4).

$^1$H NMR (400 MHz, DMSO-d$_6$) δ 2.85 (d, J=4.8 Hz, 3H), 3.17 (d, J=4.8 Hz, 1H), 4.00-4.12 (m, 3H), 4.51 (dm, J=47.6 Hz, 2H), 6.57 (d, J=8.8 Hz, 1H), 7.09 (dd, J=9.2, 2.4 Hz, 1H), 7.23 (d, J=4.8 Hz, 1H), 7.67 (d, J=2.4 Hz, 1H), 7.83 (d, J=8.8 Hz, 1H), 7.96 (d, J=8.8 Hz, 1H), 8.64 (d, J=2.4 Hz, 1H);

$^{13}$C NMR (100 MHz, DMSO-d$_6$) δ 28.5, 68.2 (d, J=19.4 Hz), 69.4 (d, J=7.5 Hz), 85.0 (d, J=167.3 Hz), 106.4, 116.3, 118.1, 123.1, 125.6, 135.4, 135.6, 147.9, 148.8, 156.7, 161.2, 164.2.

Example 8

Preparation of 2-[2-(N-monomethyl)aminopyridin-5-yl]-6-[(S)-3-fluoro-2-hydroxypropoxy]benzothiazole Step 1': Preparation of 2-[2-(N-methyl-N—BOC) aminopyridin-5-yl]-6-[(S)-(2,2-dimethyl-1,3-dioxolan-4-yl)methyloxy]benzothiazole 2-[2-(N-Methyl-N—BOC)aminopyridin-5-yl]-6-hydroxybenzothiazole (12-5, 50 mg, 0.14 mmol) obtained in Preparation Example 5 and Cs$_2$CO$_3$ (137 mg, 0.42 mmol) were added to anhydrous dimethylformamide (0.6 mL). Then, (R)-(2,2-dimethyl-1,3-dioxolan-4-yl)methyl methanesulfonate ((R)-18a, 45 mg, 0.21 mmol) dissolved in anhydrous dimethylformamide (0.2 mL) was added thereto. After heating the reaction mixture at 100° C. for 1 hour and then cooling to room temperature, ice was added thereto. After extracting with ethyl acetate and removing water from the collected organic layer using sodium sulfate, column chromatography yielded the target compound 2-[2-(N-methyl-N—BOC)aminopyridin-5-yl]-6-[(S)-(2,2-dimethyl-1,3-dioxolan-4-yl)methyloxy]benzothiazole ((S)-19-2, 66 mg, 98%).

$^1$H NMR (400 MHz, CDCl$_3$) δ 1.41 (s, 3H), 1.48 (s, 3H), 1.55 (s, 9H), 3.46 (s, 3H), 3.93 (dd, J=8.4, 5.6 Hz, 1H), 4.02 (dd, J=9.6, 5.6 Hz, 1H), 4.13 (dd, J=9.2, 5.6 Hz, 1H), 4.19 (dd, J=8.4, 6.4 Hz, 1H), 4.49-4.55 (m, 1H), 7.11 (dd, J=8.8, 2.2 Hz, 1H), 7.37 (d, J=2.4 Hz, 1H), 7.92 (t, J=9.4 Hz, 2H), 8.24 (dd, J=8.8, 2.8 Hz, 1H), 8.95 (d, J=2.4 Hz);

$^{13}$C NMR (100 MHz, CDCl$_3$) δ 25.6, 27.0, 28.5, 34.3, 67.0, 69.6, 74.1, 82.0, 105.4, 110.1, 116.3, 118.4, 123.9, 125.1, 135.3, 136.3, 146.3, 149.1, 154.3, 156.0, 157.0, 162.6.

Step 2': Preparation of 2-[2-(N-methyl-N—BOC) aminopyridin-5-yl]-6-[(R)-2,3-dihydroxypropoxy] benzothiazole After adding Dowex 50WX2 (75 mg) resin to 2-[2-(N-methyl-N—BOC)aminopyridin-5-yl]-6-[(S)-(2,2-dimethyl-1,3-dioxolan-4-yl)methyloxy]benzothiazole ((S)-19-2, 150 mg, 0.32 mmol) obtained in step 1' dissolved in 10% H$_2$O/MeOH (3 mL), the reaction mixture was agitated at 50° C. for 10 hours and then cooled to room temperature. After filtering the reaction mixture and removing the solvent under reduced pressure, column chromatography yielded the target compound 2-[2-(N-methyl-N—BOC)aminopyridin-5-yl]-6-[(R)-2,3-dihydroxypropoxy]benzothiazol e ((R)-14-5, 58 mg, 42%).

$^1$H NMR (200 MHz, CDCl$_3$) δ 1.62 (s, 9H), 2.44 (t, J=5.9 Hz, 1H), 2.99 (d, J=4.2 Hz, 1H), 3.53 (s, 3H), 3.82-3.95 (m, 2H), 4.16-4.24 (m, 3H), 7.14 (dd, J=9.2, 2.6 Hz, 1H), 7.40 (d, J=2.6 Hz, 1H), 7.80 (dd, J=8.8, 2.6 Hz, 2H), 8.30 (dd, J=9.0, 2.4 Hz, 1H), 9.01 (d, J=2.6 Hz, 1H);

$^{13}$C NMR (125 MHz, CDCl$_3$) δ 28.3, 34.1, 63.5, 69.8, 70.3, 81.9, 105.4, 116.0, 118.3, 123.7, 124.9, 135.1, 136.1, 146.1, 148.9, 154.1, 156.5, 156.7, 162.6.

Step 3: Preparation of 2-[2-(N-methyl-N—BOC) aminopyridin-5-yl]-6-((S)-3-methanesulfonyloxy-2-hydroxypropoxy)benzothiazole The target compound 2-[2-(N-methyl-N—BOC)aminopyridin-5-yl]-6-((S)-3-methanesulfonyloxy-2-hydroxypropoxy)benzothiazole ((S)-15-5, 370 mg, 63%) was obtained in the same manner as in step 3 of Example 1 using 2-[2-(N-methyl-N—BOC)aminopyridin-5-yl]-6-((R)-2,3-dihydroxypropoxy)benzothiazole ((R)-14-5, 500 mg, 1.16 mmol) obtained in step 2, methanesulfonyl chloride (MsCl; 0.099 mL, 1.27 mmol) and diisopropylethylamine (0.404 mL, 2.32 mmol).

$^1$H NMR (200 MHz, CDCl$_3$) δ 1.62 (s, 3H), 3.04 (d, J=5.2 Hz, 1H), 3.17 (s, 3H), 3.53 (s, 3H), 4.21 (d, J=4.6 Hz, 1H), 4.38-4.58 (m, 3H), 7.15 (dd, J=9.0, 2.2 Hz, 1H), 7.42 (d, J=2.2 Hz, 1H), 7.98 (d, J=8.8 Hz, 1H), 8.00 (d, J=8.8 Hz, 1H), 8.31 (dd, J=8.8, 2.4 Hz, 1H), 9.02 (d, J=2.2 Hz, 1H);

$^{13}$C NMR (125 MHz, CDCl$_3$) δ 28.3, 34.1, 37.6, 68.2, 68.6, 70.2, 81.9, 105.3, 115.9, 118.3, 123.8, 124.8, 135.2, 136.1, 146.1, 149.1, 154.1, 156.3, 156.5, 162.8.

Step 4: Preparation of 2-[2-(N-methyl-N—BOC) aminopyridin-5-yl]-6-[(S)-3-methanesulfonyloxy-2-(tetrahydro pyran-2-yloxy)propoxy]benzothiazole The target compound 2-[2-(N-methyl-N—BOC)aminopyridin-5-yl]-6-[(S)-3-methanesulfonyloxy-2-(tetrahydro pyran-2-yloxy)propoxy]benzothiazole ((S)-16-5, 420 mg, 97%) was obtained in the same manner as step 4 of Example 1 except for using 2-[2-(N-methyl-N—BOC)aminopyridin-5-yl]-6-[(S)-3-methanesulfonyloxy-2-hydroxypropoxy]benzothiazole ((S)-15-5, 370 mg, 0.73 mmol) obtained in step 3, dihydropyran (DHP; 0.133 mL, 1.45 mmol) and pyridinium p-toluenesulfonate (PPTS; 37 mg, 0.15 mmol).

$^1$H NMR (400 MHz, CDCl$_3$) δ 1.58 (s, 9H), 1.49-1.64 (m, 3H), 1.72-1.83 (m, 3H), 3.05 (s, 1.5H), 3.06 (s, 1.5H), 3.46 (s, 3H), 3.50-3.56 (m, 1H), 3.91-3.97 (m, 1H), 4.12-4.21 (m, 1.5H), 4.24-4.33 (m, 1.5H), 4.39-4.43 (m, 0.5H), 4.47-4.57

(m, 1.5H), 4.81-4.85 (m, 1H), 7.11-7.07 (m, 1H), 7.37 (dd, J=7.6, 2.4 Hz, 1H), 7.91 (t, J=8.8 Hz, 2H), 8.23 (dd, J=8.8, 2.8 Hz, 1H), 8.95 (d, J=2.4 Hz, 1H);

$^{13}$C NMR (100 MHz, CDCl$_3$) δ 19.8, 25.4, 25.6, 28.5, 30.8, 30.9, 34.3, 37.7, 37.8, 63.2, 67.3, 67.7, 69.1, 69.8, 72.8, 73.2, 77.0, 77.3, 77.6, 82.0, 99.3, 99.6, 105.4, 105.5, 116.3, 118.5, 124.0, 125.10, 125.13, 135.4, 136.4, 146.3, 149.1, 149.2, 154.3, 156.68, 156.72, 156.80, 156.72, 156.8, 162.76, 162.82.

Figure 5:
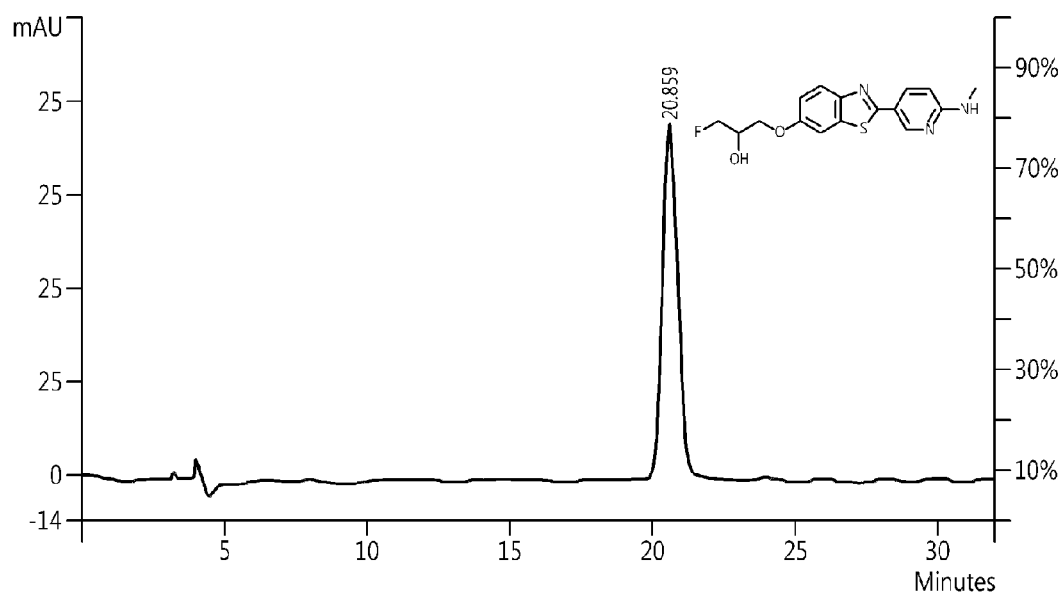
FIG. 5 shows a result of chiral HPLC analysis/purification of a compound of Example 8 ((S)-1-5)
Figure 14:
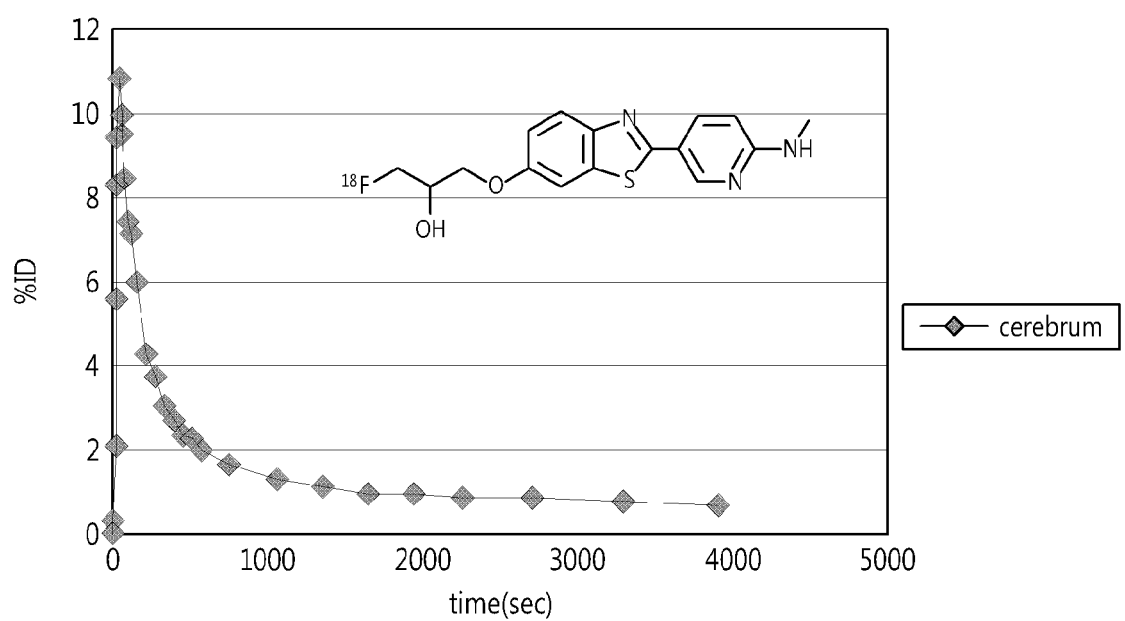
FIG. 14 shows a biodistribution curve of the compound of Example 13 ([$^{18}$F](R/S)-1-5) in a rat.

Steps 5 and 6: Preparation of 2-[2-(N-monomethyl) aminopyridin-5-yl]-6-[(S)-3-fluoro-2-hydroxypropoxy]benzothiazole 2-[2-(N-Methyl-N—BOC)aminopyridin-5-yl]-6-[(S)-3-methanesulfonyloxy-2-(tetrahydropyran-2-yloxy)propoxy]benzothiazole ((S)-16-5, 380 mg, 0.64 mmol) obtained in step 4 and tetrabutylammonium fluoride (TBAF; 205 mg, 0.77 mmol) were dissolved in t-amyl alcohol (3 mL) and then agitated at 100° C. for 6 hours. After cooling to room temperature, removing the solvent under reduced pressure, and adding 4 M HCl (1.5 mL) and tetrahydrofuran (5.0 mL), the target compound 2-[2-(N-monomethyl)aminopyridin-5-yl]-6-[(S)-3-fluoro-2-hydroxypropoxy]benzothiazole ((S)-1-5, 160 mg, 75%) was obtained in the same manner as in steps 5 and 6 of Example 1 (see FIG. 5).

$^1$H NMR (400 MHz, DMSO-d$_6$) δ 2.85 (d, J=4.8 Hz, 3H), 3.17 (d, J=4.8 Hz, 1H), 4.00-4.12 (m, 3H), 4.51 (dm, J=47.6 Hz, 2H), 6.57 (d, J=8.8 Hz, 1H), 7.09 (dd, J=9.2, 2.4 Hz, 1H), 7.23 (d, J=4.8 Hz, 1H), 7.67 (d, J=2.4 Hz, 1H), 7.83 (d, J=8.8 Hz, 1H), 7.96 (d, J=8.8 Hz, 1H), 8.64 (d, J=2.4 Hz, 1H);

$^{13}$C NMR (100 MHz, DMSO-d$_6$) δ 28.5, 68.2 (d, J=19.4 Hz), 69.4 (d, J=7.5 Hz), 85.0 (d, J=167.3 Hz), 106.4, 116.3, 118.1, 123.1, 125.6, 135.4, 135.6, 147.9, 148.8, 156.7, 161.2, 164.2.

Example 9

Preparation of 2-[2-(N-monomethyl)aminopyridin-5-yl]-6-[(R)-3-fluoro-2-hydroxypropoxy]benzothiazole Step 1': Preparation of 2-[2-(N-methyl-N—BOC) aminopyridin-5-yl]-6-[(R)-(2,2-dimethyl-1,3-dioxolan-4-yl)methyloxy]benzothiazole 2-[2-(N-Methyl-N—BOC)aminopyridin-5-yl]-6-[(R)-(2,2-dimethyl-1,3-dioxolan-4-yl)methyloxy]benzothiazole ((R)-19-2, 63 mg, 94%) was obtained in the same manner as in step 1' of Example 8 except that (S)-(2,2-dimethyl-1,3-dioxolan-4-yl)methyl methanesulfonate ((S)-18a) was used instead of (R)-(2,2-dimethyl-1,3-dioxolan-4-yl)methyl methanesulfonate.

$^1$H NMR (400 MHz, CDCl$_3$) δ 1.41 (s, 3H), 1.48 (s, 3H), 1.55 (s, 9H), 3.46 (s, 3H), 3.93 (dd, J=8.4, 5.6 Hz, 1H), 4.02 (dd, J=9.6, 5.6 Hz, 1H), 4.13 (dd, J=9.2, 5.6 Hz, 1H), 4.19 (dd, J=8.4, 6.4 Hz, 1H), 4.49-4.55 (m, 1H), 7.11 (dd, J=8.8, 2.2 Hz, 1H), 7.37 (d, J=2.4 Hz, 1H), 7.92 (t, J=9.4 Hz, 2H), 8.24 (dd, J=8.8, 2.8 Hz, 1H), 8.95 (d, J=2.4 Hz);

$^{13}$C NMR (100 MHz, CDCl$_3$) δ 25.6, 27.0, 28.5, 34.3, 67.0, 69.6, 74.1, 82.0, 105.4, 110.1, 116.3, 118.4, 123.9, 125.1, 135.3, 136.3, 146.3, 149.1, 154.3, 156.0, 157.0, 162.6.

Step 2': Preparation of 2-[2-(N-methyl-N—BOC) aminopyridin-5-yl]-6-[(S)-2,3-dihydroxypropoxy] benzothiazole 2-[2-(N-Methyl-N—BOC)aminopyridin-5-yl]-6-[(S)-2,3-dihydroxypropoxy]benzothiazole ((S)-14-5, 90 mg, 65%) was obtained in the same manner as in step 2' of Example 8 except that 2-[2-(N-methyl-N—BOC)aminopyridin-5-yl]-6-[(R)-(2,2-dimethyl-1,3-dioxolan-4-yl)methyloxy]benzothiazole ((R)-19-2, 150 mg, 0.32 mmol) obtained in step 1' dissolved in 10% H$_2$O/MeOH (3 mL) was used.

$^1$H NMR (200 MHz, CDCl$_3$) δ 1.62 (s, 9H), 2.44 (t, J=5.9 Hz, 1H), 2.99 (d, J=4.2 Hz, 1H), 3.53 (s, 3H), 3.82-3.95 (m, 2H), 4.16-4.24 (m, 3H), 7.14 (dd, J=9.2, 2.6 Hz, 1H), 7.40 (d, J=2.6 Hz, 1H), 7.80 (dd, J=8.8, 2.6 Hz, 2H), 8.30 (dd, J=9.0, 2.4 Hz, 1H), 9.01 (d, J=2.6 Hz, 1H);

$^{13}$C NMR (125 MHz, CDCl$_3$) δ 28.3, 34.1, 63.5, 69.8, 70.3, 81.9, 105.4, 116.0, 118.3, 123.7, 124.9, 135.1, 136.1, 146.1, 148.9, 154.1, 156.5, 156.7, 162.6.

Step 3: Preparation 2-[2-(N-methyl-N—BOC)aminopyridin-5-yl]-6-[(R)-3-methanesulfonyloxy-2-hydroxypropoxy]benzothiazole The target compound 2-[2-(N-methyl-N—BOC)aminopyridin-5-yl]-6-[(R)-3-methanesulfonyloxy-2-hydroxypropoxy]benzothiazole ((R)-15-5, 169 mg, 80%) was obtained in the same manner as in step 3 of Example 1 using 2-[2-(N-methyl-N—BOC)aminopyridin-5-yl]-6-[(S)-2,3-dihydroxypropoxy]benzothiazole ((S)-14-5, 180 mg, 0.42 mmol) obtained in step 2, methanesulfonyl chloride (MsCl; 0.036 mL, 0.46 mmol) and diisopropylethylamine (0.146 mL, 0.84 mmol).

$^1$H NMR (200 MHz, CDCl$_3$) δ 1.62 (s, 3H), 3.04 (d, J=5.2 Hz, 1H), 3.17 (s, 3H), 3.53 (s, 3H), 4.21 (d, J=4.6 Hz, 1H), 4.38-4.58 (m, 3H), 7.15 (dd, J=9.0, 2.2 Hz, 1H), 7.42 (d, J=2.2 Hz, 1H), 7.98 (d, J=8.8 Hz, 1H), 8.00 (d, J=8.8 Hz, 1H), 8.31 (dd, J=8.8, 2.4 Hz, 1H), 9.02 (d, J=2.2 Hz, 1H);

$^{13}$C NMR (125 MHz, CDCl$_3$) δ 28.3, 34.1, 37.6, 68.2, 68.6, 70.2, 81.9, 105.3, 115.9, 118.3, 123.8, 124.8, 135.2, 136.1, 146.1, 149.1, 154.1, 156.3, 156.5, 162.8.

Step 4: Preparation of 2-[2-(N-methyl-N—BOC) aminopyridin-5-yl]-6-[(R)-3-methanesulfonyloxy-2-(tetrahydropyran-2-yloxy)propoxy]benzothiazole The target compound 2-[2-(N-methyl-N—BOC)aminopyridin-5-yl]-6-[(R)-3-methanesulfonyloxy-2-(tetrahydropyran-2-yloxy)propoxy]benzothiazole ((R)-16-5, 335 mg, 93%) was obtained in the same manner as in step 4 of Example 1 except that 2-[2-(N-methyl-N—BOC)aminopyridin-5-yl]-6-[(R)-3-methanesulfonyloxy-2-hydroxypropoxy]benzothiazole ((R)-15-5, 308 mg, 0.61 mmol) obtained in step 3, dihydropyran (DHP; 0.111 mL, 1.21 mmol) and pyridinium p-toluenesulfonate (PPTS; 31 mg, 0.12 mmol) were used.

$^1$H NMR (400 MHz, CDCl$_3$) δ 1.58 (s, 9H), 1.49-1.64 (m, 3H), 1.72-1.83 (m, 3H), 3.05 (s, 1.5H), 3.06 (s, 1.5H), 3.46 (s, 3H), 3.50-3.56 (m, 1H), 3.91-3.97 (m, 1H), 4.12-4.21 (m, 1.5H), 4.24-4.33 (m, 1.5H), 4.39-4.43 (m, 0.5H), 4.47-4.57 (m, 1.5H), 4.81-4.85 (m, 1H), 7.11-7.07 (m, 1H), 7.37 (dd, J=7.6, 2.4 Hz, 1H), 7.91 (t, J=8.8 Hz, 2H), 8.23 (dd, J=8.8, 2.8 Hz, 1H), 8.95 (d, J=2.4 Hz, 1H);

$^{13}$C NMR (100 MHz, CDCl$_3$) δ 19.8, 25.4, 25.6, 28.5, 30.8, 30.9, 34.3, 37.7, 37.8, 63.2, 67.3, 67.7, 69.1, 69.8, 72.8, 73.2, 77.0, 77.3, 77.6, 82.0, 99.3, 99.6, 105.4, 105.5, 116.3, 118.5, 124.0, 125.10, 125.13, 135.4, 136.4, 146.3, 149.1, 149.2, 154.3, 156.68, 156.72, 156.80, 156.72, 156.8, 162.76, 162.82.

Steps 5 and 6: Preparation of 2-[2-(N-monomethyl) aminopyridin-5-yl]-6-[(R)-3-fluoro-2-hydroxypropoxy]benzothiazole 2-[2-(N-Methyl-N—BOC)aminopyridin-5-yl]-6-[(R)-3-methanesulfonyloxy-2-(tetrahydropyran-2-yloxy)propoxy]

benzothiazole ((R)-16-5, 150 mg, 0.253 mmol) obtained in step 4 and tetrabutylammonium fluoride (TBAF; 81 mg, 0.303 mmol) were dissolved in t-amyl alcohol (3 mL) and then agitated at 100° C. for 6 hours. After cooling to room temperature, removing the solvent under reduced pressure, and adding 4 M HCl (0.63 mL) and tetrahydrofuran (2.5 mL), the target compound 2-[2-(N-monomethyl)aminopyridin-5-yl]-6-[(R)-3-fluoro-2-hydroxypropoxy]benzothiazole ((R)-1-5, 60 mg, 71%) was obtained in the same manner as in steps 5 and 6 of Example 1 (see FIG. 6).

$^1$H NMR (400 MHz, DMSO-$d_6$) δ 2.85 (d, J=4.8 Hz, 3H), 3.17 (d, J=4.8 Hz, 1H), 4.00-4.12 (m, 3H), 4.51 (dm, J=47.6 Hz, 2H), 6.57 (d, J=8.8 Hz, 1H), 7.09 (dd, J=9.2, 2.4 Hz, 1H), 7.23 (d, J=4.8 Hz, 1H), 7.67 (d, J=2.4 Hz, 1H), 7.83 (d, J=8.8 Hz, 1H), 7.96 (d, J=8.8 Hz, 1H), 8.64 (d, J=2.4 Hz, 1H);

$^{13}$C NMR (100 MHz, DMSO-$d_6$) δ 28.5, 68.2 (d, J=19.4 Hz), 69.4 (d, J=7.5 Hz), 85.0 (d, J=167.3 Hz), 106.4, 116.3, 118.1, 123.1, 125.6, 135.4, 135.6, 147.9, 148.8, 156.7, 161.2, 164.2.

Test Example 1

Binding Assay Using β-Amyloid Peptide 1-1: Preparation of β-Amyloid (Aβ$_{1-42}$) Fibrils'

β-Amyloid peptide (Aβ$_{1-42}$, Bachem, 1 mg) was completely dissolved in DMSO (1 mL) and then mixed well after adding phosphate buffer (pH 7.4, 9 mL). β-Amyloid fibrils produced by incubating at 37° C. for 60 minutes were distributed into e-tubes, 0.5 mL each, and stored in a refrigerator at −80° C.

1-2: Identification of β-Amyloid (Aβ$_{1-42}$) Fibrils

In order to investigate whether β-amyloid fibrils were produced successfully from the β-amyloid peptides, 5 μM thioflavin T (ThT, 150 μL) was added to the β-amyloid fibrils (50 μL), and fluorescence intensity of ThT bound to the β-amyloid fibrils was measured at $\lambda_{ex}/\lambda_{em}$=450 nm/480 nm using a spectrophotometer.

1-3: Synthesis of 2-[4-(N,N-dimethyl)aminophenyl]-6-[$^{125}$I]iodobenzothiazole 50 μL of a solution with a precursor compound (47, 1 mg) dissolved in ethanol (1 mL) was placed in a glass test tube, and 30% hydrogen peroxide (50 μL), 1 N HCl (50 μL) and ethanol (200 μL) were added thereto. Then, [$^{125}$I]NaI was added thereto at 1.0 mCi/100 μL. The glass test tube was capped and allowed to stand at room temperature for 10 minutes. 10 Minutes later, after terminating the reaction by adding saturated NaHSO$_4$ aqueous solution (100 μL), extracting the product into an organic layer using ethyl acetate (500 μL×2), and drying with sodium sulfate, the organic solvent was removed from the resulting solution at room temperature while passing high-purity nitrogen gas over the solution. After completely removing the organic solvent and diluting by adding ethanol (200 μL), the resulting mixture was subjected to high-performance liquid chromatography (HPLC). The target compound 2-[4-(N,N-dimethyl)aminophenyl]-6-[$^{125}$I]iodobenzothiazole (48, [$^{125}$I]TZDM) labeled with I-123 was obtained with a final radiochemical yield of 89%.

1-4: Test of Binding Ability 1-4-1. Dissociation Constant ($K_d$) of [$^{125}$I]TZDM (48)

β-Amyloid (Aβ$_{1-42}$) fibrils were prepared in a 12 mm×75 mm borosilicate test tube at a concentration of 10 nM (final reaction concentration). After adding $^{125}$I-labeled TZDM (48, 50 μL, 0.046-5.9 pM) and adding 10% ethanol to a total volume of 1 mL, the resulting mixture was subjected to incubation at room temperature for 3 hours. 3 Hours later, after separating [$^{125}$I]TZDM (48) bound to the β-amyloid (Aβ$_{1-42}$) fibrils from unbound [$^{125}$I]TZDM (48) using a cell harvester (Brandel M-24R), gamma radiation was measured using a gamma counter and then the dissociation constant $K_d$ was calculated. 2 μM ThT was used to test non-specific binding.

The dissociation constant ($K_d$) of [$^{125}$I]TZDM (48) was 0.13 nM.

1-4-2. Test of Inhibitory Binding Ability

10% ethanol (0.850 mL) was placed in a 12 mm×75 mm borosilicate test tube. After adding β-amyloid (Aβ$_{1-42}$) fibrils (50 μL, final reaction concentration=10 nM), the compound according to the present disclosure (compounds prepared in Examples 1 to 9, 50 μL) was added as an inhibitor (final concentration in the reaction solution=1 μM). For comparison (control), the [$^{11}$C]PIB compound of Chemical Formula V was added. Then, after adding [$^{125}$I]TZDM (48) (50 μL, final reaction concentration=0.05 nM), the resulting mixture was subjected to incubation at room temperature for 3 hours. 3 Hours later, after separating [$^{125}$I]TZDM (48) bound to the β-amyloid (Aβ$_{1-42}$) fibrils from unbound [$^{125}$I]TZDM (48) using a cell harvester, gamma radiation was measured using a gamma counter. 2 μM ThT was used for testing of non-specific binding.

The binding affinity ($K_i$) for [$^{125}$I]TZDM (48) is shown in Table 2.

TABLE 2

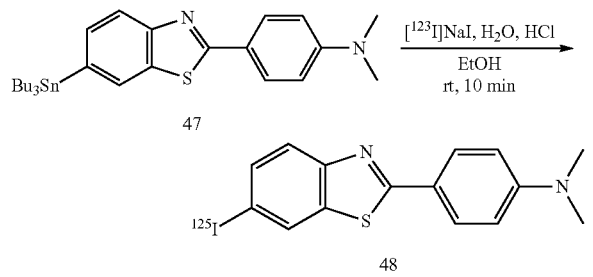

| Compound | | $K_i$ (nM) |
|---|---|---|
| Example 1 | (structure) | 1.20 (0.44) |

TABLE 2-continued

| | Compound | $K_i$ (nM) |
|---|---|---|
| Example 2 | | 0.49 (0.44) |
| Example 3 | | |
| Example 4 | | |
| Example 5 | | 0.42 (0.38) |
| Example 6 | | 1.06 (0.98) |
| Example 7 | | |
| Example 8 | | 0.16 (0.99) |
| Example 9 | | |

*The numbers in parentheses are binding affinity values for the PIB compound of Chemical Formula V.

As shown in Table 2, the compounds of the present disclosure exhibited stronger binding affinity ($K_i$) to β-amyloid than the control compound [$^{11}$C]PIB. Especially, the compounds of Examples 1, 2, 5, 6 and 8 showed superior binding affinity of 1.20 nM, 0.49 nM, 0.42 nM, 1.06 nM and 0.16 nM, respectively. In particular, the derivatives of the present disclosure have such excellent binding ability to β-amyloid as to inhibit binding of [$^{125}$I]TZDM (48), which is known to have a strong binding affinity to the β-amyloid peptide.

Since the compounds according to the present disclosure strongly bind to β-amyloid, they can be used as a diagnostic reagent for detecting Alzheimer's disease early in a noninvasive manner after labeling with an isotope. In addition, since they bind with low molecular weight β-amyloid peptide aggregates and inhibit formation of malignant, high molecular weight β-amyloid plaques, they can be useful as a therapeutic agent for a degenerative brain disease such as Alzheimer's disease.

Example 10

Preparation of 2-[2-(N-monomethyl)aminopyridin-5-yl]-6-[(R/S)-3-[$^{18}$F]fluoro-2-hydroxypropoxy]benzothiophene labeled with F-18

After placing [$^{18}$F]fluoride (1.8 GBq) in a quaternary alkylammonium cartridge, [$^{18}$F]fluoride was eluted into a reactor using a methanol eluent (0.7 mL) containing tetrabutylammonium bicarbonate (TBAHCO$_3$, 0.08 mL). After removing the solvent from the eluate by heating at 100° C. while passing nitrogen over the solution, acetonitrile (0.5 mL) was added to completely remove water from the reactor. It took between 1.5 and 2 minutes to remove water. The precursor (5 mg) obtained in step 4 of Example 2 was dissolved in tetrahydrofuran (0.05 mL) and t-amyl alcohol (1.0 mL) and then added to the reactor. After agitating the reaction mixture at 120° C. for 20 minutes, the reaction solvent was removed by heating at 100° C. while passing nitrogen gas over the solution. After adding 1 N HCl aqueous solution (0.5 mL) and agitating at 100° C. for 5 minutes, the reaction solution was neutralized by adding aqueous 2 N NaOH (0.25 mL) and the target compound was obtained by HPLC.

[$^{18}$F]Fluorination yield measured using a radio-thin layer chromatography (radio-TLC) scanner was 23.27%, and radiochemical yield of the final compound was 16.95% (decay-corrected). Total synthesis time was 65 minutes including purification.

Example 11

Preparation of 2-[3-(N-monomethyl)aminopyridazin-5-yl]-6-[(R/S)-3-[$^{18}$F]fluoro-2-hydroxypropoxy]benzothiophene labeled with F-18

The target compound was obtained in the same manner as in Example 10 except for placing [$^{18}$F]fluoride (468.8 MBq) in a quaternary alkylammonium cartridge and then eluting [$^{18}$F]fluoride to a reactor and using the precursor obtained in step 4 of Example 5.

[$^{18}$F]Fluorination yield measured using a radio-TLC scanner was 14.08%, and radiochemical yield of the final compound was 8.59% (decay-corrected). Total synthesis time was 55 minutes including purification.

Example 12

Preparation of 2-[3-(N-monomethyl)aminophenyl]-6-[(R/S)-3-[$^{18}$F]fluoro-2-hydroxypropoxy]benzothiazole labeled with F-18

The target compound was obtained in the same manner as in Example 10 except for placing [$^{18}$F]fluoride (1.49 GBq) in a quaternary alkylammonium cartridge and then eluting [$^{18}$F]fluoride into a reactor and using the precursor obtained in step 4 of Example 6.

Radiochemical yield of the final compound was 16.95% (decay-corrected). Total synthesis time was 70 minutes including purification.

Example 13

Preparation of 2-[2-(N-monomethyl)aminopyridin-5-yl]-6-[(R/S)-3-[$^{18}$F]fluoro-2-hydroxypropoxy]benzothiazole labeled with F-18

The target compound was obtained in the same manner as in Example 10 except for placing [$^{18}$F]fluoride (1.49 GBq) in a quaternary alkylammonium cartridge and then eluting [$^{18}$F] fluoride into a reactor and using the precursor obtained in step 4 of Example 7.

Radiochemical yield of the final compound was 40.17% (decay-corrected). Total synthesis time was 66 minutes including purification.

The compounds prepared in Examples 10 to 13 were identified by HPLC. Results are shown in FIGS. 7 to 10.

Test Example 2

Test of In Vivo Distribution of F-18-Labeled Compounds

Drugs acting in the brain should be able to pass through the blood-brain barrier. For example, a drug for treating brain diseases including Alzheimer's disease needs to pass through the blood-brain barrier rapidly and the compound unbound to β-amyloid has to be quickly released out of the brain through the blood-brain barrier.

In order to test the passing of the aryl derivative with the (3-fluoro-2-hydroxy)propyl group according to the present disclosure through the blood-brain barrier, the following experiment was carried out.

After administering the F-18-labeled aryl derivatives prepared in Examples 10 to 13 or 2-(4-(N-monomethyl)aminophenyl)-6-(3-[$^{18}$F]fluoropropoxy)benzothiophene with no hydroxyl group, as control, to SD rats, peak concentration in the brain and concentrations at 2 minutes ([2 min]) and 30 minutes ([30 min]) were measured and pharmacokinetic properties were quantitatively compared.

A [2 min]/[30 min] value smaller than 1 indicates that the relevant compound cannot pass through the blood-brain barrier well. A larger value indicates easier passage through the blood-brain barrier.

Results are shown in Table 3 and FIGS. 11 to 14.

TABLE 3

| | Concentration in brain of rats | | | | |
|---|---|---|---|---|---|
| | Highest ([peak]) | At 2 minutes ([2 min]) | At 30 minutes ([30 min]) | [peak]/ [30 min] | [2 min]/ [30 min] |
| Control | | 2.02 | 2.18 | | 0.93 |
| Example 10 | 22.4 (30 sec) | 16.5 | 2.2 | 10.3 | 7.5 |
| Example 12 | 22.6 (25 sec) | 15.7 | 2.9 | 7.7 | 5.3 |
| Example 13 | 11.1 (45 sec) | 6.5 | 1.0 | 10.8 | 6.1 |

As seen from Table 3 and FIGS. 11 to 14, 2-[4-(N-monomethyl)aminophenyl]-6-β-[$^{18}$F]fluoropropoxy)benzothiophene with no hydroxyl group at the propyl residue showed very low initial brain inflow (at 2 minutes) and the [2 min]/[30 min] value was less than or equal to 1. This means that the compound cannot pass through the blood-brain barrier well.

In contrast, the compound of Example 10 with a hydroxyl group introduced at the propyl residue showed very rapid initial brain inflow and the [2 min]/[30 min] value was as large as 7.5. This suggests that the compound has logP and polarity values suitable for passage through the blood-brain barrier.

This value is 8.1 times that of the compound with no hydroxyl group at the propyl residue and demonstrates that the hydroxyl group facilitates passage through the blood-brain barrier than the compound with no hydroxyl group at the propyl residue. The compounds of Examples 12 and 13 having hydroxy groups also showed superior [2 min]/[30 min] values.

Thus, it was confirmed through animal experiments that the (3-fluoro-2-hydroxy)propyl group of the compounds of the present disclosure have can be easily labeled with F-18 and provides physical properties pharmacokinetically adequate for a diagnostic agent of brain diseases. The compounds with the (3-fluoro-2-hydroxy)propyl group are useful in development of diagnostic agents for various degenerative brain diseases in addition to Alzheimer's disease.

The compound of the present disclosure can be prepared into various formulations. The following examples are provided as some non-limiting formulation examples containing the compound according to the present disclosure as an active ingredient.

Formulation Example 1

Preparation of Tablet

| Compound represented by Chemical Formula 1 | 5.0 mg |
|---|---|
| Lactose | 14.1 mg |
| Crospovidone USNF | 0.8 mg |
| Magnesium stearate | 0.1 mg |

The compound represented by Chemical Formula 1 was sieved, mixed with lactose, crospovidone USNF and magnesium stearate, and then compressed into a tablet.

Formulation Example 2

Preparation of Capsule

| Compound represented by Chemical Formula 1 | 5.0 mg |
|---|---|
| Lactose | 14.8 mg |
| Polyvinylpyrrolidone | 10.0 mg |
| Magnesium stearate | 0.2 mg |

Compound represented by Chemical Formula 1 was sieved and mixed with lactose, polyvinylpyrrolidone and magnesium stearate. The resulting mixture was compounded according to a commonly employed capsule preparation method and then filled in a gelatin capsule.

Formulation Example 3

Preparation of Injection

| Compound represented by Chemical Formula 1 | 100 mg |
|---|---|
| Mannitol | 180 mg |
| $Na_2HPO_4 \cdot 12H_2O$ | 26 mg |
| Distilled water | 2974 mg |

Compound represented by Chemical Formula 1 was dissolved in distilled water along with mannitol and $Na_2HPO_4 \cdot 12H_2O$. After adjusting pH to about 7.5 and sterilizing, an injection was prepared according to a commonly employed method.

The invention claimed is:

1. (3-fluoro-2-hydroxy)propyl-functionalized aryl derivatives represented by Chemical Formula 1, which are optically active or racemic, or a pharmaceutically acceptable salt thereof:

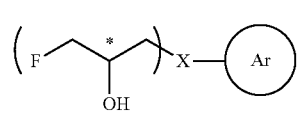

wherein
F is $^{18}F$ or $^{19}F$;
X is O or N;

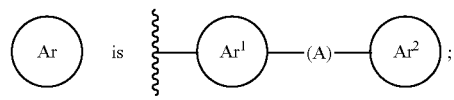

$Ar^1$ is benzothiazole, $Ar^1$ being unsubstituted or substituted with one or more of

and $NR^1R^2$;
$Ar^2$ is pyridine, $Ar^2$ being unsubstituted or substituted with one or more of

and $NR^1R^2$;
$R^1$ and $R^2$ are independently H or $C_{1-4}$ alkyl;
(A) is a single bond.

2. The aryl derivative or the pharmaceutically acceptable salt thereof according to claim 1,
wherein
$Ar^2$ is

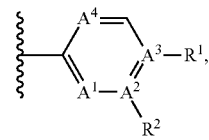

wherein $A^1$ and $A^4$ are each CH, $A^2$ is N, $A^3$ is C;
$R^1$ and $R^2$ are independently H, amine, methylamine or dimethylamine.

3. The aryl derivative or the pharmaceutically acceptable salt thereof according to claim 1, wherein the aryl derivative is:
2-[2-(N-monomethyl)aminopyridin-5-yl]-6-[(R/S)-3-fluoro-2-hydroxypropoxy]benzothiazole;
2-[2-(N-monomethyl)aminopyridin-5-yl]-6-[(S)-3-fluoro-2-hydroxypropoxy]benzothiazole;
or
2-[2-(N-monomethyl)aminopyridin-5-yl]-6-[(R)-3-fluoro-2-hydroxypropoxy]benzothiazole; and
wherein the fluoro of the aryl derivative is [$^{18}F$]fluoro or [$^{19}F$]fluoro.

* * * * *